United States Patent
Stankewicz et al.

(10) Patent No.: US 10,604,739 B2
(45) Date of Patent: *Mar. 31, 2020

(54) CARDIOMYOCYTE PRODUCTION

(71) Applicant: Cellular Dynamics International, Inc., Madison, WI (US)

(72) Inventors: Casey Stankewicz, Madison, WI (US); Matt Riley, Madison, WI (US); Nathaniel Beardsley, Oregon, WI (US); Wen Bo Wang, Waunakee, WI (US); Peter Fuhrken, Madison, WI (US); Steven Kattman, Madison, WI (US)

(73) Assignee: FUJIFILM Cellular Dynamics, Inc., Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/498,522

(22) Filed: Apr. 27, 2017

(65) Prior Publication Data

US 2017/0226481 A1 Aug. 10, 2017

Related U.S. Application Data

(60) Division of application No. 14/665,616, filed on Mar. 23, 2015, now Pat. No. 9,957,482, which is a continuation of application No. 13/794,679, filed on Mar. 11, 2013, now abandoned, which is a division of application No. 12/907,714, filed on Oct. 19, 2010, now Pat. No. 8,415,155.

(60) Provisional application No. 61/252,919, filed on Oct. 19, 2009.

(51) Int. Cl.
| | | |
|---|---|---|
| *C12N 5/077* | (2010.01) | |
| *C12N 5/0735* | (2010.01) | |
| *A61K 48/00* | (2006.01) | |
| *C07K 14/50* | (2006.01) | |
| *C07H 21/04* | (2006.01) | |
| *C07K 14/475* | (2006.01) | |

(52) U.S. Cl.
CPC ........... *C12N 5/0657* (2013.01); *A61K 48/00* (2013.01); *C07H 21/04* (2013.01); *C07K 14/475* (2013.01); *C07K 14/50* (2013.01); *C12N 5/0606* (2013.01); *C12N 2501/105* (2013.01); *C12N 2501/11* (2013.01); *C12N 2501/115* (2013.01); *C12N 2501/12* (2013.01); *C12N 2501/155* (2013.01); *C12N 2501/16* (2013.01); *C12N 2501/48* (2013.01); *C12N 2501/70* (2013.01); *C12N 2501/727* (2013.01); *C12N 2506/02* (2013.01); *C12N 2506/45* (2013.01); *C12N 2509/00* (2013.01); *C12N 2510/00* (2013.01)

(58) Field of Classification Search
CPC ........ A61K 48/00; A61K 38/00; A61K 38/02; C07K 14/4725; C12N 15/102
USPC .................................................. 435/366, 375
See application file for complete search history.

(56) References Cited

U.S. PATENT DOCUMENTS

| | | | |
|---|---|---|---|
| 6,602,711 B1 | 8/2003 | Thomson et al. | |
| 7,727,762 B2 | 6/2010 | Fukuda et al. | |
| 7,763,464 B2 | 7/2010 | Xu | |
| 8,822,684 B1 | 9/2014 | Hong et al. | |
| 2002/0166134 A1 | 11/2001 | Field et al. | |
| 2003/0073234 A1 | 4/2003 | Amit et al. | |
| 2007/0134215 A1 | 6/2007 | Fukuda et al. | |
| 2008/0038820 A1 | 2/2008 | Rudy-Reil | |
| 2008/0113433 A1 | 5/2008 | Robins et al. | |
| 2008/0171385 A1 | 7/2008 | Bergendahl et al. | |
| 2008/0226558 A1 | 9/2008 | Keller et al. | |
| 2008/0254003 A1 | 10/2008 | Passier et al. | |
| 2009/0047739 A1 | 2/2009 | Gold et al. | |
| 2010/0172883 A1 | 7/2010 | Bruneau et al. | |
| 2010/0189699 A1 | 7/2010 | Hattori et al. | |
| 2012/0009645 A1 | 1/2012 | Oh et al. | |
| 2012/0058561 A1 | 3/2012 | Sato | |

FOREIGN PATENT DOCUMENTS

| | | |
|---|---|---|
| EP | 2 014 766 | 1/2009 |
| KR | 10-2009-0090586 | 8/2009 |
| WO | WO 2001/051616 | 7/2001 |
| WO | WO 2003/004626 | 1/2003 |
| WO | WO 2007/002136 | 1/2007 |
| WO | WO 2008/035110 | 3/2008 |
| WO | WO 2008/094597 | 8/2008 |
| WO | WO 2008/106771 | 9/2008 |
| WO | WO 2009/017254 | 2/2009 |
| WO | WO 2009/120762 | 10/2009 |
| WO | WO 2010/007031 | 1/2010 |

OTHER PUBLICATIONS

Allegrucci et al., 2006, Human Reproduction Update, Vol. Advance Access published on Aug. 26, 2006, p. 1-18.*
Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Burridge et al., 2007, Stem Cells, vol. 25, p. 929-938.*
Fukuda et al., 2007, US 20070134215 A1.*

(Continued)

*Primary Examiner* — Janet L Epps-Smith
(74) *Attorney, Agent, or Firm* — Parker Highlander PLLC

(57) ABSTRACT

Methods and composition for the production of cardiomyocytes from differentiation of pluripotent stem cells are provided. For example, in certain aspects methods including differentiating pluripotent stem cells in a large volume of suspension culture in the presence of ROCK inhibitors are described. In further aspects, methods for differentiation of stem cells into cardiomyocytes that overcome variability between different stem cell clones and different batch of culture medium are provided.

14 Claims, 37 Drawing Sheets

(56) References Cited

OTHER PUBLICATIONS

Naito et al., "Developmental stage-specific biphasic roles of Wnt/β-catenin signaling in cardiomyogenesis and hematopoiesis," *PNAS*, 103(52):19812-19817, 2006.

Abeyta et al., "Unique gene expression signatures of independently-derived human embryonic stem cell lines," *Human Molecular Genetics*, 13(6):601-608, 2004.

Allegrucci et al., "Differences between human embryonic stem cell lines," *Human Reproduction Update*, 13(2):103-20, 2007. Epub Aug. 26, 2006.

Bauwens et al., "Control of human embryonic stem cell colony and aggregate size heterogeneity influence differentiation trajectories," *Stem Cells*, 26(9):2300-10, 2008.

Boheler et al., "Differentiation of pluripotent embryonic stem cells into cardiomyocytes," *Circulation Research*, 91:189, 2002.

Burridge et al., "A universal system for highly efficient cardiac differentiations of human induced pluripotent stem cells that eliminates interline variability," *PLoS One*, 6(4):e18293, 2011.

Burridge et al., "Improved human embryonic stem cell embryoid body homogeneity and cardiomyocyte differentiation from a novel V-96 plate aggregation system highlights interline variability," *Stem Cells*, 25:929-938, 2007.

Carpenedo et al., "Rotary suspension culture enhances the efficiency, yield, and homogeneity of embryoid body differentiation," *Stem Cells*, 25(9):2224-34, 2007.

Claassen et al., "ROCK inhibition enhances the recovery and growth of cryopreserved human embryonic stem cells and human induced pluripotent stem cells," *Mol. Reprod. Dev.*, 76(8):722-732, 2009.

Davidson et al., "Novel cell lines derived from adult human ventricular cardiomyocytes,"*Journal of Molecular and Cellular Cardiology*, 39:133-147, 2005.

Denning et al., "Common culture conditions for maintenance and cardiomyocyte differentiation of the human embryonic stem cell lines, BG01 and HUES-7," *Int. J. Dev. Biol.*, 50:27-37, 2006.

Extended European Search Report issued in European Application No. 10828771.5, dated Aug. 26, 2013.

Gai et al., "Generation and characterization of functional cardiomyocytes using induced pluripotent stem cells derived from human fibroblasts," *Cell Biol. Int.*, 33:1184-1193, 2009.

Gallo et al., "Human embryonic stem cell-derived cardiomyoctes: inducing strategies," *Regenerative Med.*, 1(2):183-194, 2006.

Hao et al., "Dorsomorphin, a selective small molecule inhibitor of BMP signaling, promotes cardiomyogenesis in embryonic stem cells," *PLoS One*, 3(8):e2904, 2008. 8 pages.

Harb et al., "The Rho-Rock-Myosin signaling axis determines cell-cell integrity of sel-renewing pluripotent stem cells," *PLoS One*, 3(8):e3001, 2008.

Ireland, *Visualing Human Biology*, 3$^{rd}$ Ed., Wiley and Sons Inc., p. 527, 2008.

Kattman et al., "Stage-specific optimization of activin/nodal and BMP signaling promotes cardiac differentiation of mouse and human pluripotent stem cell lines," *Cell Stem Cell*, 8(2):228-240, 2011.

Kawai et al., "Efficient cardiomyogenic differentiation of embryonic stem cell by fibroblast growth factor 2 and bone morphogenetic protein 2," *Circ J*, 68:691-702, 2004.

Kennedy et al., "Development of the hemangioblast defines the onset of hematopoiesis in human ES cell differentiation cultures," *Blood*, 109:2679-2687, 2007.

Kim et al., "Use of long-term cultured embryoid bodies may enhance cardiomyocyte differentiation by BMP2," *Yonsei Med. J.*, 49(5):819-827, 2008.

Krawetz et al., "Human embryonic stem cells: caught between a ROCK inhibitor and a hard place," *Bioessays*, 31(3):336-43, 2009.

Laflamme et al., "Cardiomyocytes derived from human embryonic stem cells in pro-survival factors enhance function of infracted rat hearts," *Nature Biotechnology*, 25(9):1015-24, 2007.

Lev et al., "Differentiation pathways in human embryonic stem cell-derived cardiomyocytes," *Ann. N.Y. Acad. Sci.*, 1047:50-65, 2005.

Martin-Ibañez et al., "Novel cryopreservation method for dissociated human embryonic stem cells in the presence of a ROCK inhibitor," *Human Reproduction*, 23(12):2744-2754, 2008.

Martins et al., "The current status of iPS cells in cardiac research and their potential for tissue engineering and regenerative medicine," *Stem Cell Rev and Rep*, 10:177-190, 2014.

Mauritz et al., "Generation of functional murine cardiac myocytes from induced pluripotent stem cells," *Circulation*, 118:507-517, 2008.

Narazaki et al., "Directed and systematic differentiation of cardiovascular cells from mouse induced pluripotent stem cells," *Circulation*, 118(5):498-506, 2008.

Niebruegge et al., "Cardiomyocyte production in mass suspension culture: embryonic stem cells as a source for great amounts of functional cardiomyocytes," *Tissue Engineering: Part A*, 14(10):1591-1601, 2008.

Niebruegge et al., "Generation of human embryonic stem cell-derived mesoderm and cardiac cells using size-specified aggregates in an oxygen-controlled bioreactor," *Biotechnology and Bioengineering*, 102(2):493-507, 2009.

Office Action issued in Australian Application No. 2010315712, dated Nov. 27, 2013.

Office Action issued in European Application No. 10828771.5, dated Nov. 24, 2014.

Office Action issued in Japanese Application No. 2012-534443, dated Jan. 21, 2015, and English language translation thereof.

Office Action issued in U.S. Appl. No. 13/794,654, dated Jul. 7, 2014.

Office Action issued in U.S. Appl. No. 13/794,654, dated Mar. 18, 2015.

Office Action issued in U.S. Appl. No. 13/794,654, dated Oct. 8, 2014.

Office Action issued in U.S. Appl. No. 13/794,679, dated Jun. 16, 2014.

Office Action issued in U.S. Appl. No. 13/794,679, dated Sep. 25, 2014.

Office Action issued in U.S. Appl. No. 12/907,714, dated Mar. 13, 2012.

Office Action issued in U.S. Appl. No. 12/907,714, dated Jun. 7, 2012.

Office Action issued in U.S. Appl. No. 12/907,714, dated Nov. 2, 2012.

Pandur, "What does it take to make a heart," *Biology of the Cell*, 97:197-210, 2005.

Pawani and Bhartiya, "Pluripotent stem cells for cardiac regeneration: overview of recent advances & emerging trends," *Indian J Med Res.*, 137(2):270-282, 2013.

PCT International Preliminary Report on Patentability issued in International application No. PCT/US2010/053216, dated Mar. 30, 2012.

PCT International Search Report and Written Opinion issued in International application No. PCT/US2010/053216, dated Jun. 23, 2011.

Pekkanen-Mattila et al., "Substantial variation in the cardiac differentiation of human embryonic stem cell lines derived from propagated under the same conditions—a comparison of multiple cell lines," *Annals of Medicine*, 41:360-370, 2009.

Pucéat, "Protocols for cardiac differentiation of embryonic stem cells," *Methods*, 45:168-171, 2008.

Rao, "Conserved and divergent paths that regulate self-renewal in mouse and human embryonic stem cells," *Developmental Biology*, 275:269-286, 2004.

Reijo Pera et al., "Gene expression profiles of human inner cell mass cells and embryonic stem cells," *Differentiation*, 78:18-23, 2009.

Reubinoff et al., "Embryonic stem cell lines from human blastocysts: somatic differentiation in vitro," *Nature Biotechnology*, 18:399-404, 2000.

Sargent et al., "Cardiomyogenic differentiation of embryoid bodies is promoted by rotary orbital suspension culture," *Tissue Engineering: Part A*, 15(2):331-342, 2009.

(56) References Cited

OTHER PUBLICATIONS

Sato et al., "Molecular signature of human embryonic stem cells and its comparison with the mouse," *Developmental Biology*, 260:404-413, 2003.

Stevens et al., "Scaffold-free human cardiac tissue patch created from embryonic stem cells," *Tissue Engineering, Part A*, 15(6):1211-1222, 2009.

Takei et al., "Bone morphogenetic protein-4 promotes induction of cardiomyocytes from human embryonic stem cells in serum-based embryoid body development," *Am. J. Physiol. Heart Circ. Physiol.*, 296:H1793-H1803, 2009.

Thomson et al., "Embryonic stem cell lines derived from human blastocysts," *Science*, 282:1145-1147, 1998.

Ungrin et al., "Reproducible, ultra high-throughput formation of multicellular organization from single cell suspension-derived embryonic cell aggregates," *PLoS ONE.*, 3(2):e1565, Feb. 2008. 12 pages.

Uosaki et al., "Efficient and scalable purification of cardiomyocytes from human embryonic and induced pluripotent stem cells by VCAM1 surface expression," *PLoS ONE*, 6(8):e23657, 2011.

Van Berlo and Molkentin, "An emerging consensus on cardiac regeneration," *Nat Med.*, 20(12):1386-1393, 2014.

Watanabe et al., "A ROCK imhibitor permits survival of dissociated human embryonic stem cells," *Nat. Biotechnol.*, 25(6):681-6, 2007.

Xu et al., "Characterization and enrichment of cardiomyocytes derived from human embryonic stem cells," *Circulation Research*, 91:501-508, 2002.

Xu et al., "Highly enriched cardiomyocytes from human embyronic stem cells," *Cytotherapy*, 10(4):376-389, 2008. Abstract only.

Yajima et al., "Viral myocarditis: potential defense mechanisms within the cardiomyocyte against virus infection," *Future Microbiol.*, 6:551-566, 2011.

Yang et al., "Human cardiovascular progenitor cells develop from a $KDR^+$ embryonic-stem-cell-derived population," *Nature*, 453(7194):524-528, 2008.

Zandstra et al., "Scalable production of embryonic stem cell-derived cardiomyocytes," *Tissue Engineering*, 9(4):767-778, 2003.

Zhang et al., "[Differentiating into endothelioid cells from murine embryonic stem cell]," *Zhongguo Xiu Fu Chong Jian Wai Ke Za Zhi*, 23(1):82-86, 2009. (English abstract).

Zhang et al., "Functional cariomyocytes derived from human induced pluirpotent stem cells," *Circulation Research*, 104:e30-e41, 2009.

Lian et al., "Robust cardiomyocyte differentiation from human pluripotent stem cells via temporal modulation of canonical Wnt signaling," *Proc Natl Acad Sci USA*, 109(27):E1848-E1857, 2012.

Cruciat et al., "Secreted and transmembrane Wnt inhibitors and activators," *Cold Spring Harb Perspect Biol.*, 5:a015081, 2013.

Hong et al., "Applications of small molecule BMP inhibitors in physiology and disease," *Cytokine Growth Factor Rev.*, 20(5-6):409, 2009.

Office Action issued in European Application No. 17180891.8, dated Dec. 6, 2018.

Patani et al., "Activin/nodal inhibition alone accelerates highly efficient neural conversion from human embryonic stem cells and imposes a caudal positional identity," 4(10):e7327, 2009.

Rayasam et al., "Glycogen synthase kinase 3: more than a namesake," *British Journal of Pharmacology*, 156:885-898, 2009.

\* cited by examiner

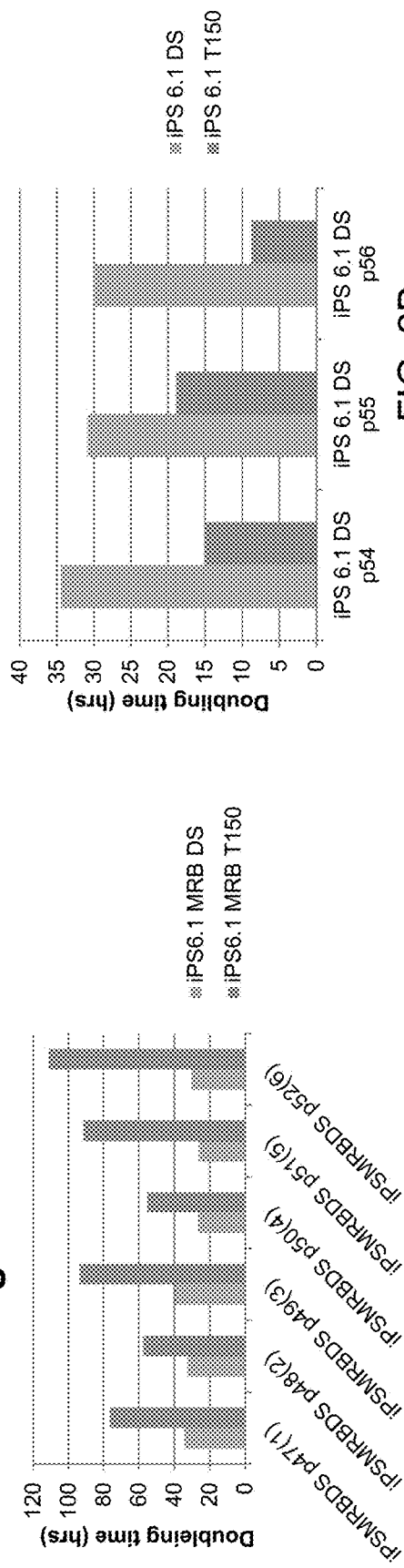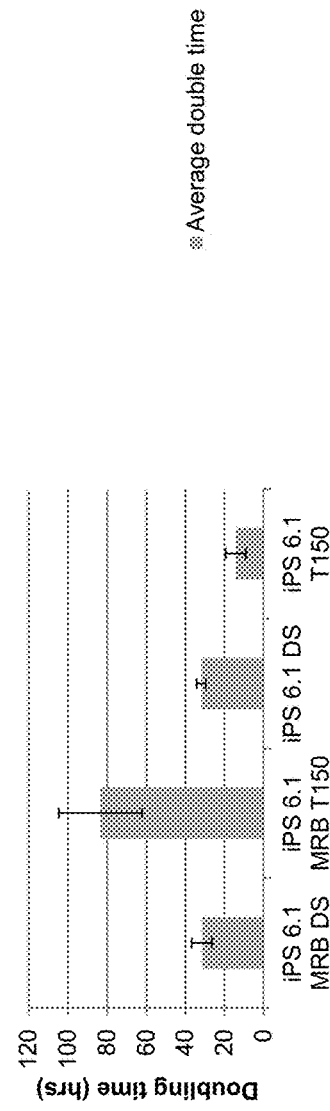
FIG. 2A
FIG. 2B
FIG. 2C
FIGs. 2A-C

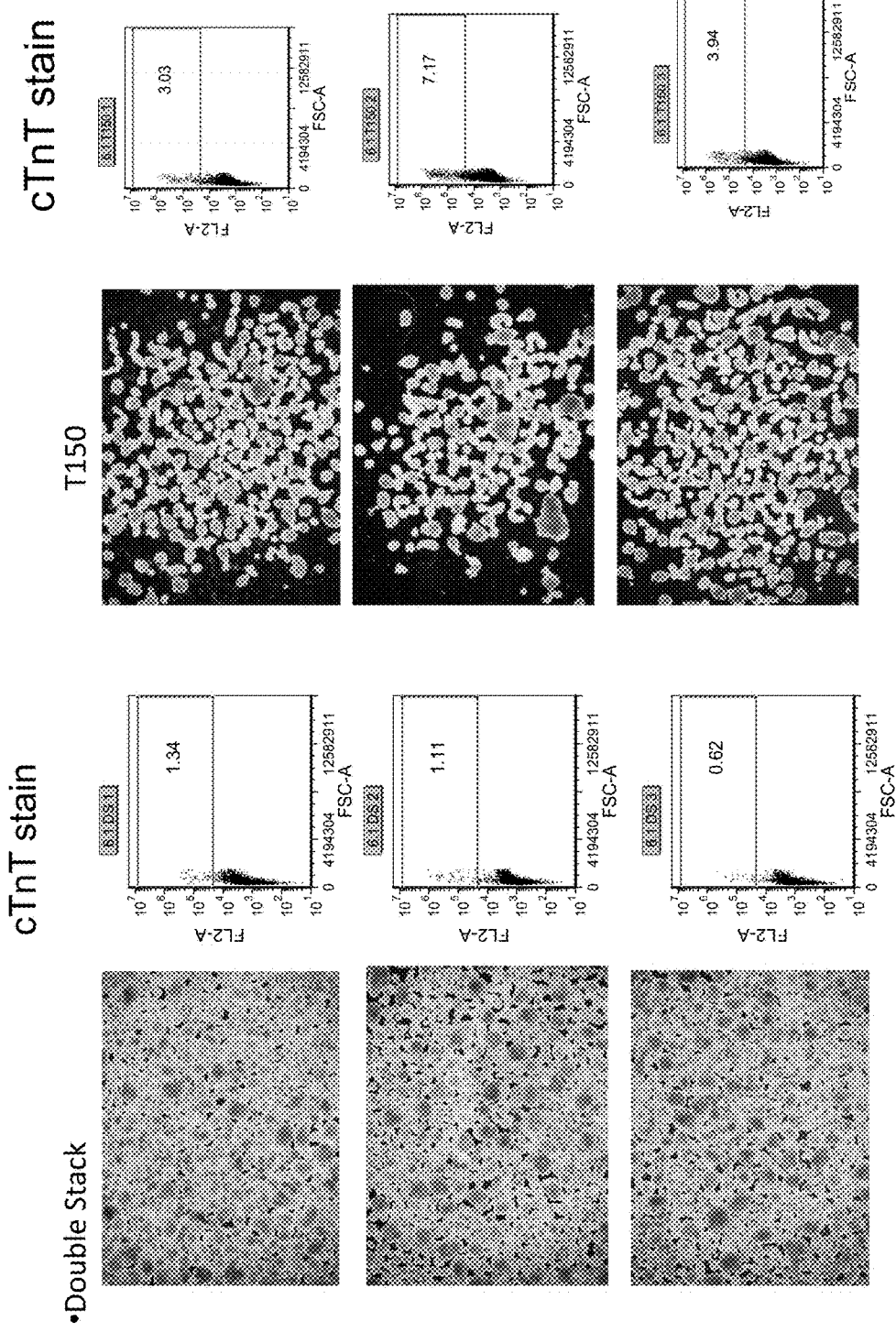
FIGs. 4A-D

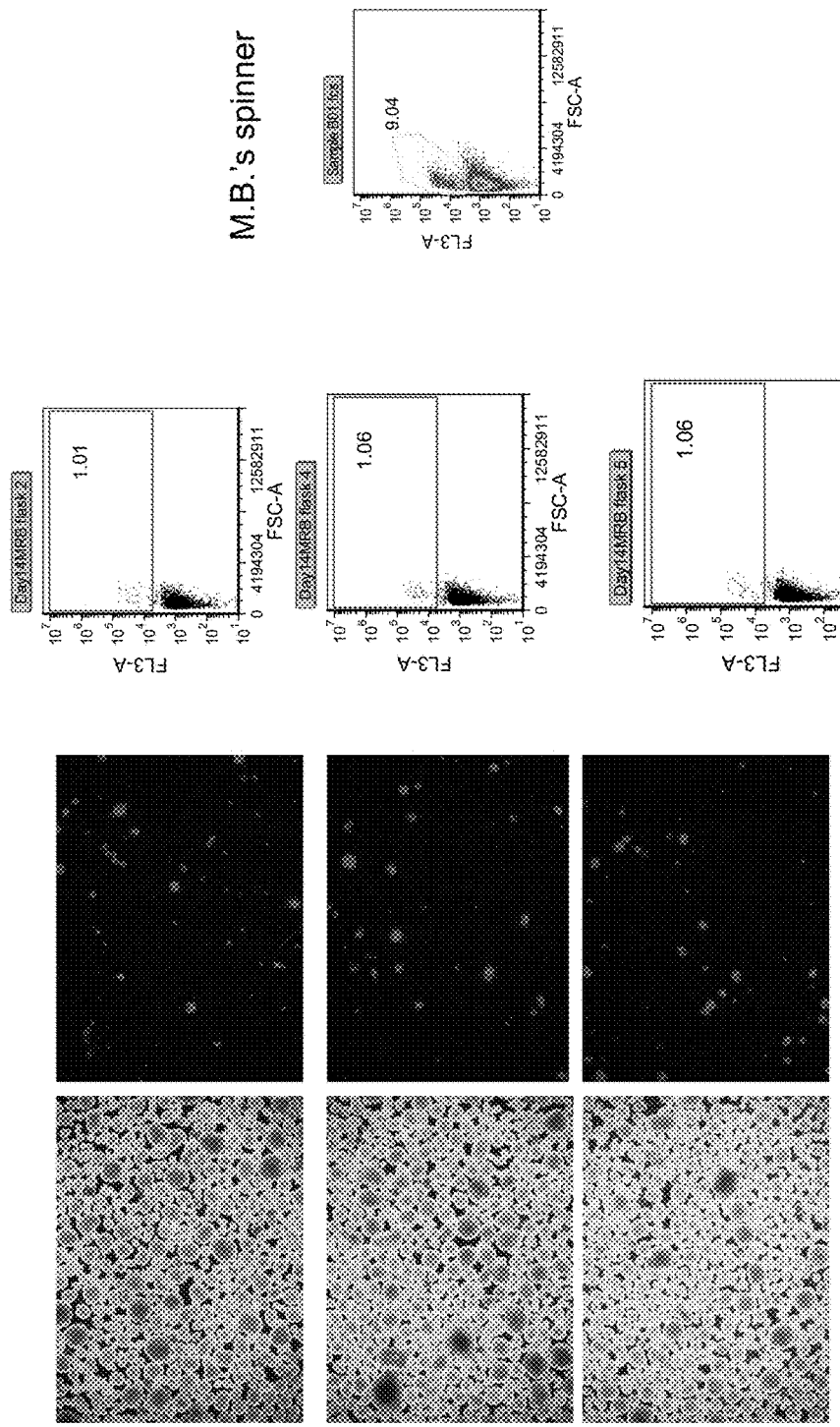
FIGs. 5A-C

FIGs. 6A-B

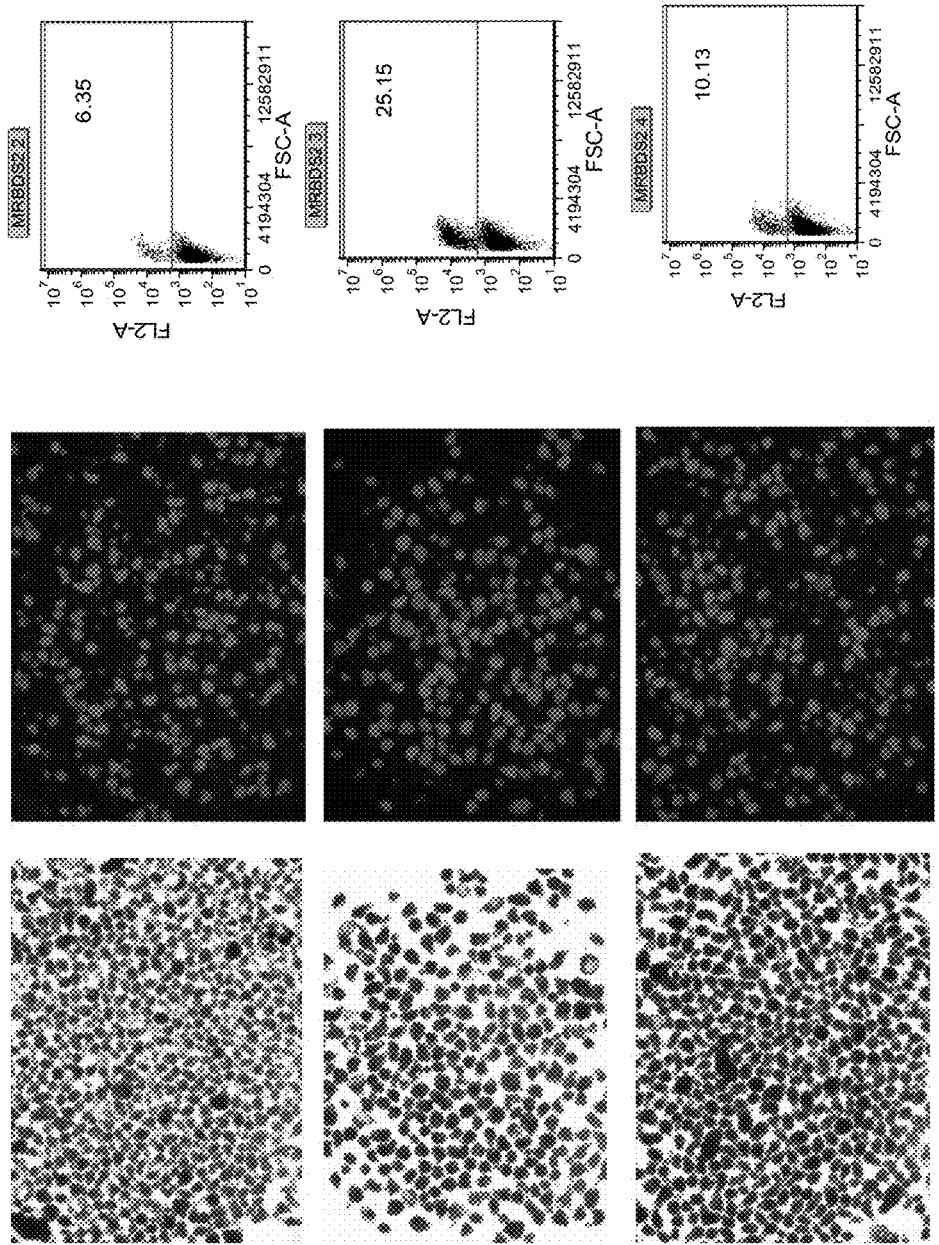
FIGs. 7A-C

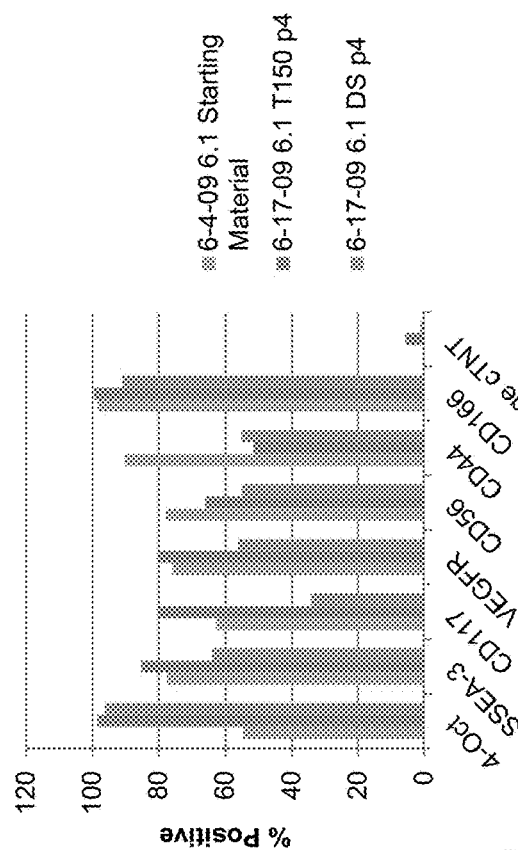
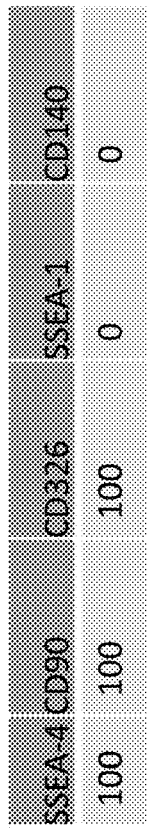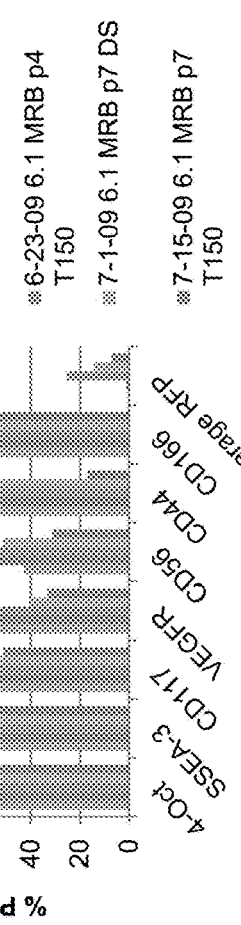
FIGs. 8A-C

| Flow Tube | Sample Id | initial Cells/ml | Initial Cells/Flask | Volume of sample | Final Cell Count (1E6) | %cTnT | Yeild cTnT (1E6) | IPS:cTnT | cTnT/L (1E6) | Average (1E6) | Standard Dev (1E6) | CV |
|---|---|---|---|---|---|---|---|---|---|---|---|---|
| 6.1 T150 | A | 1000000 | 5000000 | 5 | 0.41 | 2.7 | 0.011 | 452 | 2.2 | 5.2 | 2.7 | 0.523111 |
|  | B | 1000000 | 5000000 | 5 | 0.62 | 6.1 | 0.037 | 133 | 7.5 |  |  |  |
|  | C | 1000000 | 5000000 | 5 | 0.86 | 3.4 | 0.029 | 171 | 5.9 |  |  |  |
| 6.1 DS | A | 1000000 | 2500000 | 5 | 2.7 | 1.1 | 0.029 | 85 | 5.9 | 3.3 | 2.2 | 0.667761 |
|  | B | 1000000 | 2500000 | 5 | 0.91 | 1.1 | 0.01 | 249 | 2 |  |  |  |
|  | C | 1000000 | 2500000 | 5 | 2.1 | 0.5 | 0.01 | 242 | 2.1 |  |  |  |
| 6.1 MRBT150 | A | 1000000 | 2500000 | 5 | 4.4 | 22.1 | 1 | 3 | 195 | 177 | 15.9 | 0.08983 |
|  | B | 1000000 | 2500000 | 5 | 3.6 | 22.6 | 0.82 | 3 | 165 |  |  |  |
|  | C | 1000000 | 2500000 | 5 | 3.1 | 27.3 | 0.85 | 3 | 171 |  |  |  |
| 6/18/09 6.1 MRB DS | A | 1000000 | 2500000 | 5 | 5.6 | 1.5 | 0.083 | 30 | 16.7 | 13.6 | 2.7 | 0.199071 |
|  | B | 1000000 | 2500000 | 5 | 4.3 | 1.4 | 0.06 | 42 | 12 |  |  |  |
|  | C | 1000000 | 2500000 | 5 | 3.7 | 1.6 | 0.06 | 42 | 12 |  |  |  |
| 7/1/09 6.1 MRB DS 2nd | A | 1000000 | 2500000 | 5 | 9.7 | 6.7 | 0.65 | 4 | 129 | 126 | 20.7 | 0.165194 |
|  | B | 1000000 | 2500000 | 5 | 2 | 25.8 | 0.52 | 5 | 103 |  |  |  |
|  | C | 1000000 | 2500000 | 5 | 6.8 | 10.6 | 0.72 | 3 | 144 |  |  |  |
| 6.1 MRB T150 2nd | A | 1000000 | 2500000 | 5 | 5.1 | 6.3 | 0.32 | 8 | 64 | 67.5 | 11.5 | 0.170117 |
|  | B | 1000000 | 2500000 | 5 | 5.6 | 7.2 | 0.4 | 6 | 80 |  |  |  |
|  | C | 1000000 | 2500000 | 5 | 3.7 | 7.8 | 0.3 | 9 | 58 |  |  |  |
| 6/18/09 MB Spinner |  | 1000000 | 360000000 | 700 | 1200 | 9 | 108 | 3 | 154 |  |  |  |
| 6/26/09 MB Spinner |  | 1000000 | 450000000 | 900 | 730 | 11.8 | 86 | 5 | 96 |  |  |  |
| 7/1/09 MB Spinner |  | 1000000 | 500000000 | 1000 | 600 | 13.3 | 80 | 6 | 80 |  |  |  |

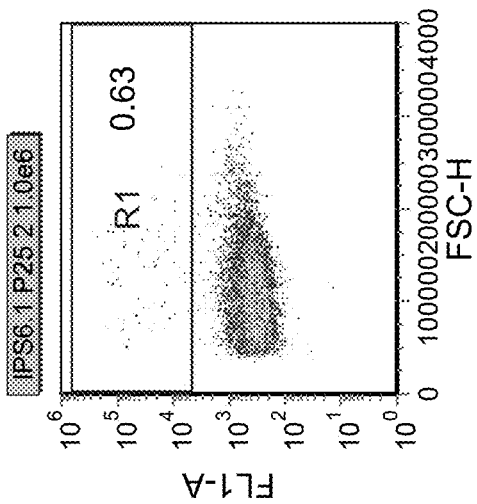
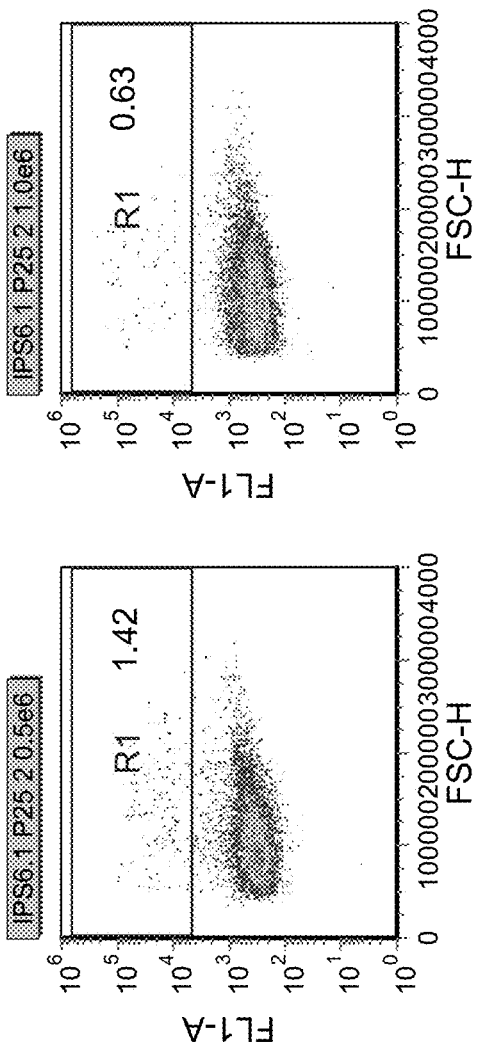
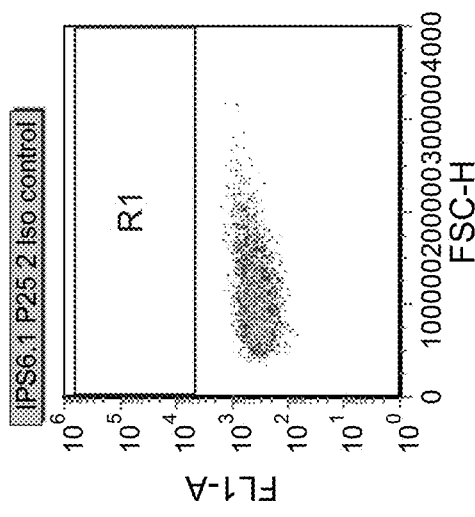
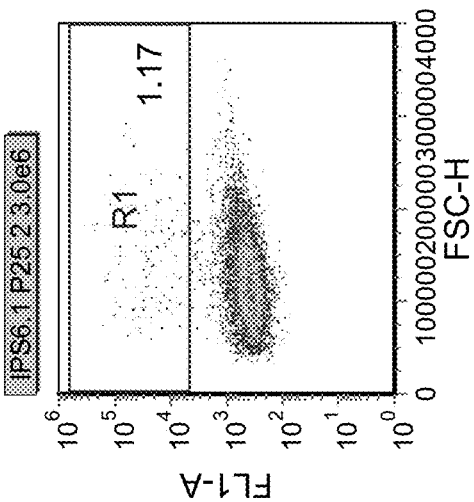
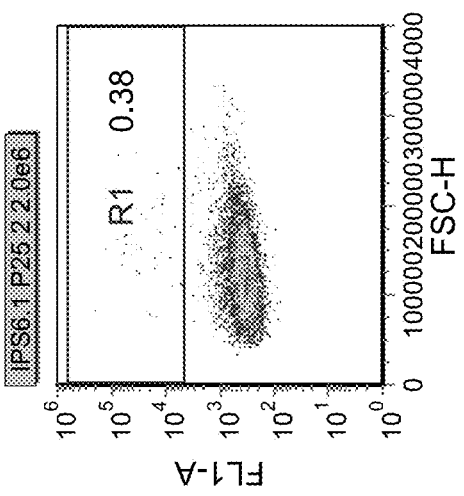
FIGS. 14A-E

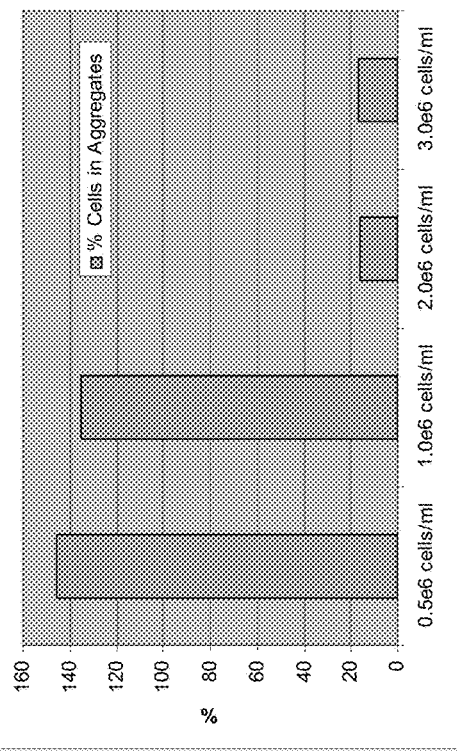
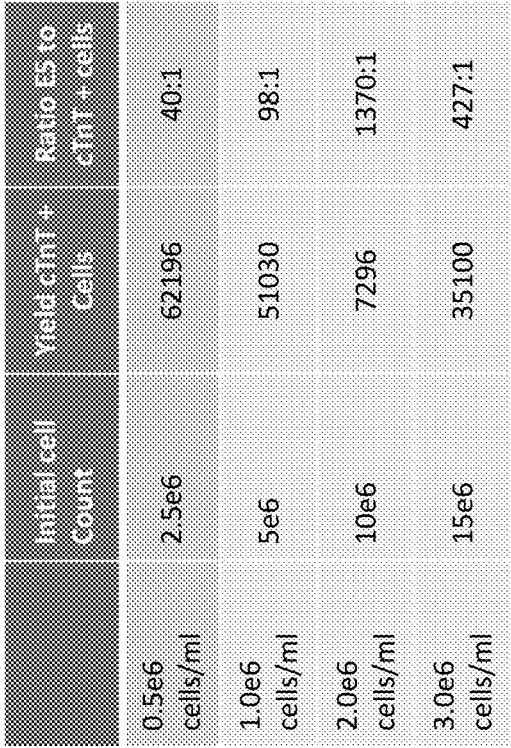
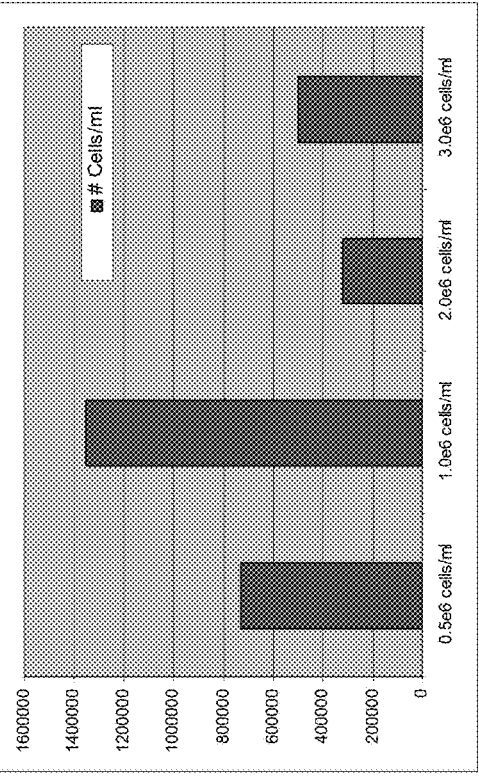
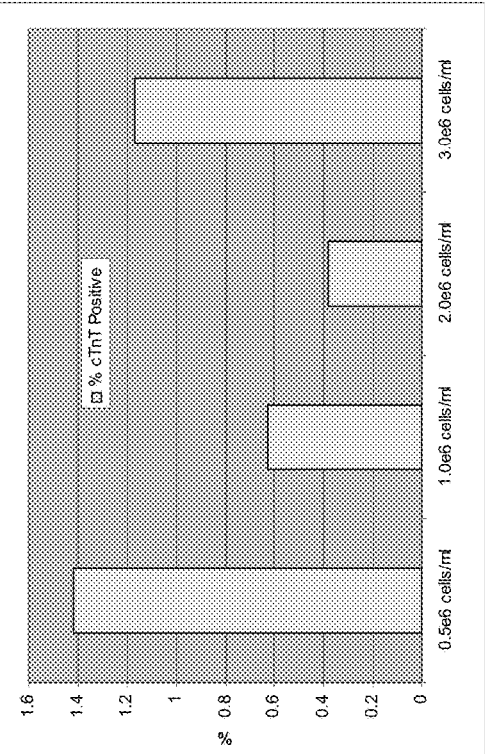
FIGs. 15A-D

FIGs. 16A-C

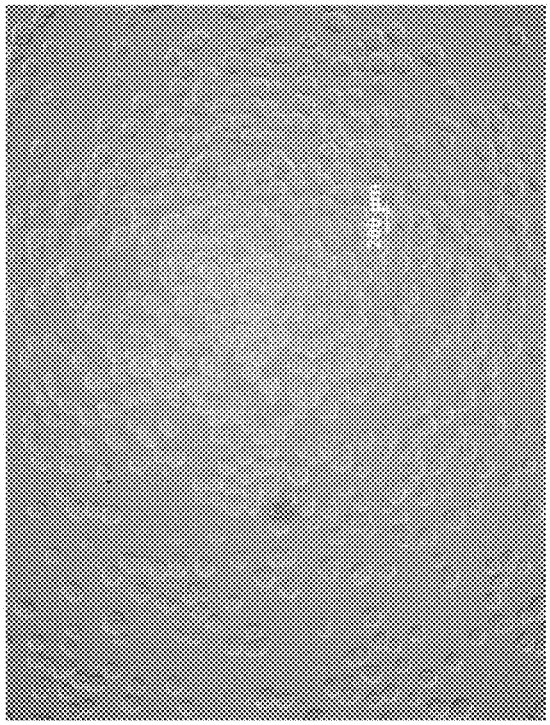
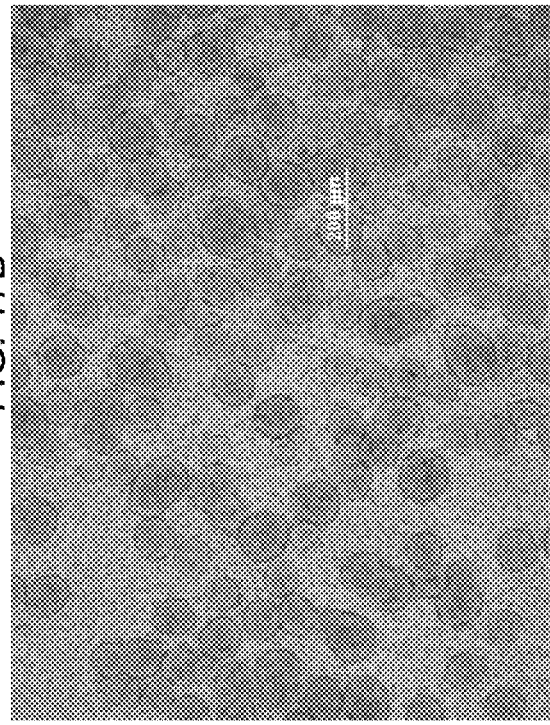
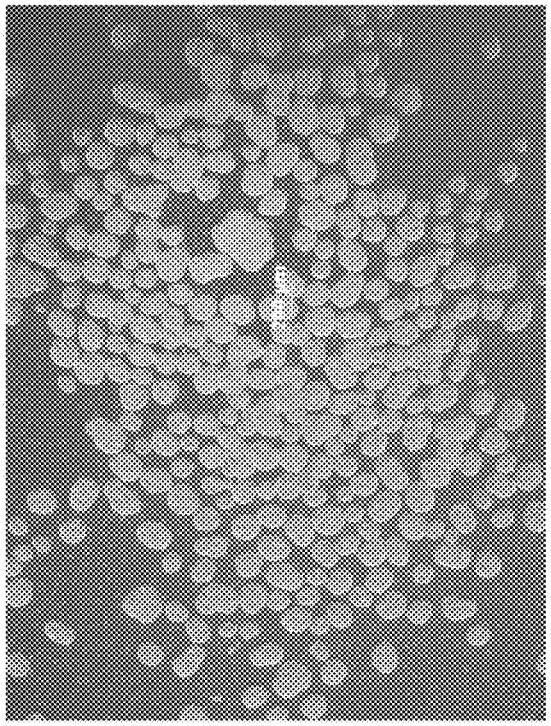
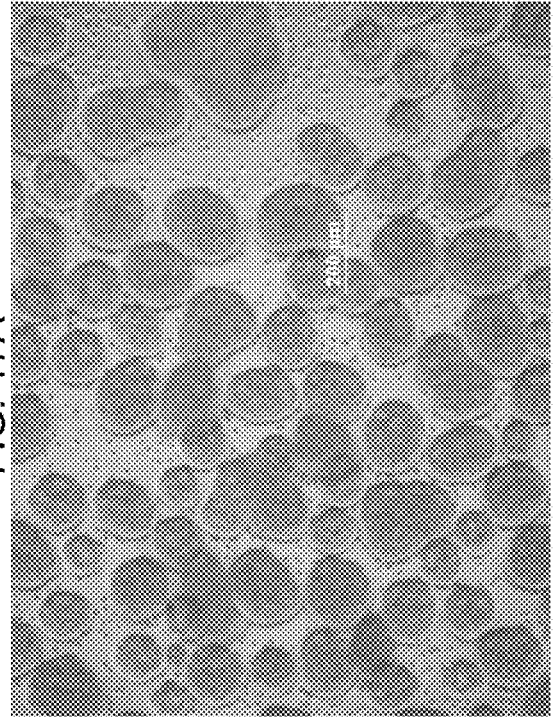
FIG. 17A
FIG. 17B
FIG. 17C
FIG. 17D
FIGs. 17A-D

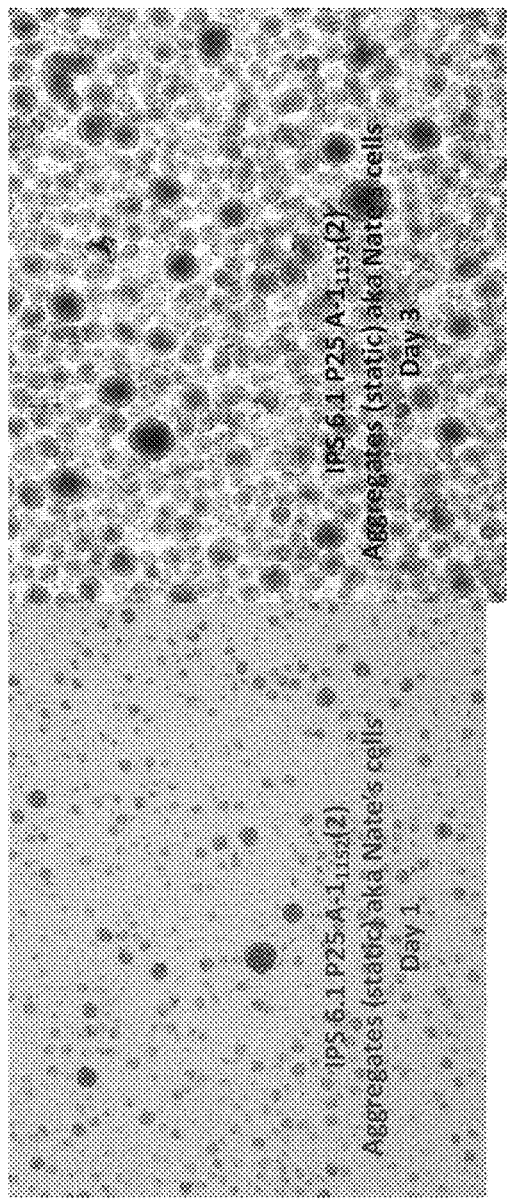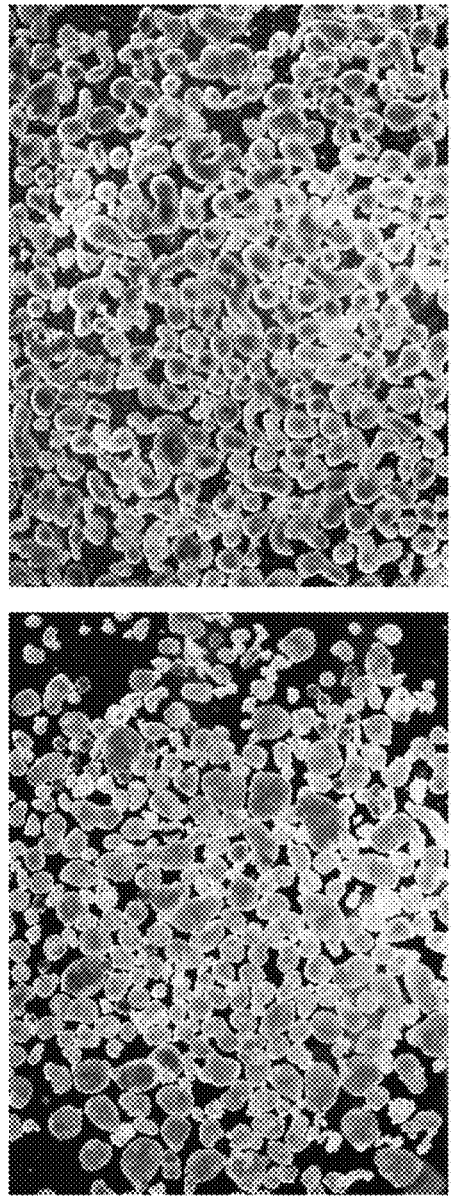
FIG. 20

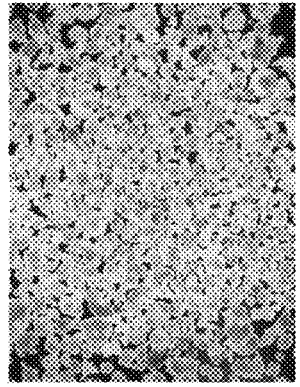 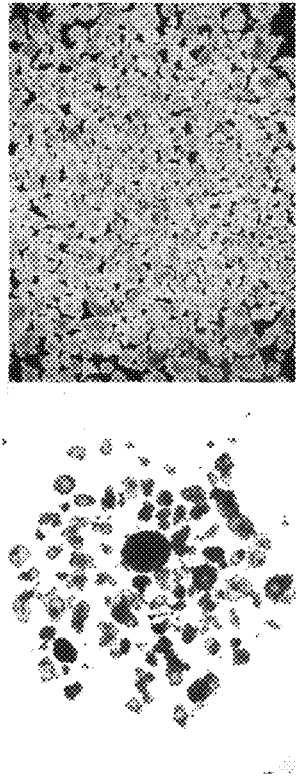 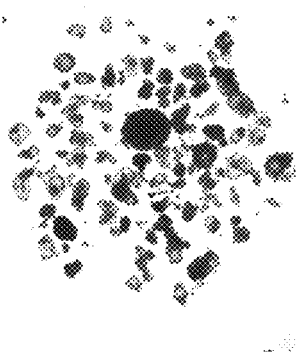 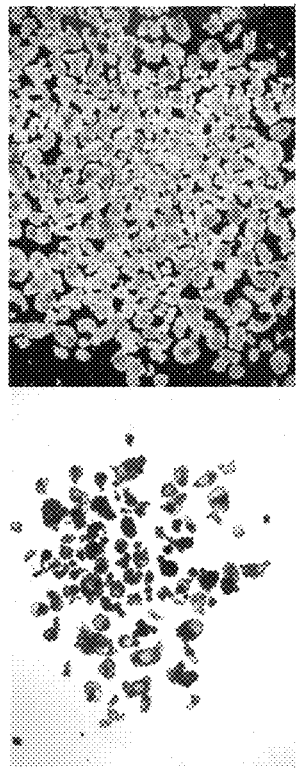 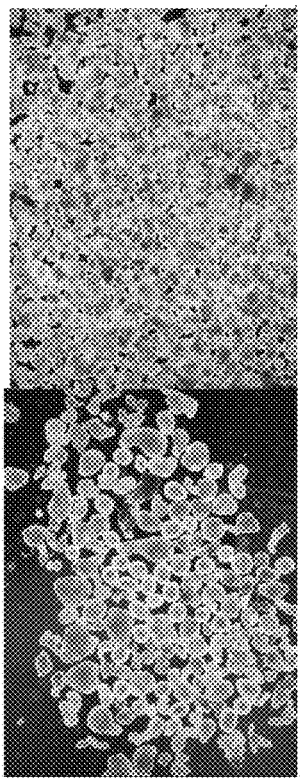 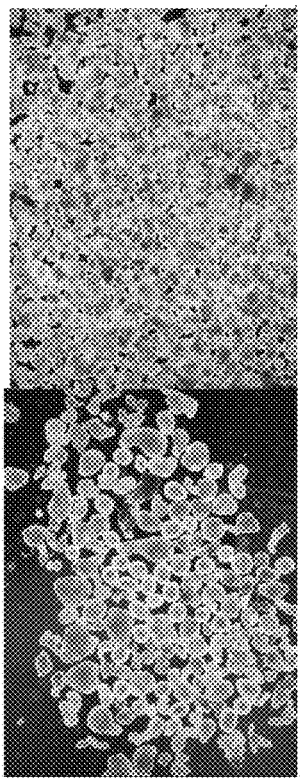 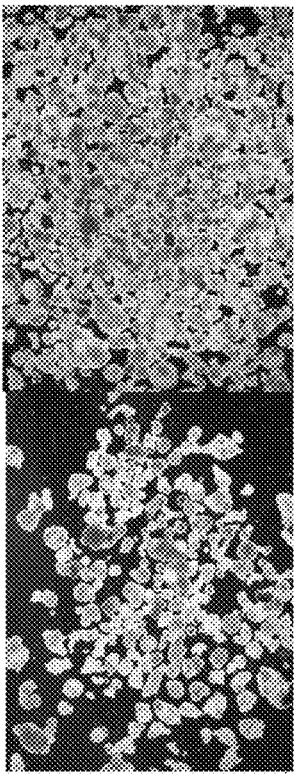 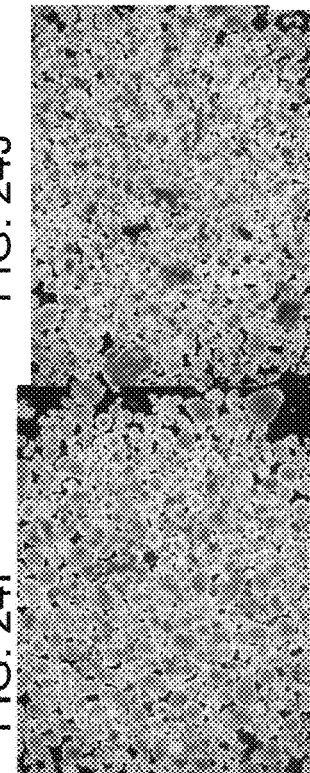 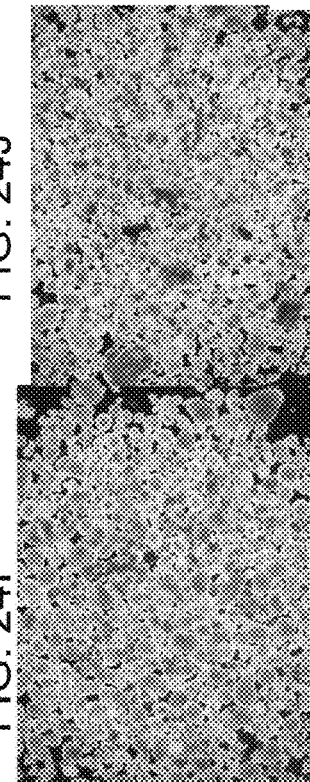
FIGs. 24A-J

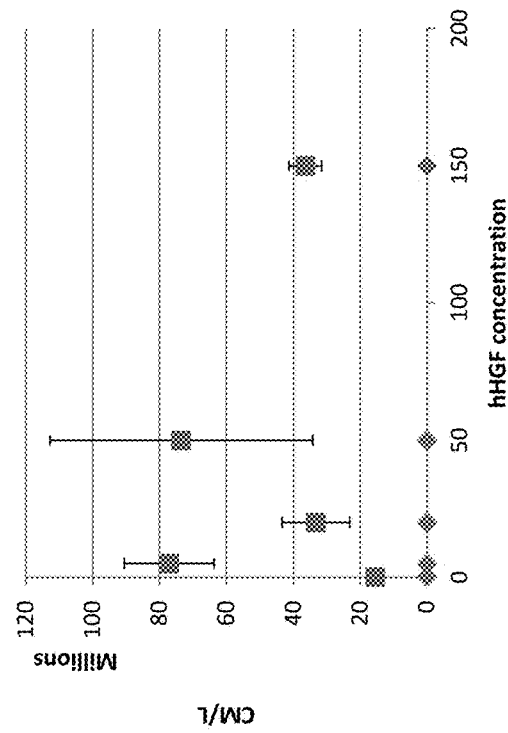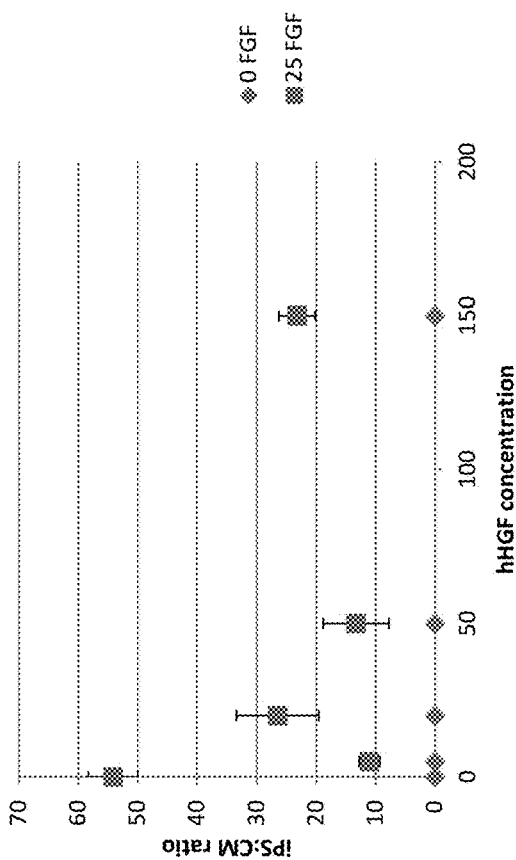
FIG. 29B
FIG. 29A
FIGs. 29A-B

FIGs. 30A-B

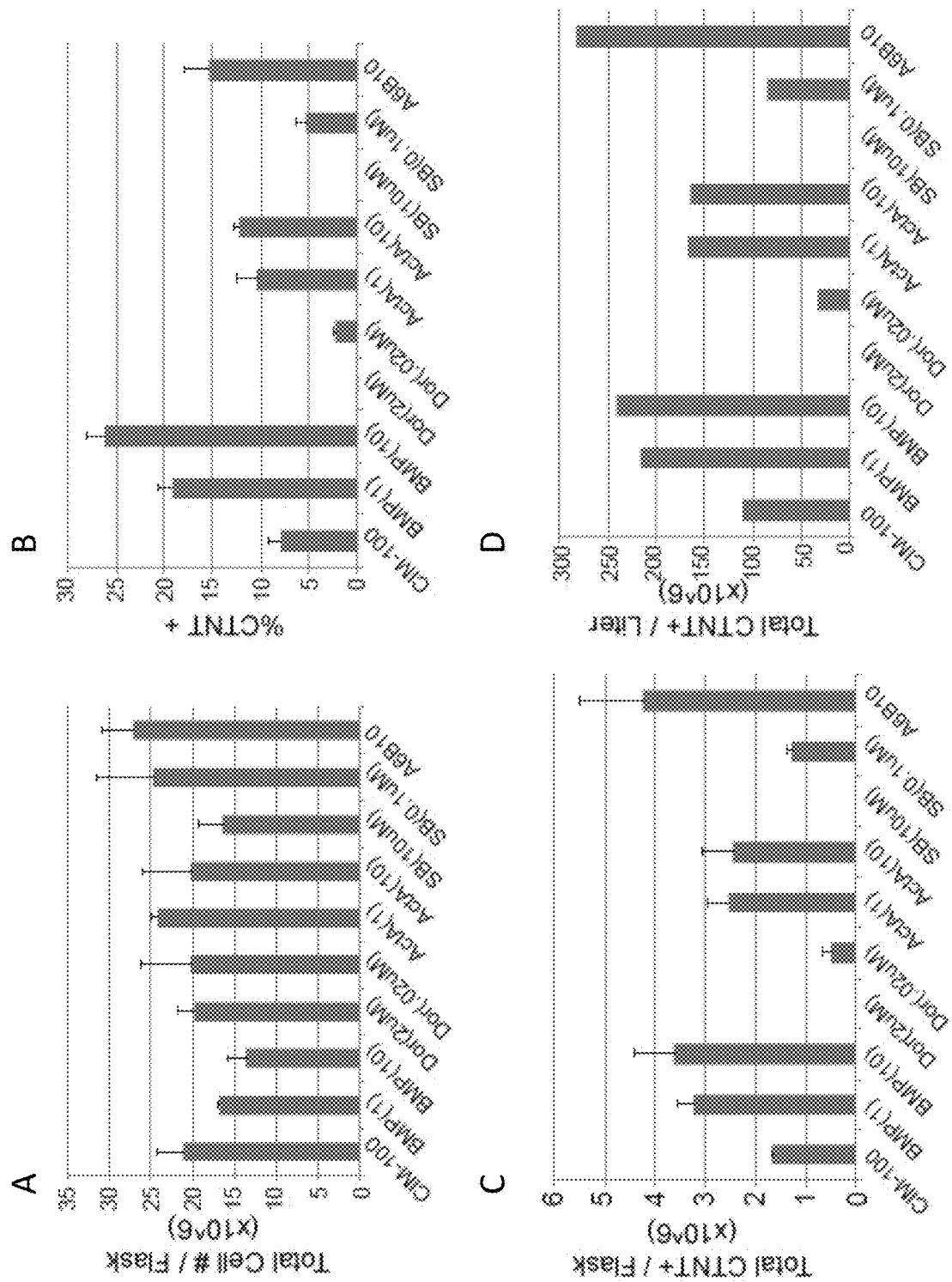
FIGs. 33A-D

CARDIOMYOCYTE PRODUCTION

The present application is a divisional of U.S. application Ser. No. 14/665,616, filed Mar. 23, 2015, which is a continuation of U.S. application Ser. No. 13/794,679, filed Mar. 11, 2013, now abandoned, which is a divisional of U.S. application Ser. No. 12/907,714, filed Oct. 19, 2010, now U.S. Pat. No. 8,415,155, issued Apr. 9, 2013, which claims the priority benefit of U.S. Provisional Application No. 61/252,919, filed Oct. 19, 2009. The subject matter of this application also relates to that of U.S. Provisional Application No. 61/394,589 filed on Oct. 19, 2010. The entire text of each of the above referenced disclosures is specifically incorporated herein by reference.

BACKGROUND OF THE INVENTION

1. Field of the Invention

The present invention relates generally to the field of stem cell development. More particularly, it concerns the induction of cardiomyocyte differentiation from pluripotent stem cells.

2. Description of Related Art

Cardiomyocytes are thought to be terminally differentiated. Although a small percentage of cardiomyocytes may have proliferative capacity, this is not sufficient to adequately replace injured or dead cardiomyocytes. Death of cardiomyocytes occurs, for example, when a coronary vessel is occluded by a thrombus and the surrounding cardiomyocytes cannot be supplied with necessary energy sources from other coronary vessels. Loss of functional cardiomyocytes may lead to chronic heart failure.

The proliferative capacity of the cardiomyocytes is not sufficient to regenerate the heart following myocardial injury. Conventional pharmacological therapy for patients with different stages of ischemic heart disease improves cardiac function, survival and quality of life. However, ischemic heart disease is still the most life-threatening disease in the United States and Europe; accordingly, alternative therapies will be necessary to improve the clinical outcome for patients with ischemic heart disease further. In recent years, the focus on cell replacement therapy has been intensified, stimulated by the increasing number of potential cell sources for transplantation, such as skeletal myoblasts, adult cardiac stem cells, bone marrow stem cells and embryonic stem cells.

A potential route for restoring "normal" heart function is replacement of injured or dead cardiomyocytes by new functional cardiomyocytes. Pluripotent stem cells, such as human embryonic stem (ES) cells or induced pluripotent stem cells (iPS) cells, are a potential source of cells for cardiomyocyte replacement. Differentiation of pluripotent stem cells into cardiomyocytes can be achieved either spontaneously or upon induction.

However, a number of obstacles have stood in the way of developing a paradigm for obtaining substantially enriched populations of cardiomyocyte lineage cells from pluripotent stem cells. Some ensue from the relative fragility of pluripotent cells of primate origin, the difficulty in culturing them, their exquisite sensitivity and dependence on various factors present in the culture environment, and low efficiency and wide variation of differentiation methods. Thus, there is a need to improve induction of differentiation of pluripotent stem cells to cardiomyocytes, especially for large-scale production.

SUMMARY OF THE INVENTION

The present embodiments overcome a major deficiency in the art by providing methods for differentiating pluripotent stem cells into cardiomyocytes, especially for large scale and high efficiency production to meet the needs in clinical applications.

Procedures for differentiating pluripotent stem cells preferably employ culture conditions that attempt to mimic the in vivo environment driving the development of a particular lineage, such as by the addition of specific growth factors. When differentiated in vitro, a number of sources contribute to the growth factor environment, including: 1) endogenous expression from the cells themselves, 2) the sera and/or media (non-limiting examples include TeSR, mTeSR, RPMI medium, supplemented DMEM-F12 or dilutions thereof) that the pluripotent stem cells are cultured and/or subsequently differentiated in, and 3) the addition of exogenous growth factors. In regard to the endogenous expression of growth factors, the inventors have recognized a clone-to-clone variability as well as variability due to differences in the primary culture of the cells. Furthermore, the inventors have determined that there exists (sometimes dramatic) batch-to-batch variability in the growth factor content of the culture medium used in culturing and differentiation of pluripotent stem cells, both introducing unpredictability to cell lineage differentiation.

In order to address the foregoing variability in pluripotent stem cell differentiation procedures, the present inventors have developed a technique which accounts for all the sources contributing to the growth factor environment in a given differentiation culture, which are independently "balanced" for each batch or lot of medium and for each individual stem cell clone that is employed, in order to achieve an optimal differentiation. This may be achieved by the addition of differentiation factors to modulate developmental signaling pathways. Examples include: 1) the addition of antagonists to reduce the total signal in certain pathways, 2) the addition of agonists to increase the total signal of certain pathways or 3) combinations of agonists and or antagonists to optimize the signal.

For increased production of cardiomyocytes, there is provided a method comprising incubating pluripotent stem cells from a selected cell line in a suspension culture under conditions to promote aggregate formation; and differentiating the stem cells into cardiomyocytes in a cardiac differentiation medium prepared from a selected batch of culture medium. For example, the culture medium is TeSR, mTeSR or RPMI medium supplemented DMEM-F12 or dilutions thereof. In the case of cardiomyocyte differentiation, and without wishing to be bound by theory, it is contemplated that TGFβ signaling pathways may be delicately regulated by adjusting the external addition of certain growth factors to achieve optimal cardiac differentiation condition. In particular, BMP signaling and Activin signaling are two exemplary TGFβ signaling pathways that can be optimized for the particular batch of medium and pluripotent cell clone (e.g., from an iPS line) employed. The relative activity ratio between the two signaling pathways may be important for the optimal cardiomyocyte differentiation condition. Thus, differentiation factors may include positive modulators or inhibitors of BMP signaling and/or Activin signaling. For example, BMP signaling inhibitor comprises dorsomorphin and Activin signaling inhibitor comprises SB431542.

Thus, in accordance with some aspects of the present invention, the cardiac differentiation medium is prepared from the culture medium by adjusting the level of one or more differentiation factors in the culture medium at amounts determined to be appropriate for cardiac differentiation of the selected cell clone or line and culture media batch employed. In particular aspects, the selected cell clone is an induced pluripotent stem (iPS) cell clone. Described herein below (Example 8) is an exemplary procedure for separately determining the appropriate amount of growth factors that should be added for any given medium batch and pluripotent cell clone employed. Once the adjustment is determined for the particular medium batch and cell clone, the adjustment is incorporated into the differentiation procedure, providing a highly reproducible differentiation procedure tailored for each batch and clone.

The selected cell clone is typically derived from a single pluripotent stem cell in an adherent culture or a suspension culture. For example, it is preferred that the selected cell clone be derived from a single pluripotent stem cell by a process comprising incubating the single pluripotent stem cell in medium comprising, for example, a Rho-associated kinase (ROCK) inhibitor or a myosin II inhibitor under conditions to promote cell growth. Such a myosin II inhibitor may be blebbistatin. The starting number of pluripotent stem cells may be about, at least or at most $10^5$, $10^6$, $10^7$, $10^8$, $10^9$, $10^{10}$ cells or any range derivable therein.

In certain aspects, the conditions to promote aggregate formation comprises externally added ROCK inhibitor, myosin II inhibitor, fibroblast growth factor (FGF) or hepatic growth factor (HGF). The aggregate formed from the pluripotent stem cells may be about, at least or at most 5, 10, 15, 20, 25, 30, 50, 100, 150, 200, 250, 300, 350, 400, 450, 500 μm in diameter. The diameter may be a mean, median or average diameter. The suspension culture may have a volume of about, at least or at most 2 ml, 5 ml, 10 ml, 20 ml, 30 ml, 40 ml, 50 ml, 100 ml, 200 ml, 500 ml, 1 liters, 3 liters, 5 liters, 10 liters, 20 liters, 25 liters, 30, liters, 40 liters, 50 liters, or any range derivable therein, such as in a bioreactor.

The cardiac differentiation medium may also comprise externally adjusted fibroblast growth factor (FGF), hepatocyte growth factor or any differentiation factors that to be used or screened. Such FGF, HGF, or other differentiation factor like TGFβ signaling modulators may be at an amount of at least, about or at most 0.1, 1, 5, 10, 15, 20, 25, 30, 35, 40, 45, 50, 55, 60, 65, 70, 75, 80, 90, 100, 150, 200 ng/ml or any range derivable therein.

For selection or enrichment of desired cells, the pluripotent stem cells and/or cardiomyocytes differentiated therefrom may contain one or more transgenes. For example, the one or more transgenes encode a selectable and/or screenable marker under the control of a cardiomyocyte-specific promoter. The method may further comprise enriching or purifying the differentiated cardiomyocytes.

In certain aspects, the differentiation factors whose level is adjusted in the culture medium comprise one or more of modulators of signaling pathways of bone morphogenetic protein, ActivinA/Nodal, vascular endothelial growth factor (VEGF), dickkopf homolog 1 (DKK1), basic fibroblast growth factor (bFGF), insulin growth factor (IGF), and/or epidermal growth factor (EGF). For example, the differentiation factors may comprise BMP2, BMP4, BMP10, Activin A, bFGF, IGF, EGF, BMP signaling inhibitor, Activin signaling inhibitor, or a combination thereof. In particular, the BMP signaling inhibitor may comprise dorsomorphin; the Activin A signaling inhibitor may comprise SB431542.

In certain aspects, the differentiation medium may have been prepared from the selected batch of culture medium by adjusting the amounts of addition of one or more differentiation factors, such as for differentiation of cardiomyocytes. In further aspects, the differentiation medium may have been prepared from the selected batch of culture medium by adjusting the timing of addition of one or more differentiation factors, such as for differentiation of cardiomyocytes as well.

There may provided a method involving separately determining the appropriate amount and/or timing of growth factors that should be added for any given medium batch and pluripotent cell clone employed. Once the adjustment is determined for the particular medium batch and cell clone, the adjustment is incorporated into the differentiation procedure, providing a highly reproducible differentiation procedure tailored for each batch and clone.

In certain aspects, the method may comprise determining amounts of addition of one or more differentiation factors appropriate for differentiation into selected lineages, such as cardiomyocytes. This determination may comprise testing differentiation of cells from the selected clone in a culture medium from the selected batch added with varied amounts of differentiation factors during a test period. For example, varied amounts of differentiation factors may be added during a test period. The test period may be the same or varied for a test condition with a specific concentration of differentiation factors. For example, the test period may start from about 1, 2, 3, 4, 5, 6, 7 prior to differentiation or day 1, 2, 3, 4, 5 after differentiation, and end on day 6, 7, 8, 9, 10, 11, 12, or 13 after differentiation (any intermediate time period may also be included). The same concentration of differentiation factors may be changed daily or every 2, 4, 8, 16, 24, 48 hours or any intermediate intervals.

Such varied amounts of differentiation factors may include conditions with varied ratios of BMP/Activin signaling activity. This may be achieved by varying amounts of BMP, Activin, BMP signaling inhibitor, and/or Activin signaling inhibitor. For example, this variation may include one or more of the following varying conditions: varied concentrations of BMP4 alone, varied concentration of Activin A alone, varied concentration of BMP signaling inhibitor, varied concentration of Activin signaling inhibitor, and varied concentration of combination of BMP4 and Activin A.

To determine the appropriate cardiomyocyte differentiation condition, the testing may further comprise measuring mesoderm or cardiomyocyte differentiation efficiency for each condition and selecting the condition with the highest differentiation efficiency as being appropriate for the differentiation of the selected pluripotent stem cell clone into cardiomyocytes and selected batch of culture media employed. The measurement of differentiation efficiency may comprise measuring mesoderm marker expression at least or about days 5, 6, 7, 8, 9, 10, 11, 12, 13 after differentiation or any intermediate time range. Non-limiting examples of mesoderm markers include KDR, PDGFR-a, CXCR4, CKIT$^{negative}$, N-Cadherin, and/or MESP1. In other aspects, the measurement of differentiation efficiency may comprise measuring differentiation efficiency comprises measuring cardiomyocyte marker expression at about or at least day 14 after differentiation. After selection of the appropriate condition, the method may comprise differentiating the stem cells into cardiomyocytes in a differentiation medium prepared from a selected batch of culture medium, wherein the differentiation medium has been prepared from the selected batch of culture medium under the selected condition during the test period.

There may be also provided an isolated cell population of at least or about $10^6$, $10^7$, $10^8$, $5\times10^8$, $10^9$, $10^{10}$ cells (or any range derivable therein) comprising at least or about 90%

(for example, at least or about 90%, 95%, 96%, 97%, 98%, 99%, 99.5%, or any range derivable therein) cardiomyocytes.

In a certain embodiment, there may be provided methods for increased production of cardiomyocytes comprising: a) incubating pluripotent stem cells in a suspension culture under conditions to promote aggregate formation, wherein the suspension culture comprises aggregate promotion medium; and b) then differentiating the stem cells into cardiomyocytes in a suspension culture suitable for cardiac differentiation. For example, the suspension culture suitable for cardiac differentiation may have a volume greater than 5 milliliters. The aggregate promotion medium may contain a Rho-associated (ROCK) inhibitor, In certain aspects, a ROCK inhibitor may be a ROCK-specific inhibitor.

The term "increased production" may refer to an increase in the absolute number of cells or it may refer to an increase in the percentage of cardiomyocytes compared to non-cardiomyocyte cells, or both, unless otherwise indicated. It is contemplated that methods may concern an increase in the absolute number of cardiomyocytes in some embodiments. In other embodiments, methods may concern an increase in the percentage of cardiomyocytes. In further embodiments, there may be an increase in both absolute number and percentage of cardiomyocytes.

In a further aspect, the method further comprises: c) pooling multiple suspension cultures after aggregate formation and/or after differentiation; and d) enriching for cardiomyocytes.

In some embodiments, methods result in a cell population of at least or about $10^7$, $10^8$, $10^9$, or up to about $10^{10}$ cells (or any range derivable therein) comprising at least 5%, 10%, 15%, 20%, 30%, 40%, 50%, 60%, 70%, 80%, 90% cardiomyocytes, or any percentage derivable therein.

In another embodiment, there are methods for preparing cardiomyocytes comprising: a) obtaining a pluripotent stem cell population comprising pluripotent stem cell aggregates; and b) incubating the pluripotent stem cells in a suspension culture comprising cardiac induction medium (also called CIM) to differentiate the stem cells into cardiomyocytes. The cardiac induction medium may include one or more cardiac induction agents effective to differentiate the stem cells into cardiomyocytes, such as fibroblast growth factor (FGF). The methods are particularly suited for large scale production of cardiomyocytes. Pluripotent stem cell aggregates may be formed in a suspension culture, which may be between about 0.5 ml and about 25 liters, such as in a bioreactor. Some embodiments involve cells growing in a space whose volume is larger than a standard petri dish or 96-well plate; consequently, some embodiments exclude the use of such containers.

In certain embodiments of the invention, large scale production of cardiomyocytes may be implemented. "Large scale," as used herein, refers to the use of a cell culture of a volume of at least 500 ml with a concentration of at least $1.0 \times 10^6$ cells/ml. The volume may be at least or about 500 ml, 600 ml, 700 ml, 800 ml, 1 liter, 2 liters, 3 liters, 5 liters, 10 liters, 20 liters, or up to 25 liters, or any range derivable therein, such as in a bioreactor. Cell concentration in suspension culture may be at least or about $10^6$, $10^7$, $10^8$, $10^9$, $10^{10}$ cells/ml, or any range derivable therein. Cells may be manipulated subsequent to production, such as by concentrating them and/or reducing the cell culture volume.

In certain aspects, for large scale production of cardiomyocytes, the suspension culture may be moved at a speed of at least or about 10, 15, 20, 30, 35, 40, 45, 50, 55, 60, 65, 70, 75, 80, 85, 90, 100, 150, 200, 250, 300 rpm, or any range of speed derivable therein. The movement may comprise stirring, shaking, or rotating as non-limiting examples.

The pluripotent stem cells may comprise one or more transgenes; for example, any steps of the methods may be performed under conditions to select for transgenic cells. In a further aspect, the cardiomyocytes may be also incubated in a cardiac maintenance media that lacks added FGF. Steps of the invention, such as step b) described above, may last for at least 1, 2, 3, 4, 5, 6 days, 1, 2, 3, 4, 5, 6, 7, 8, 9, 10, 11, 12, 13, 14, 15 weeks, or up to 106 days, or any time range derivable therein. In a further aspect, the method further comprises: c) pooling multiple suspension cultures after aggregate formation and/or after differentiation; and d) enriching for cardiomyocytes. In some embodiments, methods result in a cell population of at least or about $10^7$, $10^8$, $10^9$, or up to about $10^{10}$ cells (or any range derivable therein) comprising cardiomyocytes of at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% (or any range derivable therein).

Other embodiments concern methods for preparing cardiomyocytes comprising: a) growing a population of transgenic iPS cells in a suspension culture of more than 5 milliliters comprising aggregate promotion medium that includes a ROCK inhibitor and FGF under conditions that promote aggregate formation; and b) then differentiating the iPS cells into cardiomyocytes in a suspension culture comprising cardiac induction medium that includes FGF under conditions to promote cardiomyocyte differentiation. In certain aspects, the population of transgenic iPS cells may be clonally derived from a single transgenic iPS cell. In a further aspect, a cell population of at least or about $10^7$, $10^8$, $10^9$, or up to about $10^{10}$ cells (or any range derivable therein) comprising at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% (or any range derivable therein) cardiomyocytes produced by the method described above, wherein the method further comprises: c) pooling multiple suspension cultures after aggregate formation and/or after differentiation; and d) enriching for cardiomyocytes.

In certain further embodiments, methods involve pluripotent stem cells as starting material for cardiomyocyte production or preparation, which could be embryonic stem (ES) cells, induced pluripotent stem cells, or embryonic stem cells derived by somatic cell nuclear transfer. In a certain aspect, the pluripotent stem cells may be clonally derived from a single pluripotent stem cell, may comprise a substantial portion of cells clonally derived from a single cell, or may be a pool of multiple populations of cells, wherein each population of cells is clonally derived from a single cell. An exemplary process for obtaining pluripotent stem cells from a single cell may comprise incubating a single pluripotent stem cell in medium comprising a ROCK inhibitor under conditions to promote cell growth, such as being incubated under adherent culture conditions. Prior to growing the pluripotent stem cells in the suspension culture for aggregate formation in the step a), the single pluripotent stem cell as the originating source may be passaged once, twice, three times, four times, or preferably at least five times. In another aspect, the pluripotent stem cells may also be derived from an iPS cell population comprising more than a single cell.

In still further aspects, about $10^7$ to about $10^{10}$ of the pluripotent stem cells may be first incubated in the suspension culture in step a) for aggregate formation. The pluripotent stem cell aggregates may be formed by incubating pluripotent stem cells with aggregate promotion medium comprising a ROCK inhibitor, which may be about 0.05 to about 5 µM, for example, at least or about 0.05, 0.1, 0.2, 0.5, 0.8, 1, 1.5, 2, 2.5, 5 µM, or any concentration effective for promoting cell growth or survival, including any range derivable therein.

In certain aspects, a culture medium, such as the aggregate promotion medium, may comprise fibroblast growth factor (FGF), for example at a concentration of about 5 to 200 ng/ml, such as at least or about 10, 15, 20, 25, 30, 35, 40, 45, 50, 55, 60, 65, 70, 75, 80, 85, 90, 95, 100, 150, 180, 200 ng/ml, or any range derivable therein. Optionally hepatic growth factor (HGF) may also be included, for example at a concentration of at least or about 25, 30, 35, 40, 45, 50, 55, 60, 65, 70, 75, 80, 85, 90, 95, 100, 150, 180, 200 ng/ml, or any range derivable therein.

The aggregate promotion medium may further comprise an antibiotic, such as zeocin, which may be used for cardiomyocyte enrichment or selection. The aggregates formed by pluripotent stem cells prior to differentiation may be at least or about 10, 20, 30, 40, 50, 60, 70, 80, 90, 100, 150, 200, 250, 300, 350, 400 µm (or any range derivable therein) in diameter; in another aspect, at least about 20%, 30%, 40%, 50%, 80%, 90%, 95%, or 99% (or any range derivable therein) of the aggregates may comprise at least or about 10, 15, 20, 25, 30, 35, 40, 45, 50, 80, 100, 150, 200, 250, 300, 400, 500, 1000 cells, or any range derivable therein. In certain aspects, a substantial portion (e.g., about more than 50%, 80%, 90%, 95%, 99% or any range derivable therein) of the aggregates are about 80 to 200 µm in diameter. The approximately uniformity of an optimal range of aggregate size may help cardiomyocyte differentiation as differentiation is guided by spatial cues and interaction between various cell types, which can be manipulated by varying aggregate size.

As in the step of cardiac differentiation, the suspension culture for differentiating the stem cells may comprise any cardiac induction medium suitable for cardiac differentiation, for example, a cardiac induction medium having FGF, which may have a concentration of about 5 to about 200 ng/ml, such as at least or about 10, 15, 20, 25, 30, 35, 40, 45, 50, 55, 60, 65, 70, 75, 80, 85, 90, 95, 100, 150, 180, 200 ng/ml or any range derivable therein. In a further aspect, the suspension culture for differentiating or the cardiac induction medium may not include added ROCK inhibitor.

In a certain aspect, such a suspension culture in step a) or b) of any method described above may be at least or about 2 ml, 5 ml, 10 ml, 20 ml, 30 ml, 40 ml, 50 ml, 100 ml, 200 ml, 500 ml, 1 liters, 3 liters, 5 liters, 10 liters, 20 liters, or up to 25 liters, or any range derivable therein, such as in a bioreactor. Embodiments of the method may further comprise pooling multiple suspension cultures, for example, after step a). For example, multiple suspension cultures of aggregated cells may be pooled prior to differentiating the stem cells, or multiple suspension cultures of differentiated stem cells, such as cardiomyocytes, may be pooled.

In some further aspects, the pluripotent stem cells, such as transgenic iPS cells, may contain one or more transgenes, such as transgenes encoding a selectable marker, which for example confers antibiotic resistance, or a screenable marker, which may be fluorescent or luminescent. The aggregate promotion medium or cardiac induction medium may comprise an antibiotic that allow for selection of cells expressing the transgene. For cardiomyocyte selection or enrichment, the transgene may be under the control of a tissue-specific promoter, wherein the tissue specificity is for cardiomyocytes.

Furthermore, in certain aspects, methods may further comprise enriching or purifying the differentiated cardiomyocytes. In a certain embodiment, the cardiomyocytes may express one or more selectable or screenable transgene, wherein the transgene may be used for enrichment or purification of the cardiomyocytes. For example, the transgene may be an antibiotic resistance gene. For cardiomyocyte enrichment or isolation, such a transgene may be under the control of a promoter that is specific for cardiomyocytes, such as a myosin promoter or troponin T promoter.

Further embodiments provide an isolated cell population of at least or about $10^6$, $10^7$, $10^8$, $10^9$, $10^{10}$ cells (or any range derivable therein) comprising at least 90% (for example, at least or about 90%, 95%, 96%, 97%, 98%, 99%, 99.5%, or any range derivable therein) transgenic cardiomyocytes. In a specific example, the cell population may contain a transgene under a promoter specific for cardiomyocytes.

In some embodiment, there may be a cell population of at least or about $10^6$, $10^7$, $10^8$, $10^9$, $10^{10}$ cells (or any range derivable therein) comprising at least 90% (for example, at least or about 90%, 95%, 96%, 97%, 98%, 99%, 99.5%, or any range derivable therein) cardiomyocytes produced by a method comprising: a) obtaining a cell population from a transgenic induced pluripotent stem (iPS) cell; b) growing the population of transgenic iPS cells in at least one suspension culture of 5 milliliters to 25 liters comprising an aggregate formation medium having a ROCK inhibitor and FGF under conditions that promote aggregate formation; c) optionally pooling multiple suspension cultures containing iPS cell aggregates; d) then differentiating the pooled iPS cell aggregates into cardiomyocytes in a suspension culture comprising cardiac induction medium having FGF; and, e) enriching for cardiomyocytes.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-C: Double times for iPS 6.1 and iPS 6.1 MRB. These graphs show the doubling time of Dispase-split T150 control cells as well as NaCitrate split Double stack cells for both iPS 6.1 and iPS 6.1 MRB.

FIGS. 1A-B: Marking of ULA T75 or T25 flasks.

FIGS. 4A-D: Aggregates (Day 14) formed from IPS6.1 cells in Double Stacks (DS) and T150 flask.

FIGS. 5A-C: Aggregates (Day 14) formed from IPS6.1 MRB cells in Double Stacks (DS).

FIGS. 7A-C: 2nd round iPS MRB Day 14 Aggregates from DS.

FIGS. 8A-C: Flow cytometry pluripotency analysis of iPS6.1 and iPS6.1 MRB cells after four or seven passages with both dispase and NaCitrate cell splitting.

FIG. 9: Compiled data of cardiomyocyte cells generated from iPS6.1 and iPS6.1 MRB cells passaged with dispase in T150 flasks (control) and in Double stacks with NaCitrate.

FIG. 14A-E: Flow cytometry analysis of differentiated cardiomyocytes by cTNT staining.

FIGS. 15A-D: Count of cardiac cells differentiated from different initial iPS cell densities.

FIGS. 17A-D: Images of cell aggregates.

FIG. 20: Aggregate formation images from Experimental Design 1 of single cell aggregate formation for cardiomyocyte formation in $H_{1152}$.

FIGS. 24A-J: Images from Experiment 1 showing differences in aggregate numbers on day 14 of differentiation. FIG. 24A: 3e5 cells/ml initial seeding with 1 day $H_{1152}$. FIG. 24B: 3e5 cells/ml initial seeding with 2 days $H_{1152}$. FIG. 24C: 5e5 cells/ml initial seeding with 1 day $H_{1152}$. FIG. 24D: 5e5 cells/ml initial seeding with 2 days $H_{1152}$. FIG. 24E: 7e5 cells/ml initial seeding with 1 day $H_{1152}$. FIG. 24F: 7e5 cells/ml initial seeding with 2 days $H_{1152}$. FIG. 24G: 10e5 cells/ml initial seeding with 1 day $H_{1152}$. FIG. 24H: 10e5 cells/ml initial seeding with 2 days $H_{1152}$. FIG. 24I: 15e5 cells/ml initial seeding with 1 day $H_{1152}$. FIG. 24J: 15e5 cells/ml initial seeding with 2 days $H_{1152}$.

FIGS. 29A-B: Cardiac induction of iPS cells in the presence of various concentration of HGF and FGF. Cardiomyocyte yield and iPS cell conversion efficiency ratio as a function of HGF concentration. Error bars represent SEM (standard error of the mean) for n=3 T25 flask s in one experiment.

FIGS. 33A-D: The results of a growth factor/inhibitor screen utilizing varying concentrations of BMP (1 ng/mL, 10 ng/mL), dorsomorphin (2 uM, 0.2 uM), Activin A (1 ng/mL, 10 ng/mL), SB-431542 (10 uM, 0.1 uM) and a combination of Activin A (6 ng/mL) and BMP4 (10 ng/mL). FIG. 33C is actual data for 15 ml culture and FIG. 33D represents the calculated 1 L scale-up (as a projection for production) based on FIG. 33C data.

DESCRIPTION OF ILLUSTRATIVE EMBODIMENTS

I. Methods and Compositions

Figure 1:
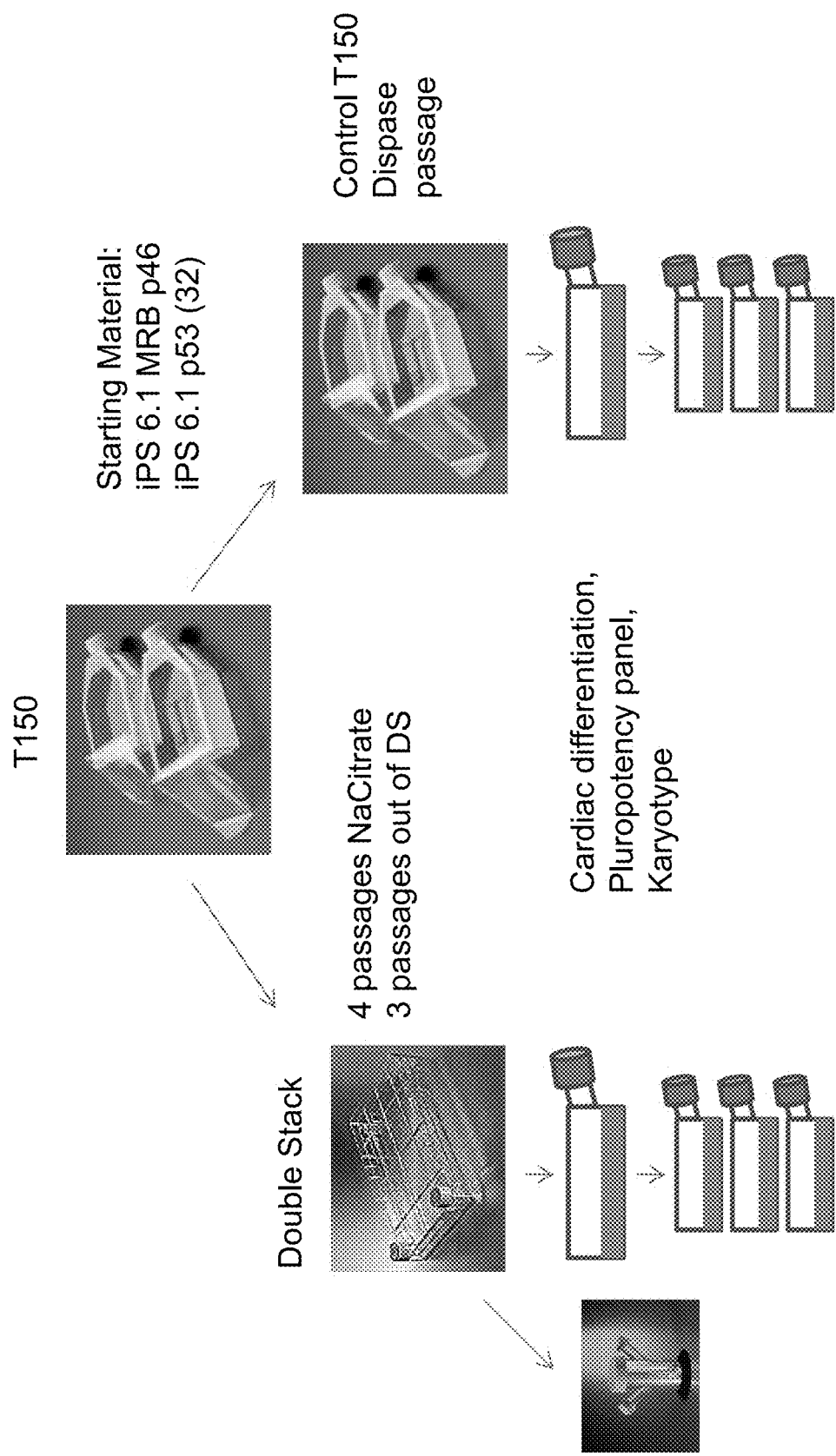
FIG. 1: NaCitrate Cell Splitting/Double Stack Scale up experimental design.

A variety of different methods and compositions are described herein. Certain embodiments concern several important advantages that improve the cardiomyocyte production process. First of all, it has been discovered that aggregate size can be controlled in a suspension culture, which provides optimal conditions for cardiac induction, such as through optimal rotary speed, seeding density, and/or time until cardiac induction. In some embodiments such methods increase uniformity and yields of the differentiated cells. Secondly, ROCK inhibitors have been combined with suspension culture to improve cell survival and differentiation in large volume culture vessels, such as bioreactors. In some embodiments, the concentration and/or duration of ROCK inhibitor incubation has been optimized. Further, provided herein is an exemplary technique for determining the appropriate adjustments in growth factor additions that can be employed to dramatically improve cardiac differentiation for any given medium batch or pluripotent cell clone employed.

Further advances in the production of cardiomyocyte cell populations are also described below. The remarkable uniformity and functional properties of the cells produced according to this disclosure make them valuable for studying cardiac tissue in vitro, and for developing new therapeutic modalities for regeneration of cardiac tissue in the treatment of heart disease.

II. Definitions

"Pluripotency" refers to a stem cell that has the potential to differentiate into all cells constituting one or more tissues or organs, for example, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" (or PSCs) used herein refer to cells that can differentiate into cells derived from any of the three germ layers, for example, descendants of totipotent cells, embryonic stem cells, or induced pluripotent stem cells.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing or contacting reprogramming factors.

"Embryonic stem (ES) cells" are pluripotent stem cells derived from early embryos.

"Suspension culture," refers to a culture in which cells, or aggregates of cells, multiply while suspended in liquid medium.

"Rho-associated kinase inhibitors," abbreviated as "ROCK inhibitors," refer to any substance that inhibits or reduces the function of Rho-associated kinase or its signaling pathway in a cell, such as a small molecule, an siRNA, a miRNA, an antisense RNA, or the like. "ROCK signaling pathway," as used herein, may include any signal processors involved in the ROCK-related signaling pathway, such as the Rho-ROCK-Myosin II signaling pathway, its upstream signaling pathway, or its downstream signaling pathway in a cell. Examples of ROCK inhibitors include, but are not limited to, a Rho-specific inhibitor, a ROCK-specific inhibitor, a MRLC (myosin regulatory light chain)-specific inhibitor, or a Myosin II-specific inhibitor.

The term "aggregate promoting medium" means any medium that enhances the aggregate formation of stem cells without any restriction as to the mode of action.

The term "cardiac induction medium" or "cardiac differentiation medium" means any medium that enhances the differentiation of stem cells to cardiomyocytes without any restriction as to the mode of action.

The term "cardiac maintenance medium" means any medium that is suitable for maintenance of cardiomyocytes without any restriction as to the mode of action.

The term "aggregates," i.e., embryoid bodies, refers to heterogeneous clusters comprising differentiated and partly differentiated cells that appear when pluripotent stem cells are allowed to differentiate in a non-specific fashion.

"Cardiomyocytes" refers generally to any cardiomyocytes lineage cells, and can be taken to apply to cells at any stage of cardiomyocytes ontogeny without any restriction, unless otherwise specified. For example, cardiomyocytes may include both cardiomyocyte precursor cells and mature cardiomyocytes.

A "gene," "polynucleotide," "coding region," "sequence," "segment," or "fragment," which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "transgene," refers to a gene, nucleic acid, or polynucleotide which has been introduced into the cell or organism by artificial or natural means, such as an exogenous nucleic acid. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

III. Sources of Pluripotent Stem Cells

The term "pluripotent stem cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming somatic cells. In certain embodiments, the pluripotent stem cell is an embryonic stem cell derived by somatic cell nuclear transfer.

A. Embryonic Stem Cells

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

A pluripotent cell is capable of differentiating into any cell of the body. The pluripotency of ES cells has been determined in various ways (Martin, 1982). In one test, mouse ES cells derived from the inner cell mass of a blastocyst are injected into the cavity of another blastocyst. The injected blastocyst is deposited into the uterus of a pseudopregnant female mouse to produce progeny that are chimeras of injected and recipient blastocyst cells. In another test, mouse ES cells are injected into adult mice to produce tumors called teratomas. Such tumors can contain a variety of cell types derived from endoderm, mesoderm, and ectoderm. In certain embodiments, one or more teratoma-derived cells may be cultured or differentiated into neuronal or neuronal-committed cells. The pluripotency of human ES cells can also be tested by the formation of teratomas in immunodeficient mice. A third test is to alter culture conditions to allow ES cells to differentiate into more specialized cells. For example, mouse ES cells can spontaneously differentiate into various cell types by removing the feeder layer and adding LIF to the culture medium. Similarly, human ES cells can spontaneously differentiate by removing the feeder layer and growing the ES cells on a non-adherent surface in suspension (Itskovitz-Eldor et al., 2000; Reubinoff et al., 2000; Roach et al., 1993). Under such conditions, the ES cells can form cell aggregates called embryoid bodies which contain cells having characteristics of neurons and heart muscle cells. In all of these tests, the pluripotency of ES cells is shown by their ability to generate cells of endoderm, mesoderm, and ectoderm origin.

ES cells can be characterized by the proteins they produce. For example, the following marker proteins have been used to characterize ES cells: stage-specific embryonic antigen SSEA-1, stage-specific embryonic antigen SSEA-3, stage-specific embryonic antigen SSEA-4, tumor rejection antigen-1-60 (TRA1-60), tumor rejection antigen-1-81 (TRA1-81), alkaline phosphatase (AP), and transcription factor Oct-4. As shown in Table 1, mouse, human and primate cells differ in their pattern of expression of these markers. For example, SSEA-1 is expressed in mouse ES cells, but not human or monkey ES cells, while TRA1-60 is expressed in human and monkey ES cells but not mouse ES cells.

TABLE 1

ES Cell Marker Expression

| Marker | Mouse | Human | Monkey |
|---|---|---|---|
| SSEA-1 | Yes | No | No |
| SSEA-2 | No | Yes | Yes |
| SSEQ-3 | No | Yes | Yes |
| TRA1-60 | No | Yes | Yes |
| TRA1-81 | No | Yes | Yes |
| AP | Yes | Yes | Yes |
| Oct-4 | Yes | Yes | Yes |

B. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10 \times 10^6$ cells into the rear leg muscles of 8-12 week old male SCID mice. Teratomas develop that demonstrate at least one cell type of each of the three germ layers.

In certain aspects of the present invention, iPS cells are maded from reprogramming somatic cells using reprogramming factors comprising Oct family member and a Sox family member, such as Oct4 and Sox2 in combination with Klf or Nanog as describe above. The somatic cell in the present invention may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector, such as a EBV element-based system (see U.S. Application No. 61/058,858, incorporated herein by reference; Yu et al., 2009). In a further aspect, reprogramming proteins could be introduced directly into somatic cells by protein transduction (see U.S. Application No. 61/172,079, incorporated herein by reference).

C. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque oocytes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

IV. Culturing of Pluripotent Stem Cells

Depending on culture conditions, pluripotent stem cells can produce colonies of differentiated cells or undifferentiated cells. The term "differentiate" means the progression of a cell down a developmental pathway. The term "differentiated" is a relative term describing a cell's progression down a developmental pathway in comparison with another cell. For example, a pluripotent cell can give rise to any cell of the body, while a more differentiated cell such as a hematopoetic cell will give rise to fewer cell types.

Cultures of pluripotent stem cells are described as "undifferentiated" when a substantial proportion of stem cells and their derivatives in the population display morphological characteristics of undifferentiated cells, clearly distinguishing them from differentiated cells of embryo or adult origin. Undifferentiated ES or iPS cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

In certain aspects, starting cells for the present methods may comprise at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/ml, or any range derivable therein.

A. Culturing of ES cells

ES cells can be maintained in an undifferentiated state by culturing the cells in the presence of serum and a feeder layer, typically mouse embryonic fibroblasts. Other methods for maintaining stem cells in an undifferentiated state are also known. For example, mouse ES cells can be maintained in an undifferentiated state by culturing in the presence of LIF without a feeder layer. However, unlike mouse ES cells, human ES cells do not respond to LIF. Human ES cells can be maintained in an undifferentiated state by culturing ES cells on a feeder layer of fibroblasts in the presence of basic fibroblast growth factor (Amit et al., 2000), or by culturing on a protein matrix, such as Matrigel™ or laminin, without a feeder layer and in the presence of fibroblast-conditioned medium plus basic fibroblast growth factor, (Xu et al., 2001; U.S. Pat. No. 6,833,269).

Methods for preparing and culturing ES cells can be found in standard textbooks and reviews in cell biology, tissue culture, and embryology, including teratocarcinomas and embryonic stem cells: A practical approach (1987); Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference. Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

B. Culturing of iPS Cells

After somatic cells are introduced or contacted with reprogramming factors, these cells may be cultured in a medium sufficient to maintain the pluripotency and the undifferentiated state. Culturing of induced pluripotent stem (iPS) cells generated in this invention can use various medium and techniques developed to culture primate pluripotent stem cells, more specially, embryonic stem cells, as described in U.S. Pat. Publication 20070238170 and U.S. Pat. Publication 20030211603, and U.S. Pat. Publication 20080171385, which are hereby incorporated by reference. It is appreciated that additional methods for the culture and maintenance of pluripotent stem cells, as would be known to one of skill, may be used with the present invention.

In certain embodiments, undefined conditions may be used; for example, pluripotent cells may be cultured on fibroblast feeder cells or a medium that has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006a; Ludwig et al., 2006b). Feeder-independent culture systems and media may be used to culture and maintain pluripotent cells. These approaches allow human embryonic stem cells to remain in an essentially undifferentiated state without the need for mouse fibroblast "feeder layers." As described herein, various modifications may be made to these methods in order to reduce costs as desired.

Various matrix components may be used in culturing and maintaining human pluripotent stem cells. For example, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in their entirety.

Matrigel™ may also be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

C. ROCK Inhibitors and Myosin II ATPase Inhibitors

Pluripotent stem cells, especially human ES cells and iPS cells, are vulnerable to apoptosis upon cellular detachment and dissociation, which are important for clonal isolation or expansion and differentiation induction. Recently, a small class of molecules have been found to increase clonal efficiency and survival of dissociated pluripotent stem cells, such as Rho-associated kinase (ROCK) inhibitors, which are inhibitors for ROCK-related signaling pathways, for example, Rho-specific inhibitors, ROCK-specific inhibitors or myosin II-specific inhibitors. In certain aspects of the invention, ROCK inhibitors may be used for culturing and passaging of pluripotent stem cells and/or differentiation of the stem cells. Therefore, ROCK inhibitors could be present in any cell culture medium in which pluripotent stem cells grow, dissociate, form aggregates, or undergo differentiation, such as an adherent culture or suspension culture.

ROCK signaling pathways may include Rho family GTPases, ROCK, a major effector kinase downstream of Rho, Myosin II, the predominant effector downstream of ROCK (Harb et al., 2008), and any intermediate, upstream, or downstream signal processors. ROCK may phosphorylate and inactivate myosin phosphatase target subunit 1 (MYPT1), one of the major downstream targets of ROCK that negatively regulates myosin function through dephosphorylation of myosin regulatory light chain (MRLC).

Rho-specific inhibitors, such as Clostridium botulinum C3 exoenzyme, and/or Myosin II-specific inhibitors may also be used as a ROCK inhibitor in certain aspects of the invention. Unless otherwise stated herein, myosin II inhibitors, such as blebbistatin, can substitute for the experimental use of ROCK inhibitors.

Myosin II was first studied for its role in muscle contraction, but it functions also in non-muscle cells. Myosin II (also known as conventional myosin) contains two heavy chains, each about 2000 amino acids in length, which constitute the head and tail domains. Each of these heavy chains contains the N-terminal head domain, while the C-terminal tails take on a coiled-coil morphology, holding the two heavy chains together (imagine two snakes wrapped around each other, such as in a caduceus). Thus, myosin II has two heads. It also contains 4 light chains (2 per head), which bind the heavy chains in the "neck" region between the head and tail. These light chains are often referred to as the essential light chain and the regulatory light chain. An exemplary Myosin II-specific inhibitor may be Blebbistatin or its derivatives.

ROCKs are serine/threonine kinases that serve as a target proteins for Rho (of which three isoforms exist—RhoA, RhoB and RhoC). Theses kinases were initially characterized as mediators of the formation of RhoA-induced stress fibers and focal adhesions. The two ROCK isoforms— ROCK1 (p160ROCK, also called ROKβ) and ROCK2 (ROKα)—are comprised of a N-terminal kinase domain, followed by a coiled-coil domain containing a Rho-binding domain and a pleckstrin-homology domain (PH). Both ROCKs are cytoskeletal regulators, mediating RhoA effects on stress fiber formation, smooth muscle contraction, cell adhesion, membrane ruffling and cell motility. ROCKs may exert their biological activity by targeting downstream molecules, such as myosin II, myosin light chain (MLC), MLC phosphatase (MLCP) and the phosphatase and tensin homolog (PTEN).

An exemplary ROCK-specific inhibitor is Y-27632, which selectively targets ROCK1 (but also inhibits ROCK2), as well as inhibits TNF-α and IL-β. It is cell permeable and inhibits ROCK1/ROCK2 ($IC_{50}$=800 nM) by competing with ATP. Ishizaki et al. (2000), incorporated herein by reference as if set forth in its entirety. Other ROCK inhibitors include, e.g., H-1152, Y-30141, Wf-536, HA-1077, hydroxyl-HA-1077, GSK269962A and SB-772077-B. Doe et al. (2007); Ishizaki et al., supra; Nakajima et al. (2003); and Sasaki et al. (2002), each of which is incorporated herein by reference as if set forth in its entirety.

Other non-limiting examples of ROCK inhibitors include H-1152 and Fasudil (also referred to as HA1077), Y-30141 (described in U.S. Pat. No. 5,478,838), and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in embodiments (for example, refer to U.S. Patent Publication Nos. 20050209261, 20050192304, 20040014755, 20040002508, 20040002507, 20030125344 and 20030087919, and International Patent Publication Nos. 2003/062227, 2003/059913, 2003/062225, 2002/076976 and 2004/039796, which are hereby incorporated by reference). In the present invention, a combination of one or two or more of the ROCK inhibitors can also be used.

According to some embodiments, the stem cell can be treated with a ROCK inhibitor in a medium. Thereby, the medium used in the methods of the present invention may already contain the ROCK inhibitor or alternatively, the methods of the present invention may involve a step of adding the ROCK inhibitor to the medium. The concentration of the ROCK inhibitor in the medium is particularly not limited as far as it can achieve the desired effects such as the improved survival rate of stem cells. Such a ROCK inhibitor, e.g., Y-27632, HA-1077, or H-1152, may be used at an effective concentration of at least or about 0.02, 0.05, 0.1, 0.2, 0.5, 1, 2, 3, 4, 5, 10, 15, 20, 25, 30, 35, 40, 45, 50, 100, 150, 200, 500 to about 1000 µM, or any range derivable therein. These amounts may refer to an amount of a ROCK inhibitor individually or in combination with one or more ROCK inhibitors.

For example, when Y-27632 is used as the ROCK inhibitor, it can be used at the concentration of about 0.01 to about 1000 µM, more specifically about 0.1 to about 100 µM, further more specifically about 1.0 to about 30 µM, and most specifically about 2.0 to 20 µM, or any range derivable therein. When Fasudil/HA1077 is used as the ROCK inhibitor, it can be used at about twofold the aforementioned Y-27632 concentration. When H-1152 is used as the ROCK inhibitor, it can be used at about ⅕₀th of the aforementioned Y-27632 concentration.

The time for treating with the ROCK inhibitor is particularly not limited as long as it is a time duration for which the desired effects such as the improved survival rate of stem cells can be achieved. For example, when the stem cell is a pluripotent stem cells such as a human embryonic stem cell, the time for treating is at least or about 10, 15, 20, 25, 30 minutes to several hours (e.g., at least or about one hour, two hours, three hours, four hours, five hours, six hours, eight hours, 12 hours, 16 hours, 24 hours, 36 hours, 48 hours, or any range derivable therein) before dissociation. After dissociation, the pluripotent stem cell can be treated with the ROCK inhibitor for, for example, at least or about 2, 3, 4, 5, 6, 7, 8, 9, 10, 11, 12, 16, 24, 48 hours or more to achieve the desired effects.

The density of the stem cell(s) to be treated with the ROCK inhibitor is particularly not limited as far as it is a density at which the desired effects such as the improved survival rate of stem cells can be achieved. It is, for example, about $1.0 \times 10^1$ to $1.0 \times 10^7$ cells/ml, more particularly about $1.0 \times 10^2$ to $1.0 \times 10^7$ cells/ml, further more particularly about $1.0 \times 10^3$ to $1.0 \times 10^7$ cells/ml, and most particularly about $3.0 \times 10^4$ to $2.0 \times 10^6$ cells/ml.

In certain embodiments, stem cells are cultured in the presence of ROCK inhibitors to improve survival at low density (dissociated into single cells or small aggregates), cloning efficiency or passaging efficiency. In certain embodiments of the invention, the stem cells are cultured in the absence of feeder cells, feeder cell extracts and/or serum. The stem cells can be cultured in the presence of a ROCK inhibitor prior to subcloning or passaging, e.g., for at least one hour before subcloning or passaging. Alternatively or additionally, the stem cells are maintained in the presence of a ROCK inhibitor during or after subcloning or passaging.

In certain embodiments, the stem cells are maintained in the presence of a ROCK inhibitor for at most or at least about 4, 8, 12 hours, about 2, about 4, or about 6 days, or any range derivable therein. In other embodiments, the stem cells are maintained in the presence of a ROCK inhibitor for at least one to five passages. Optionally, the ROCK inhibitor is subsequently withdrawn from the culture medium, for example after about 4, 8, 12 hours or after about 2, about 4, or about 6 days, or any range derivable therein. In other embodiments, the ROCK inhibitor is withdrawn after at least one, two, three, four, five passages or more, or any range derivable therein.

The stem cells to be treated with a ROCK inhibitor according to the present invention can be dissociated cells or non-dissociated cells. The dissociated cells refer to cells treated to promote cell dissociation (for example, the dissociation described later). Dissociated cells include a single cell and cells having formed a small cell clump (aggregate) of several (typically about 2 to 50, 2 to 20, or 2 to 10) cells. The dissociated cells can be suspended (floating) cells or adhered cells. For example, it has been known that ES cells such as human ES cells are susceptible to specific conditions such as dissociation (and/or suspension culture after dissociation). The methods of the present invention have particular use when the stem cell is subject to conditions at which hitherto cell death would have occurred.

Certain aspects of the present invention can further involve a step of dissociating stem cells. Stem cell dissociation can be performed using any known procedures. These procedures include treatments with a chelating agent (such as EDTA), an enzyme (such as trypsin, collagenase), or the like, and operations such as mechanical dissociation (such as pipetting). The stem cell(s) can be treated with the ROCK inhibitor before and/or after dissociation. For example, the stem cell(s) can be treated only after dissociation.

D. Stem Cell Culture Conditions

The culturing conditions according to the present invention will be appropriately defined depending on the medium and stem cells used. The medium according to the present invention can be prepared using a medium to be used for culturing animal cells as its basal medium. As the basal medium, any of TeSR, BME, BGJb, CMRL 1066, Glasgow MEM, Improved MEM Zinc Option, IMDM, Medium 199, Eagle MEM, aMEM, DMEM, Ham, RPMI 1640, and Fischer's media, as well as any combinations thereof can be used, but the medium is not particularly limited thereto as far as it can be used for culturing animal cells.

The medium according to the present invention can be a serum-containing or serum-free medium. The serum-free medium refers to media with no unprocessed or unpurified serum and accordingly, can include media with purified blood-derived components or animal tissue-derived components (such as growth factors). From the aspect of preventing contamination with heterogeneous animal-derived components, serum can be derived from the same animal as that of the stem cell(s).

The medium according to the present invention may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolgiycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium of the present invention can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the stem cell(s).

A culture vessel used for culturing the stem cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, and roller bottle, as long as it is capable of culturing the stem cells therein. The stem cells may be culture in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, laminin, and fibronectin and mixtures thereof for example Matrigel™, and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least or about 1, 5, 8, 10, 20%, or any range derivable therein.

The methods of the present invention can be used for adhesion culture of stem cells, for example. In this case, the cells can be cultured in the presence of feeder cells. In the case where the feeder cells are used in the methods of the present invention, stromal cells such as fetal fibroblasts can be used as feeder cells (for example, refer to; Manipulating the Mouse Embryo A Laboratory Manual (1994); Gene Targeting, A Practical Approach (1993); Martin (1981); Evans et al. (1981); Jainchill et al., (1969); Nakano et al., Science (1996); Kodama et al. (1982); and International Publication Nos. 01/088100 and 2005/080554).

The methods of the present invention can be also used for a suspension culture of stem cells, including suspension culture on carriers (Fernandes et al., 2007) or gel/biopolymer encapsulation (United States Patent 20070116680). The term suspension culture of the stem cells means that the stem cells are cultured under non-adherent condition with respect to the culture vessel or feeder cells (if used) in a medium. The suspension culture of stem cells includes a dissociation culture of stem cells and an aggregate suspension culture of stem cells. The term dissociation culture of stem cells means that suspended stem cells is cultured, and the dissociation culture of stem cells include those of single stem cell or those of small cell aggregates composed of a plurality of stem cells (for example, about 2 to 400 cells). When the aforementioned dissociation culture is continued, the cultured, dissociated cells form a larger aggregate of stem cells, and thereafter an aggregate suspension culture can be performed. The aggregate suspension culture includes an embryoid culture method (see Keller et al., 1995), and a SFEB method (Watanabe et al., 2005); International Publication No. 2005/123902). The methods of the present invention can significantly improve the survival rate and/or differentiation efficiency of stem cells in a suspension culture.

E. Single Cell Passaging

In some embodiments of pluripotent stem cell culturing, once a culture container is full, the colony is split into aggregated cells or even single cells by any method suitable for dissociation, which cell are then placed into new culture containers for passaging. Cell passaging or splitting is a technique that enables to keep cells alive and growing under cultured conditions for extended periods of time. Cells usually would be passed when they are about 70%-100% confluent.

Single-cell dissociation of pluripotent stem cells followed by single cell passaging may be used in the present methods with several advantages, like facilitating cell expansion, cell sorting, and defined seeding for differentiation and enabling automatization of culture procedures and clonal expansion. For example, progeny cell clonally derivable from a single cell may be homogenous in genetic structure and/or synchronized in cell cycle, which may increase targeted differentiation. Exemplary methods for single cell passaging may be as described in U.S. Pat. App. 20080171385, which is incorporated herein by reference.

In certain embodiments, pluripotent stem cells may be dissociated into single individual cells, or a combination of single individual cells and small cell clusters comprising 2, 3, 4, 5, 6, 7, 8, 9, 10 cells or more. The dissociation may be achieved by mechanical force, or by a cell dissociation agent, such as NaCitrate, or an enzyme, for example, trypsin, trypsin-EDTA, TrypLE Select, or the like.

Based on the source of pluripotent stem cells and the need for expansion, the dissociated cells may be transferred individually or in small clusters to new culture containers in a splitting ratio such as at least or about 1:2, 1:4, 1:5, 1:6, 1:8, 1:10, 1:20, 1:40, 1:50, 1:100, 1:150, 1:200, or any range derivable therein. Suspension cell line split ratios may be done on volume of culture cell suspension. The passage interval may be at least or about every 1, 2, 3, 4, 5, 6, 7, 8, 9, 10, 11, 12, 13, 14, 15, 16, 17, 18, 19, 20 days or any range derivable therein. For example, the achievable split ratios for the different enzymatic passaging protocols may be 1:2 every 3-7 days, 1:3 every 4-7 days, and 1:5 to 1:10 approximately every 7 days, 1:50 to 1:100 every 7 days. When high split ratios are used, the passage interval may be extended to at least 12-14 days or any time period without cell loss due to excessive spontaneous differentiation or cell death.

In certain aspects, single cell passaging may be in the presence of a small molecule effective for increasing cloning efficiency and cell survival, such as a ROCK inhibitor as described above. Such a ROCK inhibitor, e.g., Y-27632, HA-1077, H-1152, or blebbistatin, may be used at an effective concentration, for example, at least or about 0.02, 0.05, 0.1, 0.2, 0.5, 1, 2, 3, 4, 5, 10, 15, 20, 25, 30, 35, 40, 45, 50 to about 100 µM, or any range derivable therein.

V. Methods for Cardiac Differentiation

Differentiation of pluripotent stem cells can be induced in a variety of manners, such as in attached colonies or by formation of cell aggregates, e.g., in low-attachment environment, wherein those aggregates are referred to as embryoid bodies (EBs). The molecular and cellular morphogenic signals and events within EBs mimic many aspects of the natural ontogeny of such cells in a developing embryo. However, currently there remain no satisfactory methods for producing large quantities of cardiac cells in a controlled environment. Certain aspects of the invention disclose methods using non-static suspension culture to control aggregate size and differentiation yield and produce cardiomyocytes at a commercial scale.

A. Aggregate Formation

Embryoid bodies (EBs) are aggregates of cells derived from pluripotent stem cells, such as ES cells or iPS cells, and have been studied for years with mouse embryonic stem cells. In order to recapitulate some of the cues inherent to in vivo differentiation, certain aspects of the invention may employ three-dimensional aggregates (i.e., embryoid bodies) as an intermediate step. Upon aggregation, differentiation is initiated and the cells begin to a limited extent to recapitulate embryonic development. Though they cannot form trophectodermal tissue (which includes the placenta), cells of virtually every other type present in the organism can develop. The present invention may further promote cardiac differentiation following aggregate formation.

Cell aggregation may be imposed by hanging drop, plating upon non-tissue culture treated plates or spinner flasks; either method prevents cells from adhering to a surface to form the typical colony growth. As described above, ROCK inhibitors may be used before, during or after aggregate formation to culture pluripotent stem cells.

Pluripotent stem cells may be seeded into aggregate promotion medium using any method known in the art of cell culture. For example, pluripotent stem cells may be seeded as a single colony or clonal group into aggregate promotion medium, and pluripotent stem cells may also be seeded as essentially individual cells. In some embodiments, pluripotent stem cells are dissociated into essentially individual cells using mechanical or enzymatic methods known in the art. By way of non-limiting example, pluripotent stem cells may be exposed to a proteolytic enzyme which disrupts the connections between cells and the culturing surface and between the cells themselves. Enzymes which may be used to individualize pluripotent stem cells for aggregate formation and differentiation may include, but are not limited to, trypsin, in its various commercial formulations, such as TrypIE, or a mixture of enzymes such as Accutase®.

In certain embodiments, pluripotent cells may be added or seeded as essentially individual (or dispersed) cells to a culturing medium for culture formation on a culture surface. The culturing medium into which cells are seeded may comprise TeSR medium or mTeSR medium and a survival factor such as ROCK inhibitor. For example, dispersed pluripotent cells are seeded into a culturing medium at a density of from about $10^4$ cells/ml to about $10^{10}$ cells/ml. More particularly, pluripotent cells are seeded at a density of from about $10^5$ cells/ml to about $10^7$ cells/ml, or about $0.5 \times 10^6$ cells/ml to about $3 \times 10^6$ cells/ml. In these embodiments, a culturing surface may be comprised of essentially any material which is compatible with standard aseptic cell culture methods in the art, for example, a non-adherent surface. A culturing surface may additionally comprise a matrix component as described herein. In certain embodiments, a matrix component may be applied to a culturing surface before contacting the surface with cells and medium.

B. Cardiomyocyte Differentiation

Cardiomyocyte lineage cells can be obtained from undifferentiated stem cells by culturing or differentiating in a special growth environment that enriches for cells with the desired phenotype (either by outgrowth of the desired cells, or by inhibition or killing of other cell types).

In certain aspects, the iPS cells may be differentiated into cardiac cells in cell suspension incorporating the disclosed methods. Differentiation can be initiated by forming embryoid bodies or aggregates as described above: for example, by overgrowth of a pluripotent stem cell culture, or by culturing pluripotent stem cells in suspension in culture vessels having a substrate with low adhesion properties which allows EB formation. Pluripotent stem cells could be harvested by brief collagenase digestion, dissociated into clusters, and plated in non-adherent cell culture plates (WO 01/51616; U.S. Pat. No. 6,602,711, incorporated by reference). Optionally, the EBs can be produced encapsulated in alginate or other suitable nutrient-permeable matrix, which may help improve the uniformity of EB diameter and consistency of the cells produced (WO 03/004626, Zandstra et al., incorporated by reference). Whether or not the process involves EB formation, using a medium that contains serum or serum equivalent promotes foci of contracting cells of the cardiomyocyte lineage: for example, about 20% fetal bovine serum, or a serum supplement such as B27 or N2 in a suitable growth medium such as RPMI. More exemplary methods of cardiac differentiation may include embryoid body (EB) methods (Zhang, et al., 2009, which is incorporated by reference), OP9 stroma cell methods (Narazaki, et al., 2008, which is incorporated by reference), or growth factor/chemical methods (see U.S. Patent Publication Nos. 20080038820, 20080226558, 20080254003 and 20090047739, all incorporated herein by reference in their entirety).

To promote the cardiomyocyte phenotype, the cells can be cultured with factors and factor combinations that enhance proliferation or survival of cardiomyocyte type cells, or inhibit the growth of other cell types. The effect may be due to a direct effect on the cell itself, or due to an effect on another cell type, which in turn enhances cardiomyocyte formation. For example, factors that induce the formation of hypoblast or epiblast equivalent cells, or cause these cells to produce their own cardiac promoting elements, all come within the rubric of cardiotropic factors or differentiation factors for cardiomyocyte differentiation.

For example, induction medium for cardiac differentiation may include, but is not limited to, precardiac explants, precardiac mesoderm conditioned medium, mesoderm secreted growth factors such as HGF.

In certain aspects of the invention, the timing and amount of addition of differentiation factors may be screened for appropriate conditions for differentiation of stem cells into cardiomyocytes. In a particular aspect, the differentiation factors may be growth factors that are involved in cell development. The differentiation factors may include, but not be limited to, one or more of modulators of signaling pathways of bone morphogenetic protein, ActivinA/Nodal, vascular endothelial growth factor (VEGF), dickkopf homolog 1 (DKK1), basic fibroblast growth factor (bFGF), insulin growth factor (IGF), and/or epidermal growth factor (EGF).

It is contemplated that additional factors may be screened for its optimal concentration or timing in the cell differentiation environment, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family agonists or antagonists including but not limited to noggin, follistatin, chordin, gremlin, cerberus/DAN family proteins, GDF family proteins such as GDF-3, ventropin, and amnionless or variants or functional fragments thereof. TGF/BMP/GDF antagonists could also be added in the form of TGF/BMP/GDF receptor-Fc chimeras. Other factors that may be screened include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGE), insulin, the wingless related (WNT) factor family, and the hedgehog factor family or variants or functional fragments thereof. Additional factors may be screened or added to promote mesoderm stem/progenitor, endoderm stem/progenitor, mesoderm stem/progenitor, or definitive endoderm stem/progenitor proliferation and survival as well as survival and differentiation of derivatives of these progenitors.

Differentiation factors thought to induce differentiation of pluripotent stem cells into cells of the mesoderm layer, or facilitate further differentiation into cardiomyocyte lineage cells include the following non-limiting examples:

Transforming Growth Factor beta-related ligands (exemplified by TGF-β1, TGF-β2, TGF-β3 and other members of the TGF-β3 superfamily illustrated below). Ligands bind a TGF-β receptor activate Type I and Type II serine kinases and cause phosphorylation of the Smad effector.

Morphogens like Activin A and Activin B (members of the TGF-β superfamily).

Insulin-like growth factors (such as IGF I and IGF II).

Bone morphogenic proteins (members of the TGF-β superfamily, exemplified by BMP-2 and BMP-4).

Fibroblast growth factors (exemplified by bFGF, FGF-4, and FGF-8), other ligands that activate cytosolic kinase raf-1 and mitogen-activated proteins kinase (MAPK), and other mitogens such as epidermal growth factor (EGF).

Nucleotide analogs that affect DNA methylation and altering expression of cardiomyocyte-related genes (e.g., 5-aza-deoxy-cytidine).

The pituitary hormone oxytocin, or nitric oxide (NO).

Specific antibodies or synthetic compounds with agonist activity for the same receptors.

Exemplary effective combinations of cardiotropic agents include use of a morphogen like Activin A and a plurality of growth factors, such as those included in the TGF-β and IGF families during the early commitment stage, optionally supplemented with additional cardiotropins such as one or more fibroblast growth factors, bone morphogenic proteins, and platelet-derived growth factors.

Without wishing to be bound by theory, in certain aspects it is contemplated that TGFβ signaling pathways may be delicately regulated by adjusting timing and level of the external addition of certain growth factors to achieve optimal specific lineage differentiation condition, such as for differentiation of cardiomyocytes. In certain aspects, the addition of differentiation factors may help account for variability in the activity of TGFβ signaling pathway activity for a combination of a selected stem cell clone and a selected culture medium, particularly, in the relative activity of different TGFβ signaling pathways, such as a relative activity ratio between BMP signaling and Activin signaling.

The transforming growth factor beta (TGFβ) signaling pathway as is involved in many cellular processes in both the adult organism and the developing embryo including cell growth, cell differentiation, apoptosis, cellular homeostasis and other cellular functions. In spite of the wide range of cellular processes that the TGFβ signaling pathway regulates, the process is relatively simple. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

Stem cells exhibit self-renewing capacity and pluripotency in generating the multitude of embryonic and adult cell types of the metazoan body (reviewed by Rossi et al., 2008). Growth factors, such as TGFβ and FGF, regulate stem cell self-renewal and differentiation. FGF2, the most widely used growth factor that supports mouse and human embryonic stem cell (ESC) self-renewal in culture, induces TGFβ/activin ligands and receptors while suppressing BMP-like activities (Greber et al., 2007; Ogawa et al., 2007). Furthermore, pharmacological inhibitors of the TGFβ/nodal type I receptor family suppress human and mouse ESC self-renewal (Ogawa et al., 2007). In general, TGFβ inhibits differentiation of pluripotent progenitor cells, whereas BMP induces their differentiation (Watabe and Miyazono, 2009).

To promote self-renewal of ESCs, TGFβ/nodal signaling activates SMAD2 and SMAD3, which directly induce Nanog, one of the crucial stem cell transcription factors (Xu, R. H. et al., 2008). TGFβ and FGF signaling synergize by enhancing binding of Smad complexes to the Nanog promoter. Interestingly, NANOG provides a molecular link for the antagonism between TGFβ (the self-renewing factor)

and BMP (the differentiation factor) in ESCs. Nanog binds to SMAD1, inhibiting its transcriptional activity and limiting the BMP signaling potential that promotes early meso-dermal differentiation or tissue-specific differentiation later in development (Suzuki et al., 2006). This example is likely to be expanded to additional regulators of ESC self renewal and differentiation as a result of genome-wide screens for the transcription and signaling factors of these pathways (Chen et al., 2008).

The TGF Beta superfamily of ligands include: Bone morphogenetic proteins (BMPs), Growth and differentiation factors (GDFs), Anti-mullerian hormone (AMH), Activin, Nodal and TGFβ's. Signaling begins with the binding of a TGF beta superfamily ligand to a TGF beta type II receptor. The type II receptor is a serine/threonine receptor kinase, which catalyses the phosphorylation of the Type I receptor. Each class of ligand binds to a specific type II receptor. In mammals there are seven known type I receptors and five type II receptors.

There are three activins: Activin A, Activin B and Activin AB. Activins are involved in embryogenesis and osteogenesis. They also regulate many hormones including pituitary, gonadal and hypothalamic hormones as well as insulin. They are also nerve cell survival factors.

The BMPs bind to the Bone morphogenetic protein receptor type-2 (BMPR2). They are involved in a multitude of cellular functions including osteogenesis, cell differentiation, anterior/posterior axis specification, growth, and homeostasis.

The TGF beta family include: TGFβ1, TGFβ2, TGFβ3. Like the BMPS, TGF betas are involved in embryogenesis and cell differentiation, but they are also involved in apoptosis, as well as other functions. They bind to TGF-beta receptor type-2 (TGFBR2).

Nodal binds to activin A receptor, type IIB ACVR2B. It can then either form a receptor complex with activin A receptor, type IB (ACVR1B) or with activin A receptor, type IC (ACVR1C).

The TGF beta signaling pathway (Table 24) is involved in a wide range of cellular process and subsequently is very heavily regulated. There are a variety of mechanisms that the pathway is modulated both positively and negatively: There are agonists for ligands and R-SMADs; there are decoy receptors; and R-SMADs and receptors are ubiquitinated.

TABLE 24

TGF beta signaling pathway

| TGF Beta superfamily ligand | Type II Receptor | Type I receptor | R-SMADs | coSMAD | Ligand inhibitors |
|---|---|---|---|---|---|
| Activin A | ACVR2A | ACVR1B (ALK4) | SMAD2, SMAD3 | SMAD4 | Follistatin |
| GDF1 | ACVR2A | ACVR1B (ALK4) | SMAD2, SMAD3 | SMAD4 | |
| GDF11 | ACVR2B | ACVR1B (ALK4), TGFβRI (ALK5) | SMAD2, SMAD3 | SMAD4 | |
| Bone morphogenetic proteins | BMPR2 | BMPR1A (ALK3), BMPR1B (ALK6) | SMAD1, SMAD5, SMAD8 | SMAD4 | Noggin, Chordin, DAN |
| Nodal | ACVR2B | ACVR1B (ALK4), ACVR1C (ALK7) | SMAD2, SMAD3 | SMAD4 | Lefty |
| TGFβs | TGFβRII | TGFβRI (ALK5) | SMAD2, SMAD3 | SMAD4 | LTBP1, THBS1, Decorin |

In certain embodiments the compositions and methods of the present invention comprise adjustment of activity of transforming growth factor beta (TGF-β) or a TGF-β family member or variants or functional fragments thereof to determine an appropriate or optimal differentiation condition.

As used herein, the term "member of the TGF-β family" or the like refers to growth factors that are generally characterized by one of skill in the art as belonging to the TGF-β family, either due to homology with known members of the TGF-β family, or due to similarity in function with known members of the TGF-β family. In particular embodiments of the invention, if the member of the TGF-β family is present, the TGF-β family member of variant or functional fragment thereof activates SMAD 2 or 3. In certain embodiments, the member of the TGF-β family is selected from the group consisting of Nodal, Activin A, Activin B, TGF-β, bone morphogenic protein-2 (BMP2) and bone morphogenic protein-4 (BMP4). In one embodiment, the member of the TGF-β family is Activin A.

It is contemplated that if Nodal is present, it may be varied from a concentration of approximately 0.1 ng/mL to approximately 2000 ng/ml, more preferably approximately 1 ng/mL to approximately 1000 ng/ml, more preferably approximately 10 ng/mL to approximately 750 ng/ml, or more preferably approximately 25 ng/mL to approximately 500 ng/ml. It is contemplated that if used, Activin A may be varied at a concentration of approximately 0.01 ng/mL to approximately 1000 ng/ml, more preferably approximately 0.1 ng/mL to approximately 100 ng/ml, more preferably approximately 0.1 ng/mL to approximately 25 ng/ml, or most preferably at a concentration of approximately 6 to 20 ng/ml. It is contemplated that if present, TGF-β may be varied present at a concentration of approximately 0.01 ng/mL to approximately 100 ng/ml, more preferably approximately 0.1 ng/mL to approximately 50 ng/ml, or more preferably approximately 0.1 ng/mL to approximately 20 ng/ml.

In certain embodiments, the compositions and methods comprise an inhibitor or an inactivator of Activin/Nodal signaling. As used herein, an "inhibitor or inactivator of Activin/Nodal signaling" refers to an agent that antagonizes the activity of one or more Activin/Nodal proteins or any of their upstream or downstream signaling components through any of its possible signaling pathways. Non-limiting examples include SB-431542.

In certain embodiments, the compositions and methods comprise an inhibitor or an inactivator of BMP signaling. As used herein, an "inhibitor or inactivator of BMP signaling" refers to an agent that antagonizes the activity of one or more BMP proteins or any of their upstream or downstream signaling components through any of its possible signaling pathways. The compound(s) used to inactivate BMP signaling can be any compound known in the art, or later discovered. Non-limiting examples of inhibitors of BMP signaling include dorsomorphin, dominant-negative, truncated BMP receptor, soluble BMP receptors, BMP receptor-Fc chimeras, noggin, follistatin, chordin, gremlin, cerberus/DAN family proteins, ventropin, high dose activin, and amnionless.

During the elaboration of this invention, it was found that omitting factors such as insulin-like growth factor II (IGF II) and related molecules from the final stages of in vitro differentiation actually increase the levels of cardiac gene expression. In unrelated studies, IGF II has been found to decrease the levels of GSK3β in fibroblasts (Scalia et al., 2001). IGF II may therefore potentiate the effects of Wnt proteins present in the culture medium or secreted by the cells. Wnt proteins normally stabilize and cause nuclear translocation of a cytoplasmic molecule, β-catenin, which comprises a portion of the transcription factor TCF. This changes transcriptional activity of multiple genes. In the absence of Wnt, β-catenin is phosphorylated by the kinase GSK3β, which both destabilizes β-catenin and keeps it in the cytoplasm.

Since Wnt activators like IGF II apparently limit cardiomyocyte differentiation, certain aspects of this invention may include culturing with Wnt antagonists to increase the extent or proportion of cardiomyocyte differentiation of pluripotent stem cells. Wnt signaling can be inhibited by injection of synthetic mRNA encoding either DKK-1 or Crescent (secreted proteins that bind and inactivate Wnts) (Schneider et al., 2001), or by infection with a retrovirus encoding DKK-1 (Marvin et al., 2001). Alternatively, the Wnt pathway can be inhibited by increasing the activity of the kinase GSK3β, for example, by culturing the cells with factors such as IL-6 or glucocorticoids.

In a cerain embodiment, FGF or a combination of FGF and HGF are used to culture pluripotent stem cells, cell aggregates, or differentiated stem cells, which may promote cardiac induction of stem cells. For example, FGF may be added at a concentration of at least or about 5, 10, 15, 20, 25, 30, 35, 40, 45, 50, 55, 60, 65, 70, 75, 80, 85, 90, 95, 100, 150, 180, 200, 250 ng/ml or any range derivable therein. Optionally hepatic growth factor (HGF) may also be included, for example at a concentration of at least or about 5, 10, 15, 20, 25, 30, 35, 40, 45, 50, 55, 60, 65, 70, 75, 80, 85, 90, 95, 100, 150, 180, 200, 250 ng/ml or any range derivable therein.

C. Non-static Culture

In certain aspects, non-static culture could be used for cardiac induction of pluripotent stem cells. Suspension culture can be used to produce large scale of EBs and cardiomyocytes subsequently; however, static culture has little control over the size and shape of EBs formed, which directly influence yield and quality of cardiomyocyte differentiated therefrom. The non-static culture can be any culture with cells kept at a controlled moving speed, by using, for example, shaking, rotating, or stirring platforms or culture vessels, particularly large-volume rotating bioreactors. The agitation may improve circulation of nutrients and cell waste products and also be used to control cell aggregation by providing a more uniform environment. For example, rotary speed may be set to at least or at most about 25, 30, 35, 40, 45, 50, 75, 100 rpm, or any range derivable therein. The incubation period in the non-static culture for pluripotent stem cells, cell aggregates, differentiated stem cells, or cardiomyocytes derivable therefrom, may be at least or about 4 hours, 8 hours, 16 hours, or 1, 2, 3, 4, 5, 6 days, or 1, 2, 3, 4, 5, 6, 7 weeks, or any range derivable therein.

VI. Characterization of Cardiomyocyte Lineage Cells

The cells obtained according to the techniques of this invention can be characterized according to a number of phenotypic criteria. Cardiomyocytes and precursor cells derived from pluripotent stem cell lines often have morphological characteristics of cardiomyocytes from other sources. They can be spindle, round, triangular or multi-angular shaped, and they may show striations characteristic of sarcomeric structures detectable by immunostaining. They may form flattened sheets of cells, or aggregates that stay attached to the substrate or float in suspension, showing typical sarcomeres and atrial granules when examined by electron microscopy.

Pluripotent stem cell-derived cardiomyocytes and their precursors typically have at least one of the following cardiomyocyte specific markers:

Cardiac troponin I (cTnI), a subunit of troponin complex that provides a calcium-sensitive molecular switch for the regulation of striated muscle contraction.

Cardiac troponin T (cTnT).

Nkx2.5, a cardiac transcription factor expressed in cardiac mesoderm during early mouse embryonic development, which persists in the developing heart.

The cells will also typically express at least one (and often at least 3, 5, or more) of the following markers:

Atrial natriuretic factor (ANF), a hormone expressed in developing heart and fetal cardiomyocytes but down-regulated in adults. It is considered a good marker for cardiomyocytes because it is expressed in a highly specific manner in cardiac cells but not skeletal myocytes.

myosin heavy chain (MHC), particularly the β chain which is cardiac specific

Titin, tropomyosin, .alpha.-sarcomeric actinin, and desmin

GATA-4, a transcription factor that is highly expressed in cardiac mesoderm and persists in the developing heart. It regulates many cardiac genes and plays a role in cardiogenesis MEF-2A, MEF-2B, MEF-2C, MEF-2D; transcription factors that are expressed in cardiac mesoderm and persist in developing heart N-cadherin, which mediates adhesion among cardiac cells Connexin 43, which forms the gap junction between cardiomyocytes.

β1-adrenoceptor (β1-AR)

creatine kinase MB (CK-MB) and myoglobin, which are elevated in serum following myocardial infarction α-cardiac actin, early growth response-I, and cyclin D2.

Tissue-specific markers can be detected using any suitable immunological technique—such as flow immunocytometry or affinity adsorption for cell-surface markers, immunocytochemistry (for example, of fixed cells or tissue sections)

for intracellular or cell-surface markers, Western blot analysis of cellular extracts, and enzyme-linked immunoassay, for cellular extracts or products secreted into the medium. Antibodies that distinguish cardiac markers like cTnI and cTnT from other isoforms are available commercially from suppliers like Sigma and Spectral Diagnostics. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods using publicly available sequence data (GenBank). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, or 50-fold above that of a control cell, such as an undifferentiated pluripotent stem cell or other unrelated cell type.

Once markers have been identified on the surface of cells of the desired phenotype, they can be used for immunoselection to further enrich the population by techniques such as immunopanning or antibody-mediated fluorescence-activated cell sorting.

Under appropriate circumstances, pluripotent stem cell-derived cardiomyocytes often show spontaneous periodic contractile activity. This means that when they are cultured in a suitable tissue culture environment with an appropriate $Ca^{2+}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between about 6 and 200 contractions per minute, and often between about 20 and about 90 contractions per minute in normal buffer. Individual cells may show spontaneous periodic contractile activity on their own, or they may show spontaneous periodic contractile activity in concert with neighboring cells in a tissue, cell aggregate, or cultured cell mass.

The contractile activity of the cells can be characterized according to the influence of culture conditions on the nature and frequency of contractions. Compounds that reduce available $Ca^{2+}$ concentration or otherwise interfere with transmembrane transport of $Ca^{2+}$ often affect contractile activity. For example, the L-type calcium channel blocker diltiazem inhibits contractile activity in a dose-dependent manner. On the other hand, adrenoceptor agonists like isoprenaline and phenylephrine have a positive chronotropic effect. Further characterization of functional properties of the cell can involve characterizing channels for $Na^-$, $K^+$, and $Ca^+$. Electrophysiology can be studied by patch clamp analysis for cardiomyocyte like action potentials. See Igelmund et al., 1999; Wobus et al., 1995; and Doevendans et al., 2000.

Functional attributes provide a manner of characterizing cells and their precursors in vitro, but may not be necessary for some of the uses referred to in this disclosure. For example, a mixed cell population enriched for cells bearing some of the markers listed above, but not all of the functional or electrophysiology properties, can be of considerable therapeutic benefit if they are capable of grafting to impaired cardiac tissue, and acquiring in vivo the functional properties needed to supplement cardiac function.

Where derived from an established line of pluripotent stem cells, the cell populations and isolated cells of this invention can be characterized as having the same genome as the line from which they are derived. This means that the chromosomal DNA will be over 90% identical between the pluripotent stem cells and the cardiac cells, which can be inferred if the cardiac cells are obtained from the undifferentiated line through the course of normal mitotic division. The characteristic that cardiomyocyte lineage cells are derived from the parent cell population is important in several respects. In particular, the undifferentiated cell population can be used for producing additional cells with a shared genome—either a further batch of cardiac cells, or another cell type that may be useful in therapy—such as a population that can pre-tolerize the patient to the histocompatibility type of the cardiac allograft (US 2002/0086005; WO 03/050251).

VII. Genetic Alteration of Differentiated Cells

The cells of this invention can be made to contain one or more genetic alterations by genetic engineering of the cells either before or after differentiation (US 2002/0168766). A cell is said to be "genetically altered" or "transgenic" when a polynucleotide has been transferred into the cell by any suitable means of artificial manipulation, or where the cell is a progeny of the originally altered cell that has inherited the polynucleotide. For example, the cells can be processed to increase their replication potential by genetically altering the cells to express telomerase reverse transcriptase, either before or after they progress to restricted developmental lineage cells or terminally differentiated cells (US 2003/0022367).

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types such as FGF, cardiotropic factors such as atrial natriuretic factor, cripto, and cardiac transcription regulation factors, such as GATA-4, Nkx2.5, and MEF2-C. Production of these factors at the site of administration may facilitate adoption of the functional phenotype, enhance the beneficial effect of the administered cell, or increase proliferation or activity of host cells neighboring the treatment site.

In certain embodiments of the invention, cells containing a nucleic acid construct of the present invention may be identified in vitro or in vivo by including a marker in the expression vector, such as a selectable or screenable Marker. Such markers would confer an identifiable change to the cell permitting easy identification of cells containing the expression vector, or help enrich or identify differentiated cardiac cells by using a cardiac-specific promoter, such as promoters of cardiac troponin I (cTnI), cardiac troponin T (cTnT), sarcomeric myosin heavy chain (MEW), GATA-4, Nkx2.5, N-cadherin, β1-adrenoceptor, ANF, the MEF-2 family of transcription factors, creatine kinase MB (CK-MB), myoglobin, or atrial natriuretic factor (ANF).

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, blasticidin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

VIII. Use of Cardiomyocytes and their Precursors

Certain aspects of this invention provide a method to produce large numbers of cells of the cardiomyocyte lineage. These cell populations can be used for a number of important research, development, and commercial purposes.

A. Drug Screening

Cardiomyocytes of this invention can be used commercially to screen for factors (such as solvents, small molecule drugs, peptides, oligonucleotides) or environmental conditions (such as culture conditions or manipulation) that affect the characteristics of such cells and their various progeny.

In some applications, pluripotent stem cells (undifferentiated or differentiated) are used to screen factors that promote maturation into later-stage cardiomyocyte precursors, or terminally differentiated cells, or to promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of this invention relate to the testing of pharmaceutical compounds for their effect on cardiac muscle tissue maintenance or repair. Screening may be done either because the compound is designed to have a pharmacological effect on the cells, or because a compound designed to have effects elsewhere may have unintended side effects on cells of this tissue type. The screening can be conducted using any of the precursor cells or terminally differentiated cells of the invention.

The reader is referred generally to the standard textbook In vitro Methods in Pharmaceutical Research, Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. $[^3H]$-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to Vickers (pp 375-410 in In vitro Methods in Pharmaceutical Research, Academic Press, 1997) for further elaboration.

Effect of cell function can be assessed using any standard assay to observe phenotype or activity of cardiomyocytes, such as marker expression, receptor binding, contractile activity, or electrophysiology—either in cell culture or in vivo. Pharmaceutical candidates can also be tested for their effect on contractile activity—such as whether they increase or decrease the extent or frequency of contraction. Where an effect is observed, the concentration of the compound can be titrated to determine the median effective dose ($ED_{50}$).

B. Animal Testing

Certain aspects of this invention also provide for the use of cardiomyocytes and their precursors to enhance tissue maintenance or repair of cardiac muscle for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether pluripotent stem cell-derived cells are still present.

This can be performed by administering cells that express a detectable label (such as green fluorescent protein, or β-galactosidase); that have been prelabeled (for example, with BrdU or $[^3H]$thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Suitability can also be determined by assessing the degree of cardiac recuperation that ensues from treatment with a cell population of cardiomyocytes derived from pluripotent stem cells. A number of animal models are available for such testing. For example, hearts can be cryoinjured by placing a precooled aluminum rod in contact with the surface of the anterior left ventricle wall (Murry et al., 1996; Reinecke et al., 1999; U.S. Pat. No. 6,099,832; Reinecke et al., 2004). In larger animals, cryoinjury can be effected by placing a 30-50 mm copper disk probe cooled in liquid N2 on the anterior wall of the left ventricle for about 20 min (Chiu et al., 1995). Infarction can be induced by ligating the left main coronary artery (Li et al., 1997). Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, and rate of pressure decay.

C. Therapeutic Use in Humans

After adequate testing, differentiated cells of this invention can be used for tissue reconstitution or regeneration in a human patient or other subject in need of such treatment.

The cells are administered in a manner that permits them to graft or migrate to the intended tissue site and reconstitute or regenerate the functionally deficient area. Special devices are available that are adapted for administering cells capable of reconstituting cardiac function directly to the chambers of the heart, the pericardium, or the interior of the cardiac muscle at the desired location.

Where desirable, the patient receiving an allograft of pluripotent stem cell-derived cardiomyocytes can be treated to reduce immune rejection of the transplanted cells. Methods contemplated include the administration of traditional immunosuppressive drugs like cyclosporin A (Dunn et al., Drugs 61:1957, 2001), or inducing immunotolerance using a matched population of pluripotent stem cell-derived cells (WO 02/44343; U.S. Pat. No. 6,280,718; WO 03/050251). Another approach is to adapt the cardiomyocyte cell population to decrease the amount of uric acid produced by the cells upon transplantation into a subject, for example, by treating them with allopurinol. Alternatively or in conjunction, the patient is prepared by administering allopurinol, or an enzyme that metabolizes uric acid, such as urate oxidase (PCT/US04/42917).

Patients suitable for receiving regenerative medicine according to this invention include those having acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, patient mobility, and quality of life.

The cardiomyocytes of this invention can be supplied in the form of a pharmaceutical composition, comprising an isotonic excipient prepared under sufficiently sterile conditions for human administration. In certain aspects, it may be desirable to disperse the cells using a protease or by gentle mechanical manipulation into a suspension of single cells or smaller clusters. To reduce the risk of cell death upon engraftment, the cells may be treated by heat shock or cultured with about 0.5 U/mL erythropoietin about 24 hours before administration.

For general principles in medicinal formulation, the reader is referred to Cell Therapy: Stem Cell Transplantation, Gene Therapy, and Cellular Immunotherapy, 1996; and Hematopoetic Stem Cell Therapy, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cardiomyocytes. Suitable ingredients include matrix proteins that support or promote adhesion of the cardiomyocytes, or complementary cell types, especially endothelial cells.

This invention also includes a reagent system, comprising a set or combination of cells that exist at any time during manufacture, distribution, or use. The cell sets comprise any combination of two or more cell populations described in this disclosure, exemplified but not limited to a type of differentiated cell (cardiomyocytes, cardiomyocyte precursors, and so on), in combination with undifferentiated pluripotent stem cells or other differentiated cell types, often sharing the same genome. Each cell type in the set may be packaged together, or in separate containers in the same facility, or at different locations, at the same or different times, under control of the same entity or different entities sharing a business relationship.

Pharmaceutical compositions of this invention may optionally be packaged in a suitable container with written instructions for a desired purpose, such as the reconstitution of cardiomyocyte cell function to improve a disease condition or abnormality of the cardiac muscle.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Single Cell Splitting for Automation

IPS cells were maintained on Matrigel™ in TeSR medium (from Stem Cell Technologies) in 6-well plates. After the media were aspirated, 1 ml/well of 0.05% Trypsin was added and the cells were incubated at 37° C. for 7 minutes. Equal volume of A1 media (TeSR media containing 1 μM H-1152 (or HA-100) (EMD), 0.5 mg/ml Soybean Trypsin inhibitor (Invitrogen)) were added to the cells. Then the cells were seeded into Matrigel™-coated vessels containing the A1 media and fed every 24 hours with TeSR media.

Example 2

Single Human IPS Cell Passaging with NaCitrate

Dissociated iPS cells were rinsed with D-PBS (Dulbecco's Phosphate Buffered Saline) free of $Ca^{2+}$ and $Mg^{2+}$ and the media were aspirated. The cells were then incubated with appropriate amount (i.e., 1 mL for one well of 6-well plate, 15 mL for T-150 flask, etc) of 15 mM NaCitrate, 165 mM KCl, pH 7.3, OSM 340, at room temperature for 6-15 minutes. After incubation, the NaCitrate solution were aspirated with the cells still loosely attached. The cells were resuspended in appropriate amount of TeSR with 1 μM H1152 and distributed to Matrigel™ surfaced vessel.

Figure 3:
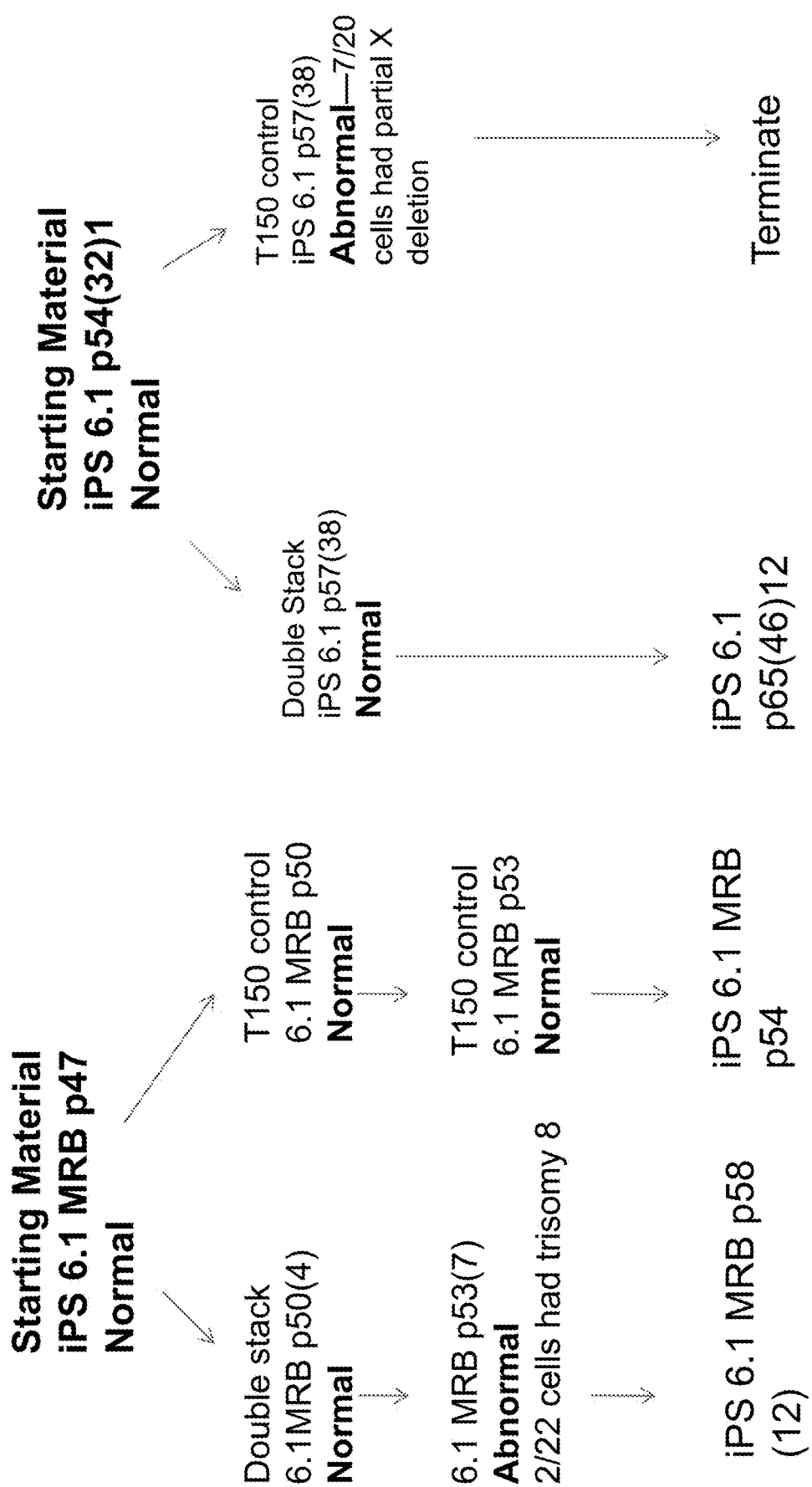
FIG. 3: Karyotype testing results performed on both iPS6.1 and iPS6.1 MRB's that were maintained in Double Stacks split with NaCitrate.
Figures 6A, 6B:
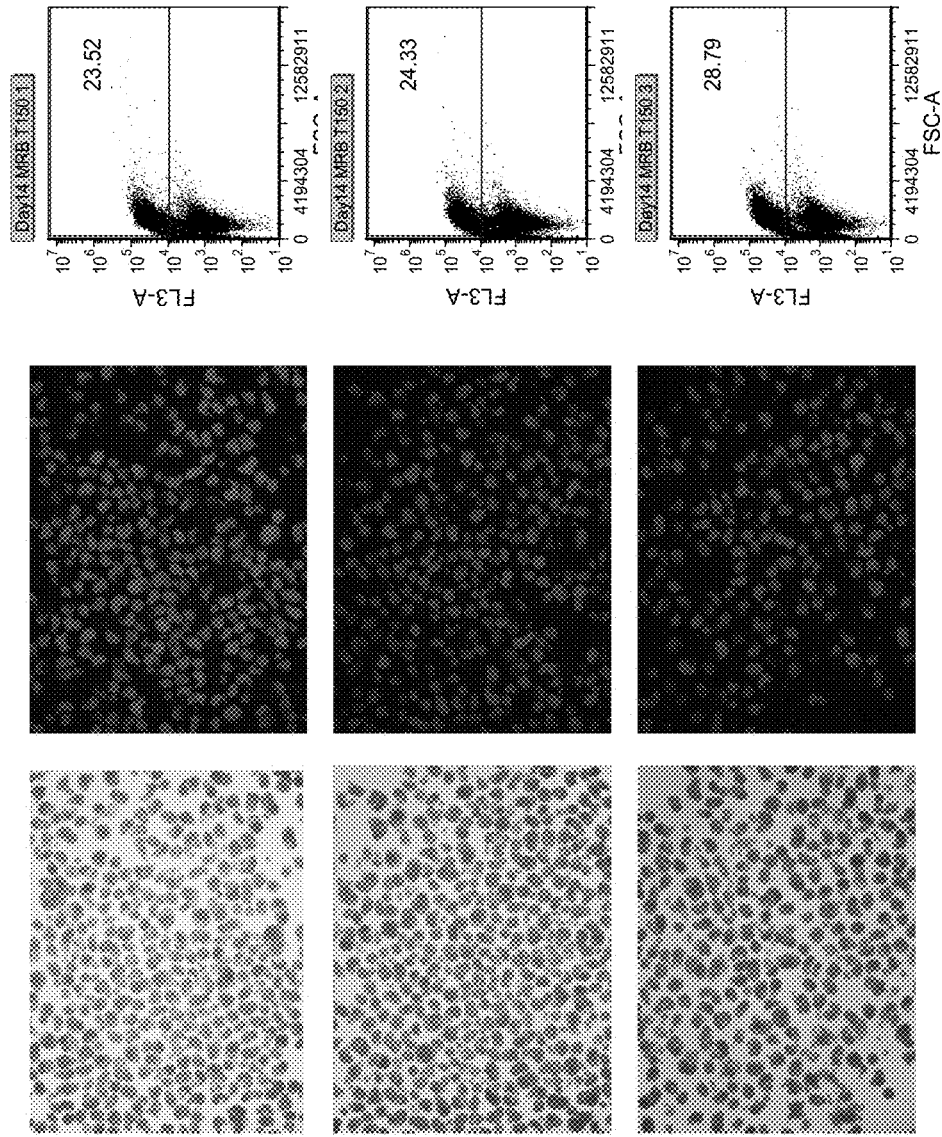
FIGS. 6A-B: Aggregates (Day 14) formed from IPS6.1 MRB cells in T150 flask.

For scale up production of the starting material from T150 flasks to Corning Double Stacks, and for assessment of the ability of iPS cells to be passaged as single cells/small clumps with NaCitrate, iPS 6.1 and iPS 6.1 MRB were passaged with 15 mM NaCitrate as single cells or small cell clumps into double stacks while maintaining T150 control flasks split with dispase (see FIG. 1 for experimental design). The Double Stack NaCitrate conditions had a good typical doubling time of ~30 hrs (FIGS. 2A-C). Cells were assessed at passage 4 and passage 7 with cardiogenesis, pluripotency panel, and karyotype. Cells were split 4 times with NaCitrate and maintained a normal karyotype (FIG. 3). Aggregate images and cTnT staining for cardiomyocytes were analyzed on day 14 after splitting (FIGS. 4A-D, FIGS. 5A-C, FIGS. 6A-B, FIGS. 7A-C). Pluripotency profiles of iPS cells after passaging with NaCitrate and dispase was compared by flow cytometry using five pluripotency markers (FIGS. 8A-C). It appears safe to passage iPS cells at least four times with the NaCitrate method.

Cardiogenesis was also analyzed for those iPS cells after passaging with NaCitrate and data were compiled in FIG. 9. The figure shows the cardiomyocytes generated from iPS6.1 and iPS6.1 MRB cells passaged normally with dispase in T150 flasks (control) as well as cells passaged in Double stacks with NaCitrate. The last three "spinner" samples come from Double Stack iPS 6.1 MRB cells that were left over from various Double stack harvests. An average yield of 110e6 cells/L was obtained in 1 L spinner with cells passaged in double stacks with NaCitrate.

The experiments and data described above support the use of NaCitrate as a means to split iPS cells such as iPS 6.1 and iPS 6.1 MRB. Combining this split method with Double Stack flasks will allow more simple and efficient production of large quantities of starting material. NaCitrate split cells spread out much more evenly and the cells can be grown to more of a monolayer than cells split with dispase. This allows the inventors to maximize both the surface area and TeSR usage/cell for each flask. NaCitrate also solves the problem of needing top access to the cells in order to scrape them off when using dispase. It appears the inventors can safely passage iPS cells at least 4 times with NaCitrate (from dispase maintained cells) and still have the cells which maintain normal karyotype, cardiogenic potential, and pluripotency.

Example 3

Induction of IPS Cells into Cardiomyocytes Via Suspension Aggregates in a 1 L Spinner Flask Human pluripotent stem cells were maintained and expanded on Matrigel™ in TeSR medium into cardiomyocytes via suspension aggregates in a 1 L spinner flask as in the following experiments.

IPS-MRB cells were maintained on Matrigel™ in TeSR medium (from Stem Cell Technologies) no later than when they would normally be ready to be passaged. IPS cells were grown in T-150 flasks throughout this example, but can be scaled for starting cells in other culture formats. Five T-150 flasks of iPS cells were harvested: media were aspirated and cells were incubated with 12 mL room temperature TrypLe™ (Invitrogen), a recombinant typsin-like enzyme, at 37° C. for 7 minutes. The cells were then transferred to five 50 ml conical tubes (one tube for each T-150 flask) containing 12 ml DMEM/F12 (GIBCO) with 10% fetal calf serum (FCS) (Chemicon). The cells were then pelleted at 1200 rpm for 5 minutes and supernatant aspirated. The pellet was resuspended in 10 mL aggregate promotion medium (TeSR medium containing 25 μg/ml Gentamicin, 1 μM H1152, and with or without 50 ng/ml human recombinant HGF). The resuspended pellet were combined into a single 250 ml conical tube (allowing volume for later dilution), if necessary. Cells were counted using CEDEX HiRES cell counter and then diluted to $1.0 \times 10^6$ cells/mL. Each 500 mL diluted cell stock was dispensed into one 1 L spinner flask (leaving room in spinner flasks for later dilution) and the flasks were placed on magnetic stir platform with a speed of 50 RPM (both side caps were loosed by two full turns to allow gas transfer).

On the next day (Day 1), flasks containing the cells were set in cell culture hood and suspended aggregate allowed to settle to the bottom of the flasks for 30 minutes. The spent media were aspirated using a 2 mL aspirating pipet with approximately 100 mL left in the flasks (if films of cells form on bottom after setting, shake flask back and forth in each direction to break them up before adding medium). Aggregate transition medium (50% TeSR medium, 45% DMEM containing GlutaMax™, 5% ES-qualified FCS, 25 μg/ml Gentamicin, 1 μM H1152, and with or without 50 ng/ml HGF) were added to the flasks using Pipeline machine to bring to the original volume. The flasks were returned to the stirring platform inside a 7% $CO_2$ incubator and the agitator was started to operate at 50±1 RPM (both side caps were loosed by two full turns to allow gas transfer).

On Day 2, flasks containing the cells were set in cell culture hood and suspended aggregate allowed to settle to the bottom of the flasks for 15 minutes. The spent media were aspirated with approximately 100 mL left in the flasks. Aggregate suspension were gently mixed in flasks, and cardiac induction medium (90% TeSR medim, 10% ES-qualified FCS, 25 μg/ml Gentamicin, 50 ng/ml human recombinant bFGF, and with or without 50 ng/ml human recombinant HGF) were added to each flask to 1 L (2× dilution) with Pipeline machine. The flasks were returned to the stirring platform inside a 7% $CO_2$ incubator and the agitator was started to operate at 50±1 RPM (both side caps were loosed by two full turns to allow gas transfer).

On Day 3, flasks containing the cells were set in cell culture hood and suspended aggregate allowed to settle to the bottom of the flasks for 15 minutes. The spent media were aspirated with approximately 100 mL left in the flasks. Spinner flasks were shaken back and forth to break large clumps. Cardiac induction medium were added back to each flask to bring back to the original volume for Days 3-7; cardiac maintenance medium were exchanged instead for Days 8, 10, 12. After every media exchange, the flasks were returned to the stirring platform inside a 7% $CO_2$ incubator and the agitator was started to operate at 50±1 RPM (both side caps were loosed by two full turns to allow gas transfer).

Cell cultures were analyzed on Day 14 by total cell counting per flask at harvest, cTNT or RFP purity at harvest. Aggregate count was also carried on Day 2 and final stage and aggregate pictures were taken.

Example 4

Induction of IPS Cells into Cardiomyocytes Via Suspension Aggregates in T-Flasks IPS or hES cells (either iPS6.1 cells, iPS6.1-MRB cells, or H9-TGZ cells) were maintained on Matrigel™ in TeSR medium (from Stem Cell Technologies) no later than when they would normally be ready to be passaged. The starting cells were grown in T-150 flasks, but could be scaled in other culture formats.

Figure 10A:
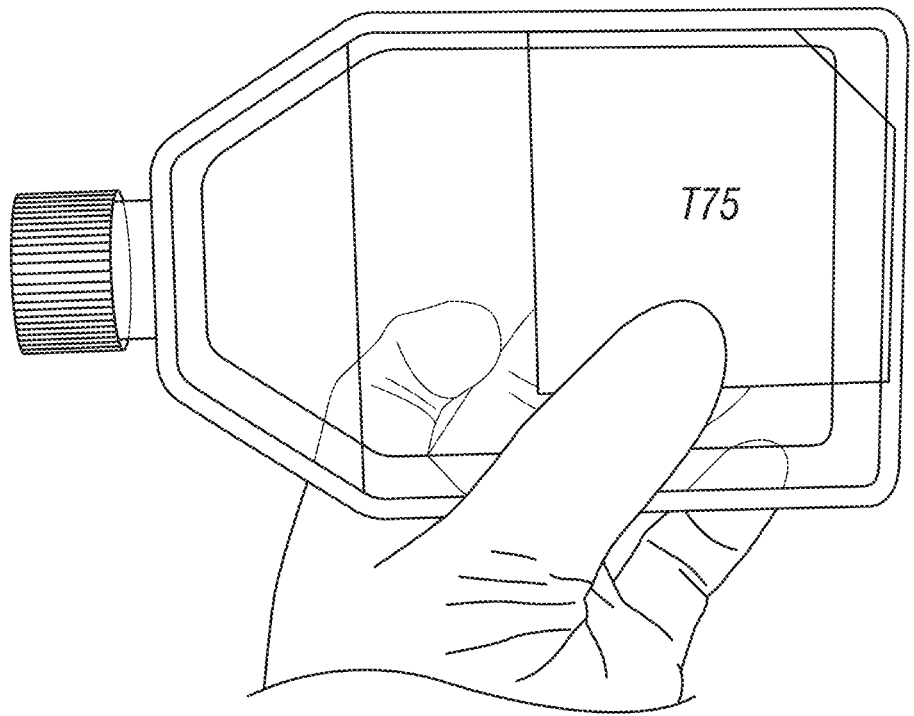
FIGS. 10A-B: Illustration of marking of feeding line in flasks.
Figure 10B:
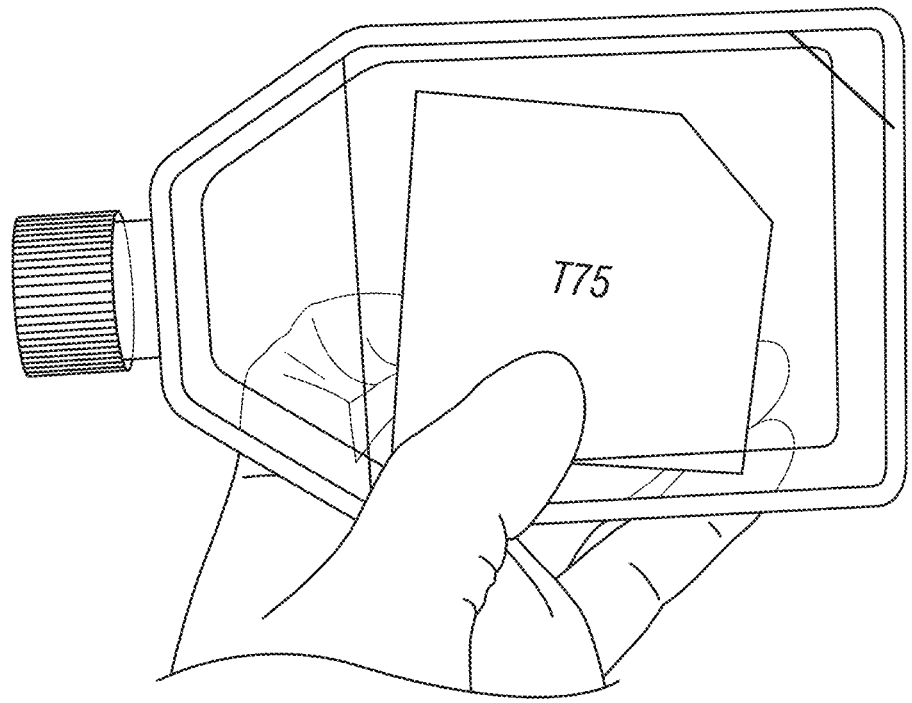

For aggregate formation on the first day (Day 0), ultra low attachment (ULA) T75 or T25 flasks by marking feeding line were prepared. A feeding line marking template was placed against the raised edge on the top side of a low attachment flask (FIG. 10A) and a line was drawn on the flask with a permanent (alcohol resistant) marker (FIG. 10B). The flask were labeled then.

Up to five T150 flasks of cells were harvested at a time: cells were examined and verified to be 60-80% confluent. Media were aspirated and 12 mL room temperature TrypLE were added to incubate at 37° C. for 7 minutes. Meanwhile, one 50 mL conical tube was prepared for each T150 by adding 12 mL DMEM/F12 with 10% FCS. After 7 minute incubation, the flasks were tapped to dislodge residual cells and cells were pipetted into prepared 50 mL tubes. Cells were then pelleted at 1200 rpm, 5 minutes using centrifuge and supernatant was aspirated without disturbing the cell pellet. The cell pellet were resuspended in 10 mL aggregate formation medium as described in Example 3.

Multiple tubes of cells were combined into a single 250 mL conical tube (allowing volume for later dilution), if necessary. Cells were counted using CEDEX HiRES cell counter according to SOP EQ-15 and then diluted to $1.0 \times 10^6$ cells per mL. Each 15 mL diluted cell stock was dispensed into each ULA T75 (or 5 mL per ULA T25) flask.

The flasks/plates were placed on rocker platform inside 7% $CO_2$ incubator to incubate for 24±4 hrs. Be sure rocker is well-balanced. The rocker was started with the agitator operating at 7.5±2 RPM for T75 flasks or 15±1 RPM for T25 flasks. To measure rocker RPM, a clock or timer was used to keep time, and the number of complete cycles was counted in 60 seconds. The rotary speed was adjusted and re-measured until RPM reading falls within specifications. Re-measurement and readjustment were performed as necessary anytime flasks were added or removed.

Figure 11A:
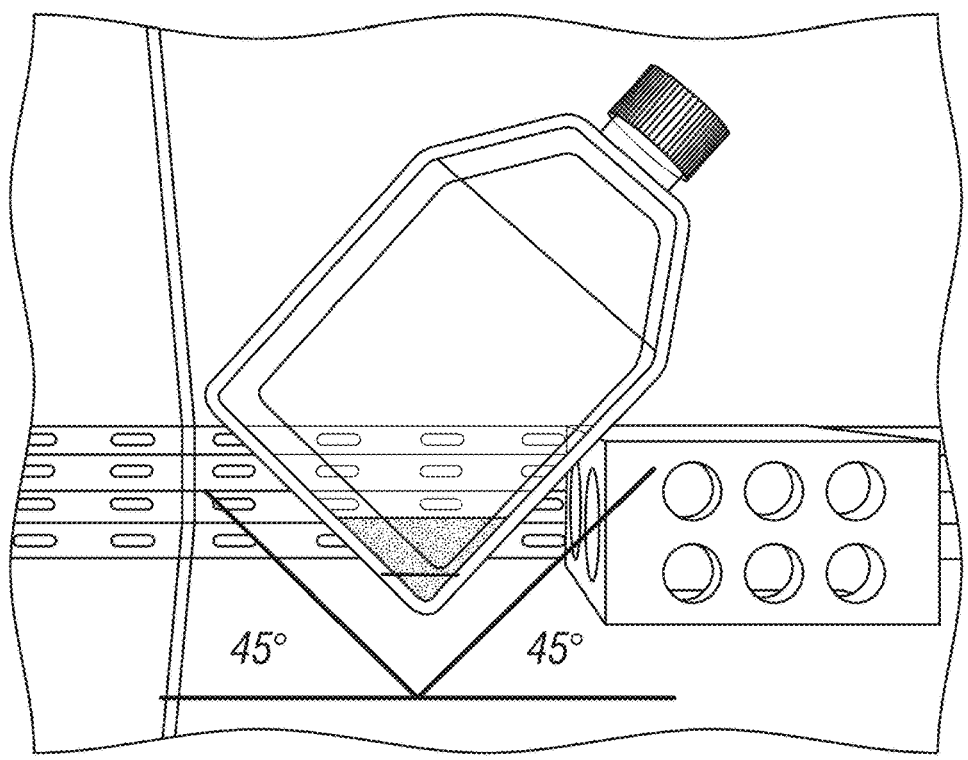
FIGS. 11A-B: Illustration of aspiration of media from flasks.
Figure 11B:
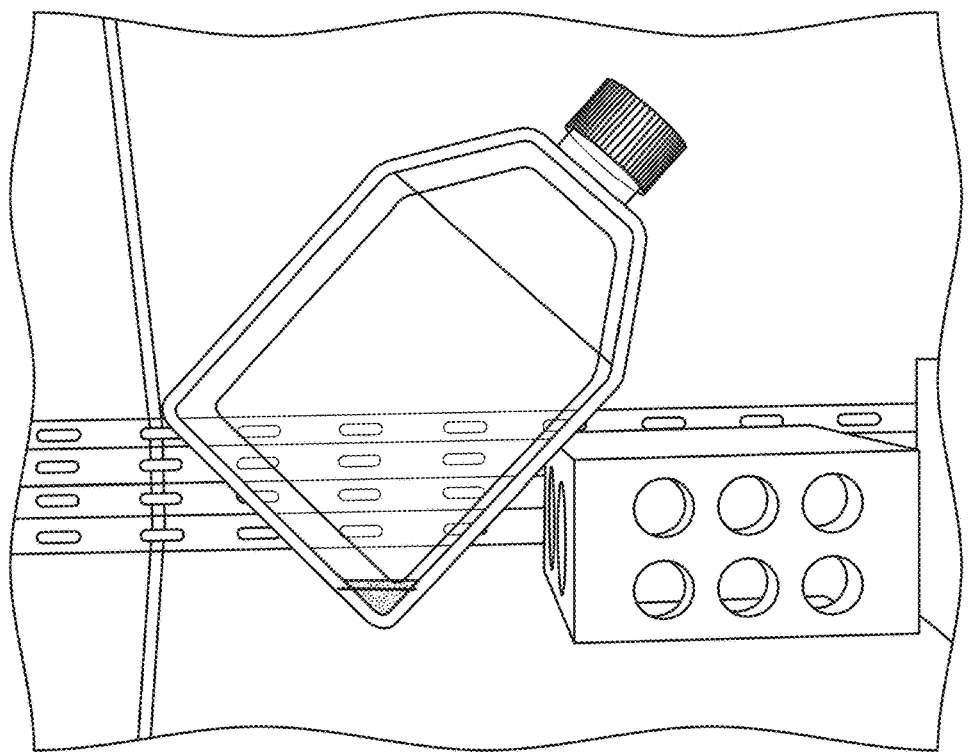

The next day (Day 1) the cells were fed aggregate transition media: cells were fed by tilting flask on short edge at a 45° angle as shown in FIG. 11A and suspended aggregates were allowed to settle to the bottom corner of the flask for 10 minutes. Spent media were aspirated with a Pasteur pipet down to the feeding line drawn on the flask (FIG. 11B). Care should be taken to prevent scratching the low attachment surface of the flask with the pipet as aggregates could stick to the damaged surface. The flask was turned upright and 15 mL/T75 (or 5 mL/T25) flask was gently added the Aggregate Transition Medium.

The flasks/plates were placed on rocker platform inside 7% $CO_2$ incubator to incubate for 24±4 hrs. The rocker was started with the agitator operating at 7.5±2 RPM for T75 flasks or 15±1 RPM for T25 flasks. Rotary speed was adjusted as described above.

On Day 2, cells were diluted and distributed to T25 or T75 flasks. First, additional ULA T25 or T75 flasks were prepared by marking feeding line as described above and labeling. Cells were fed by tilting flask on short edge at a 45° angle as shown in FIG. 11A and suspended aggregates were allowed to settle to the bottom corner of the flask for 10 minutes. Spent media were aspirated with a Pasteur pipet down to the feeding line drawn on the flask (FIG. 11B). The flask was turned upright and 15 mL/T75 (or 5 mL/T25) flask was gently added appropriate volume of cardiac induction medium (30 ml for T75 flask or 10 ml for T25 flask). If large clumps of cells have formed, the resuspended aggregates may be filtered through a 200 um sterile mesh filter into a 50 mL conical tube before proceeding.

Then the cells were distributed to appropriate sized flasks. If seeding to T25 flasks: 5 mL of thoroughly resuspended aggregates were transferred to each of six T25 flasks. The goal is to seed the aggregates formed from 2.5 million cells into each T25 (i.e., 0.5 million cells per mL). Do not correct for cell survival or aggregate number. If seeding to T75 flasks: 15 mL of thoroughly resuspended aggregates were transferred to each of two T75 flasks. The goal is to seed the aggregates formed from 7.5 million cells into each T75 (i.e., 0.5 million cells per mL). Do not correct for cell survival or aggregate number.

The flasks/plates were placed on rocker platform inside 7% $CO_2$ incubator to incubate for 24±4 hrs. The rocker was started with the agitator operating at 7.5±2 RPM for T75 flasks or 15±1 RPM for T25 flasks. Rotary speed was adjusted as described above.

On Day 3-13, cells were by tilting flask on short edge at a 45° angle as shown in FIG. 11A and allow suspended aggregates to settle to the bottom corner of the flask for 10 minutes. Spent media were aspirated with a Pasteur pipet down to the feeding line drawn on the flask (FIG. 11B).

The flask was turned upright and gently added the media (5 mL media per T25 flask or 15 mL media per T75 flask) described below: Days 3, 4, 5, 6, 7: Cardiac Induction Medium; Days 8, 10, 12: Cardiac Maintenance Medium The flasks/plates were placed on rocker platform inside 7% $CO_2$ incubator to incubate for 24±4 hrs. The rocker was started with the agitator operating at 7.5±2 RPM for T75 flasks or 15±1 RPM for T25 flasks. Rotary speed was adjusted as described above.

Cultures of cells were be terminated and analyzed on day 14: total cell count per flask at harvest, cTNT purity (or GFP purity) were analyzed at harvest. Aggregates were counted and imaged on Day 2 and at harvest.

Example 5

Aggregate Formation

Figure 12:
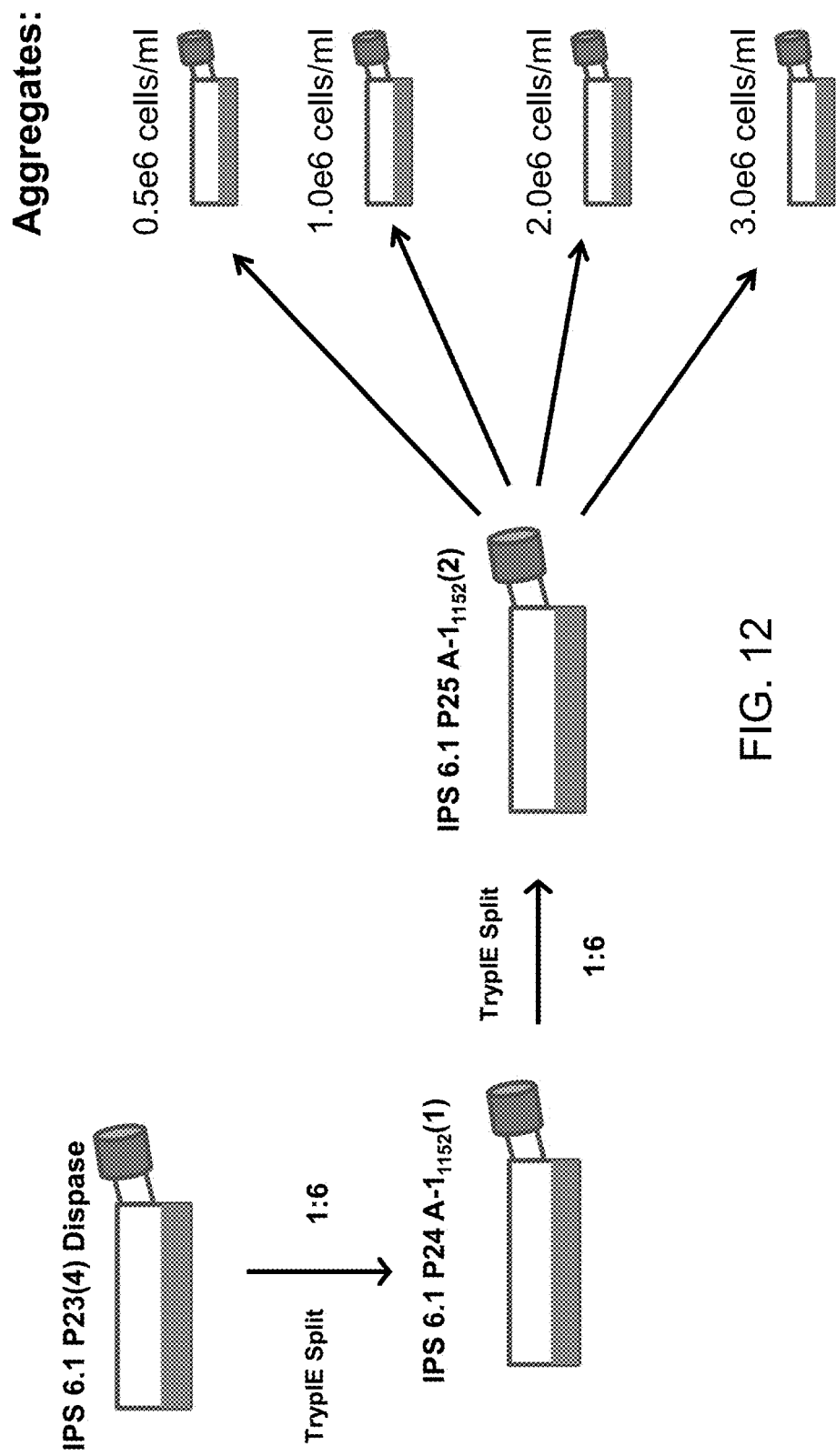
FIG. 12: IPS single cell density experimental design.
Figure 13B:
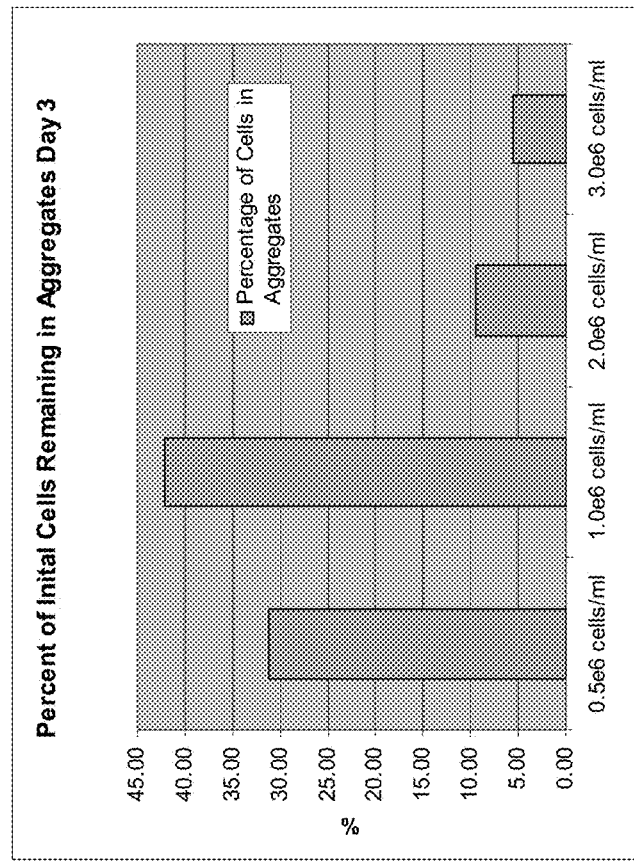
FIGS. 13A-B: Count of initial iPS cells incorporated into aggregates.
Figure 13A:
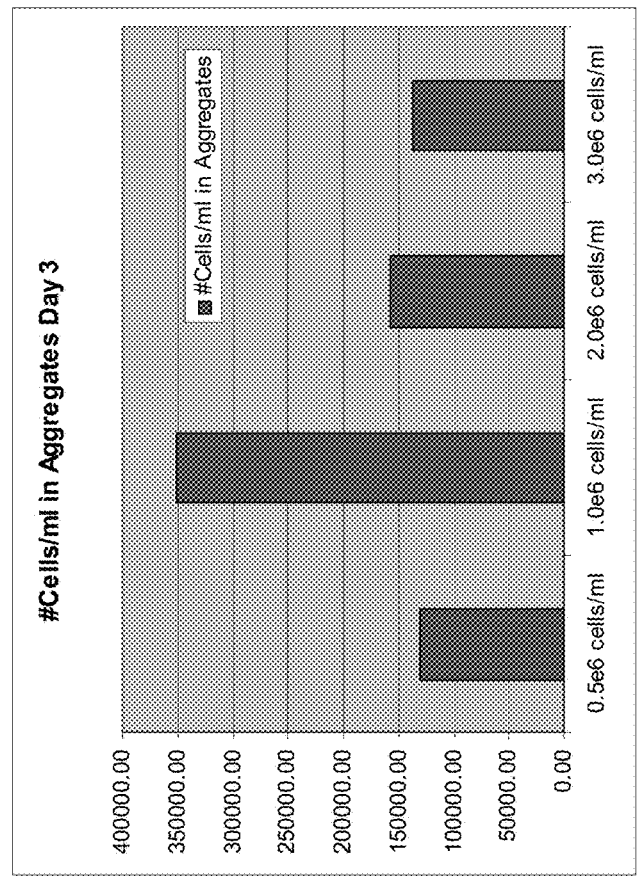
Figure 16B:
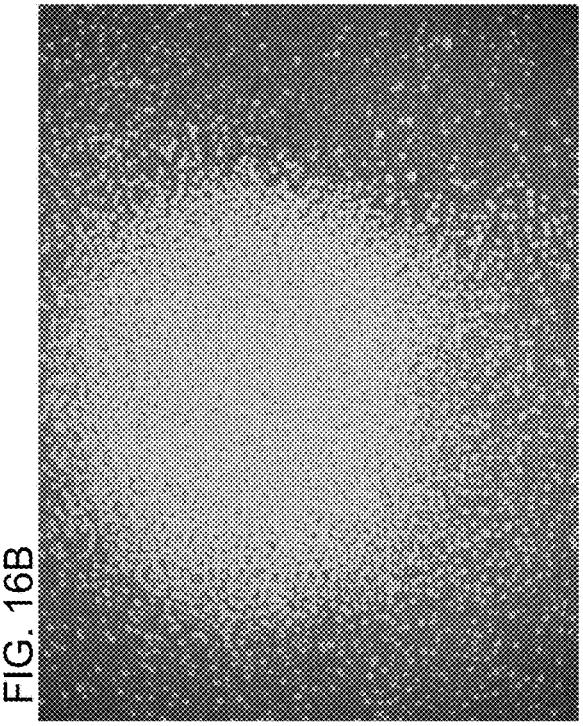
FIGS. 16A-C: Images of iPS cells in rotary culture.
Figure 16A:
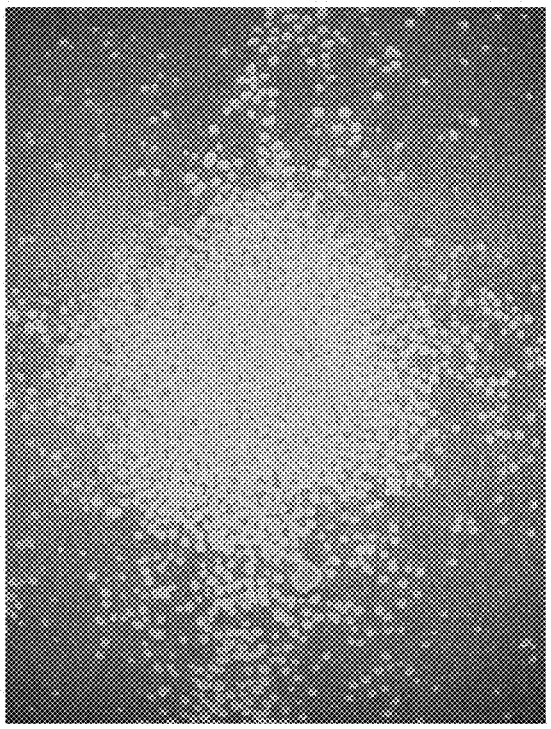
Figure 16C:
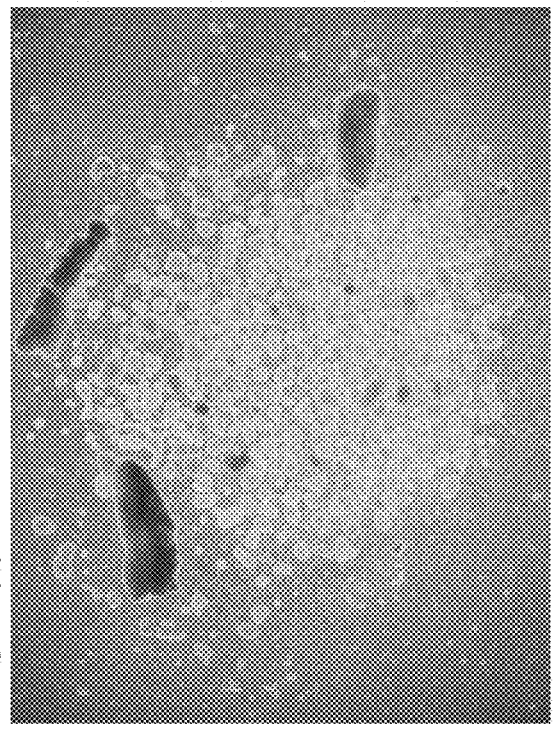

IPS cells were treated with dispase and then incubated with TrypLe™ (Invitrogen) to dissociate cells. Dissociated iPS cells were split and passaged by 1:6 dilution. The TrypLe™ split and passaging was repeated once. Four densities of iPS cells were seeded for aggregate formation: $0.5 \times 10^6$, $1 \times 10^6$, $2 \times 10^6$, and $3 \times 10^6$ cells/ml (FIG. 12). Aggregate formation and cardiac induction procedures of those iPS cells at different initial densities were performed essentially the same as described in Examples 4. Step yield (i.e., percentage of cells incorporated into aggregates), aggregate size, yield of cardiac cells are measured and detected in FIGS. 13-17. Aggregate formation at different rotary speed were also compared as in Table 2 below.

TABLE 2

Aggregate Formation and Rotary Speed

| | Spinner #1 | Spinner #2 | P-Value |
|---|---|---|---|
| Spinner speed on day 0 | 50 rpm | 70 rpm | |
| # of samples (with area between 50 μm² and 1000 μm²) | 171 | 151 | |
| Average Area (μm²) | 235.32 | 137.44371 | |
| STD AREA (μm²) | 124.55897 | 94.20054 | 2.36234E-14 |

Previous experiments by the inventors that used ROCK inhibitors and trypsin to form aggregates from H1 and IPS cells combined with single cell splitting techniques, showed proof of principle that it is possible to form beating cardiomyocytes in a suspension culture using single cells. This information led to the designation of experiments with the goal to develop an aggregate formation method with high throughput and high step-yield (i.e. percentage of cells incorporated into aggregates) using iPS cells. The purpose of the following experiments is to show that the ROCK inhibitor $H_{1152}$ allows IPS cells, individualized with TrypLE, to self aggregate, and to form cardiomyocytes in cardiac differentiation media.

Critical reagents were obtained from the following sources: DMEM and Glutamax were from Gibco (#10567); fetal calf serum was from Chemicon (# ES-009B); human recombinant HGF (hrHGF) and human recombinant basic FGF were from the R&D systems (234-FSE and 294-HGN, respectively). Gentamicin was from Gibco (#15750). $H_{1152}$ was from Calbiochem (#55550).

Figure 18:
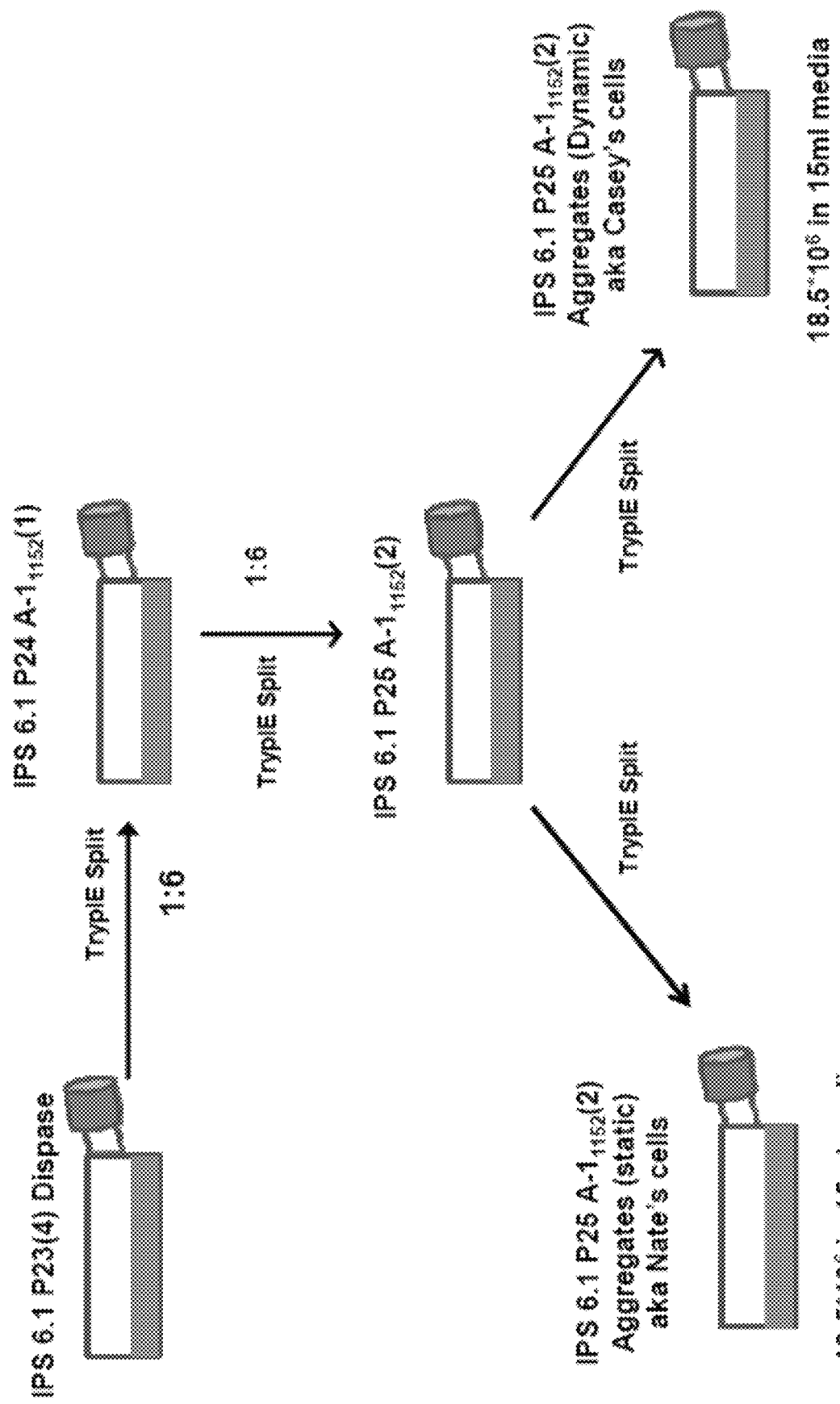
FIG. 18: Experimental Design 1 of single cell aggregate formation for cardiomyocyte formation in $H_{1152}$.
Figure 19:
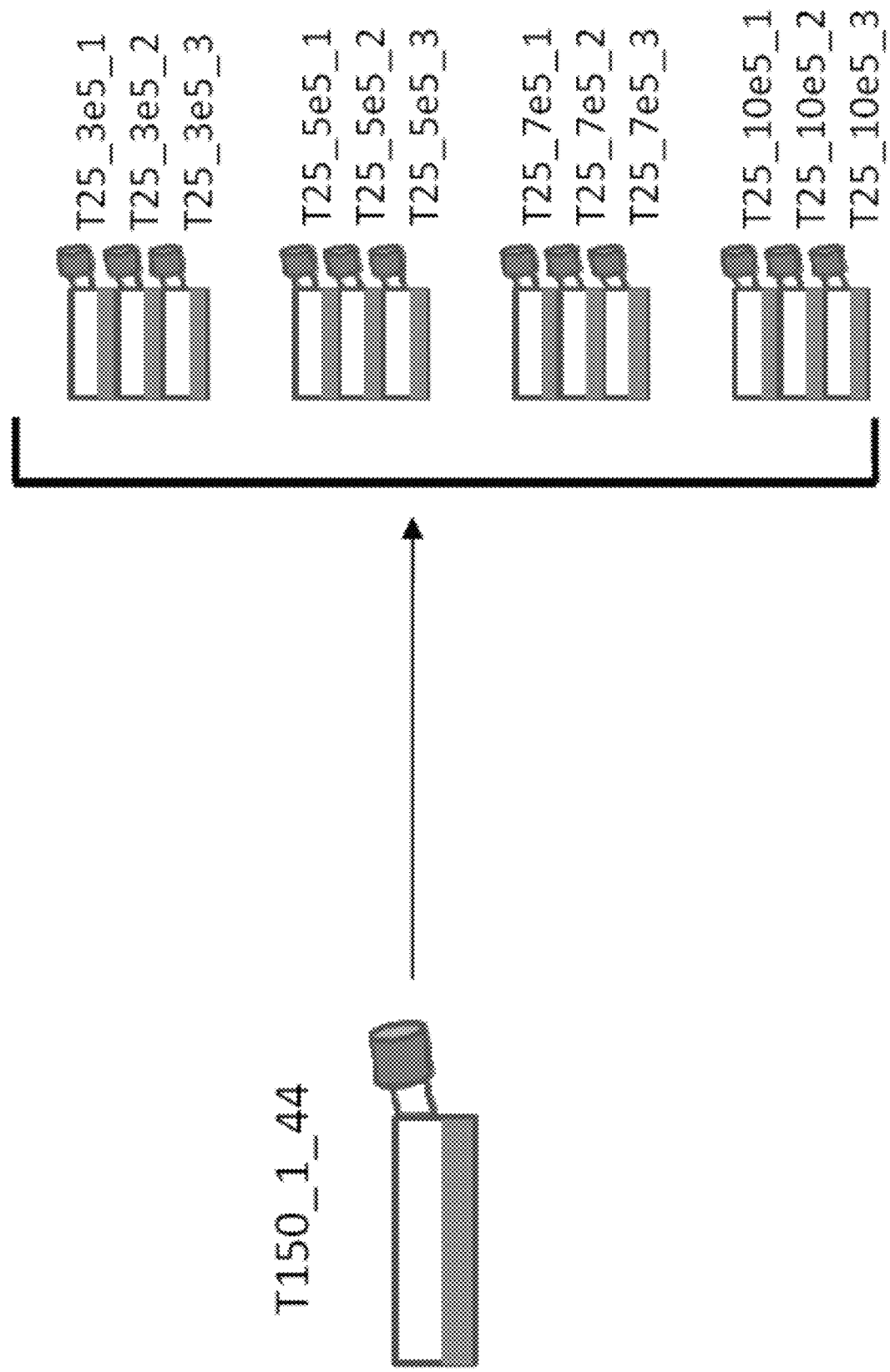
FIG. 19: Experimental Design 2 of aggregate formation for cardiomyocyte formation using cells maintained with dispase.

The first experiment (Experiment 1, see FIG. 18) described in this Example showed the potential of the single cell aggregate formation method for cardiomyocyte differentiation. The second experiment (Experiment 2, see FIG. 19) showed the potential of single cell aggregates using cells maintained with dispase. Cardiomyocyte differentiation conditions are summarized in Table 3-4 and 5-6 for Experiment 1 and 2, respectively.

TABLE 3

Summary of Cardiomyocyte differentiation conditions in Experiment 1

| Conditions | Dissociation Reagent | Cell Number per Vessel | Vessel | Notes |
| --- | --- | --- | --- | --- |
| Static | TrypLE trypsin | 18.5e6 | T75 | Static, NAB cultured, assayed day 15 |
| Dynamic | TrypLE trypsin | 18.5e6 | T75 | Placed on rotator after 2 hours, CS cultured cells after day 0, assayed day 15 |

TABLE 4

Experimental Parameters form Experiment 1

| Parameter | Method | Timepoint |
| --- | --- | --- |
| Cell morphology | Phase contract microscopy | Day1, day 3, and day 15 at end of cardio process |
| Cell Counts | Cell count by Cedex | End of the cardio process |
| Cardiomyocyte differentiation | Flow cytometry | End of the cardio process |

TABLE 5

Summary of Cardiomyocyte differentiation conditions in Experiment 2

| Conditions | Dissociation Reagent | Cell Number per Vessel | Vessel | Notes |
| --- | --- | --- | --- | --- |
| 3e5 cells/ml | TrypLE trypsin | 1.5e6 | T25 | One day Static, then agitated |
| 5e5 cells/ml | TrypLE trypsin | 2.5e6 | T25 | One day Static, then agitated |
| 7e5 cells/ml | TrypLE trypsin | 3.75e6 | T25 | One day Static, then agitated |
| 10e5 cells/ml | TrypLE trypsin | 5e6 | T25 | One day Static, then agitated |

TABLE 6

Experimental Parameters form Experiment 2

| Parameter | Method | Timepoint |
| --- | --- | --- |
| Cell morphology | Phase contrast microscopy | Day 8, also aggregate counts before each feeding |
| Cell Counts | Cell count by Cedex | End of the cardio process |
| Cardiomyocyte differentiation | Flow cytometry | End of the cardio process |

Figure 21:
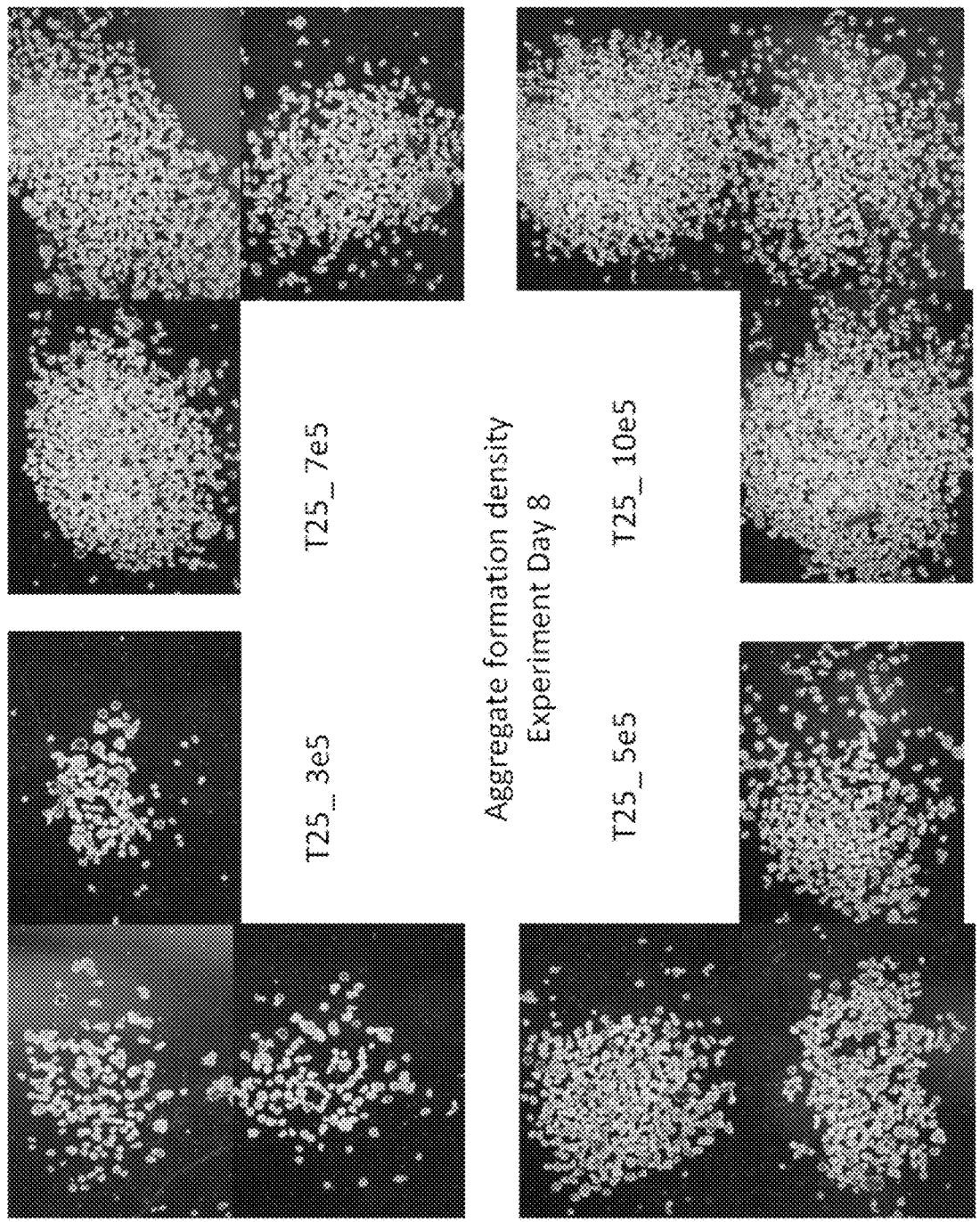
FIG. 21: Aggregate formation images from Experimental Design 2 of aggregate formation for cardiomyocyte formation using cells maintained with dispase.

Cell morphology and aggregate pictures from Experiment 1 and 2 were shown in FIGS. 20-21, respectively. After 1 day in aggregate formation media aggregation of the IPS cells was clearly visible, these aggregates tended to be more uniform in size then aggregates form using the dispase method. The data presented in FIGS. 20-21 show consistent aggregate formation across different seeding densities and between cells maintained as single cells and those with dispase.

Cells were also counted for both experiments (Tables 7-8) and the cell count represented number of cell per flask on day 15 at the end of the differentiation process.

TABLE 7

Cell/aggregate counts from Experiment 1

| | Aggregates/ T75 flask | Cells/ Aggregate | Total Cells/T75 Flask |
| --- | --- | --- | --- |
| Agitated | 739 ± 155 | 3112 | $2.3 * 10^6$ |
| Static | 4140 ± 945 | 1787 | $7.4 * 10^6$ |

TABLE 8

Average cell counts from Experiment 2

| | Average Cell Count per flask (in millions) |
| --- | --- |
| T25_3e5 | 0.112 ± 0.129 |
| T25_5e5 | 0.343 ± 0.161 |
| T25_7e5 | 0.587 ± 0.333 |
| T25_10e5 | 0.951 ± 0.229 |

Cardiomyocyte differentiation was also analyzed by using Troponin T staining (Tables 9-10). Troponin T results represented the number of cardiomyocytes per flask on day 15 at the end of the differentiation process.

TABLE 9

Cardiomyocyte differentiation from Experiment 1

| | Percent Troponin T+ Day 15 (replicate 1) | Percent Troponin T+ Day 15 (replicate 2) | Percent MF20+ Day 15 (replicate 1) | Percent MF20+ Day 15 (replicate 2) |
| --- | --- | --- | --- | --- |
| Static | 1.07 | 0.94 | 1.02 | 0.96 |
| Agitated | 9.01 | 8.77 | 6.99 | 7.36 |

TABLE 10

Cardiomyocyte differentiation from Experiment 2

| | Average Cell Count per flask (in millions) | Average % troponin T+ | Average Cardiomyocyte Yield | Average ratio iPS to CM | Average # cTnT Cells/Liter* |
|---|---|---|---|---|---|
| T25_3e5 | 0.112 ± 0.129 | 11.66 ± 1.86 | 11726 ± 12908 | 491 ± 639 | 1.95e6 ± 2.15e6 |
| T25_5e5 | 0.343 ± 0.161 | 11.87 ± 1.60 | 40227 ± 17737 | 75 ± 44 | 6.70e6 ± 2.95e6 |
| T25_7e5 | 0.587 ± 0.333 | 7.07 ± 0.74 | 40200 ± 19175 | 98 ± 47 | 6.69e6 ± 3.19e6 |
| T25_10e5 | 0.951 ± 0.229 | 5.53 ± 0.33 | 52723 ± 14268 | 99 ± 25 | 8.78e6 ± 2.37e6 |

The experiments shown in this Example demonstrated the potential of single cell aggregate formation in the cardiomyocytes differentiation. Using single cells allows for easy quantification of the number of cell put into the differentiation system allowing for further optimization of cell seeding density, and more control over the differentiation process. The data from the experiments show that the cardiomyocytes yield is equal to or greater than data from the dispase method. The use of H1152 and TrypLE allows for a scalable high throughput method of aggregate formation.

Example 6

$H_{1152}$ Duration and Aggregate Formation

Figure 22:
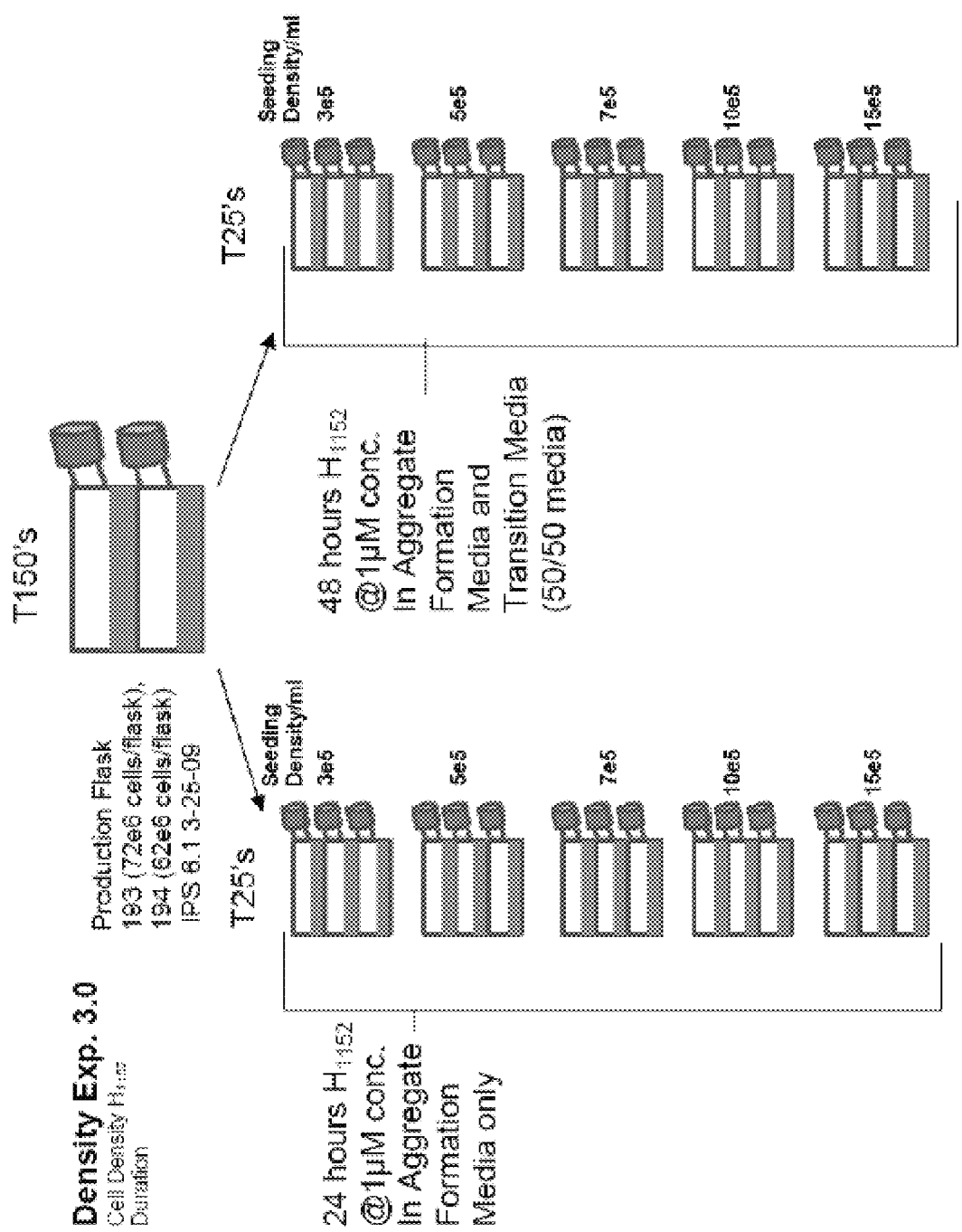
FIG. 22: Experimental 1 of testing duration of $H_{1152}$ and aggregate formation.
Figure 23:
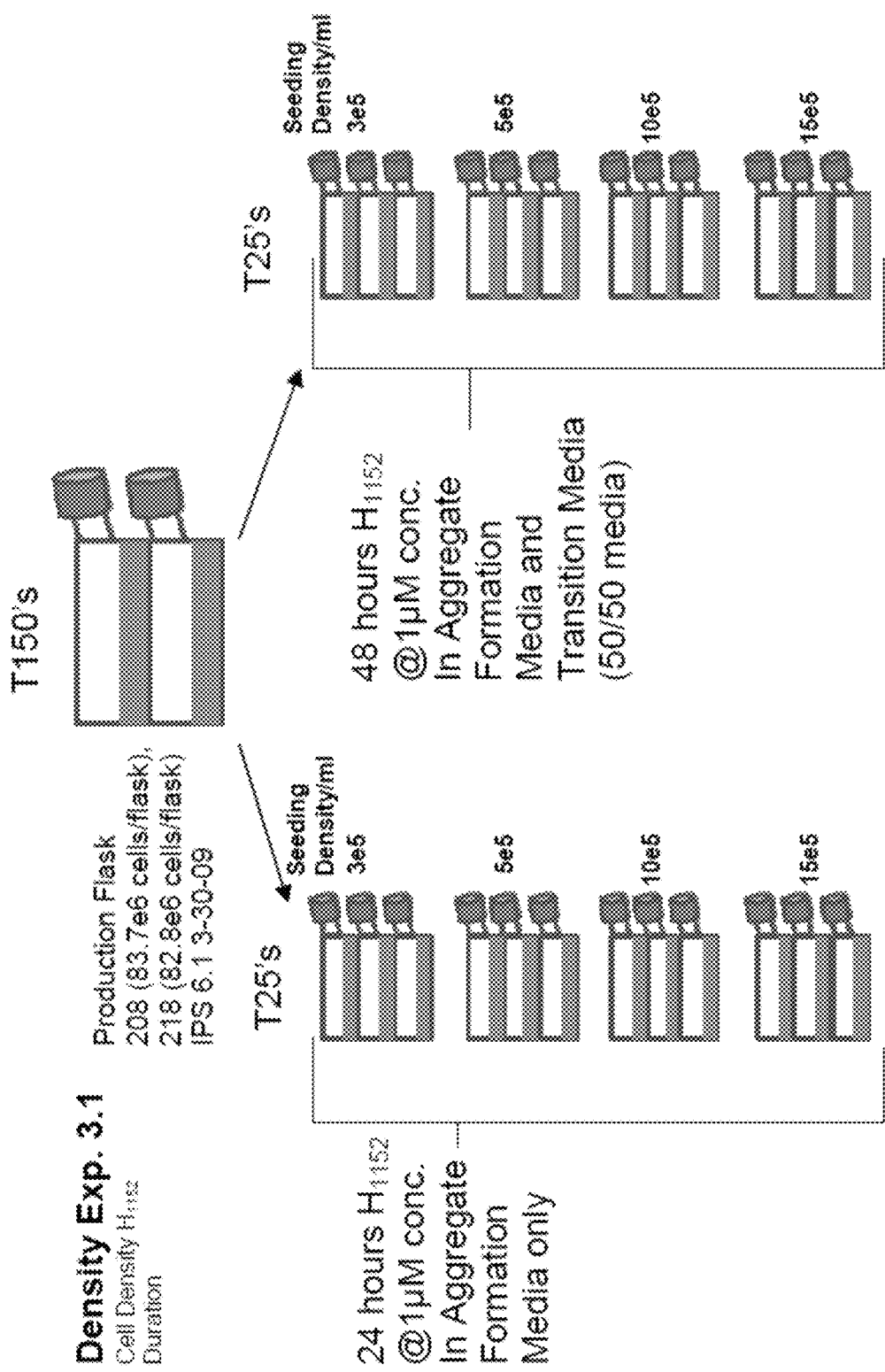
FIG. 23: Experimental 2 of testing duration of $H_{1152}$ and aggregate formation.
Figure 25:
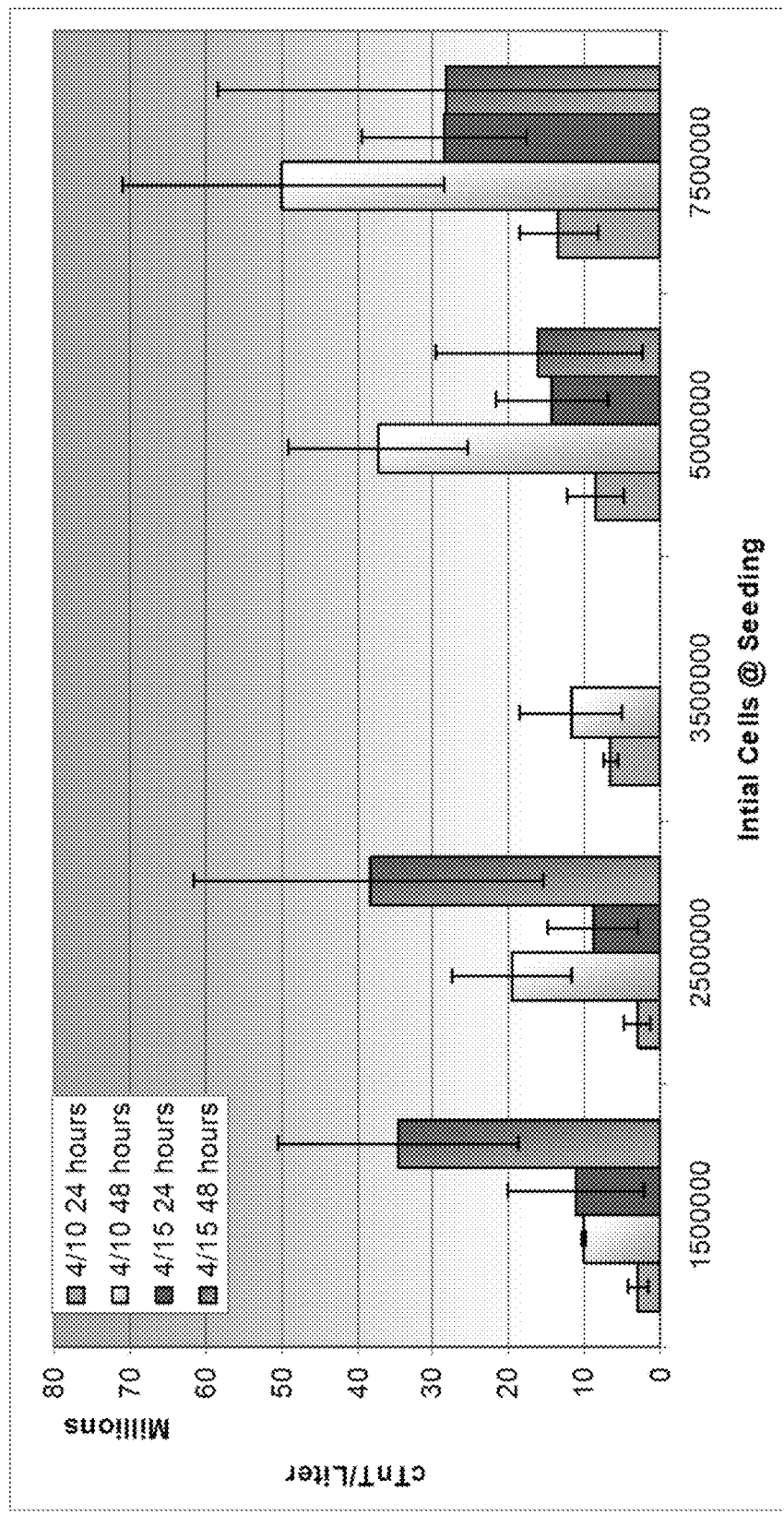
FIG. 25: Repeated results to show benefits of $H_{1152}$ for cardiac cell production in conditions containing $H_{1152}$ for 48 hours.
Figure 26:
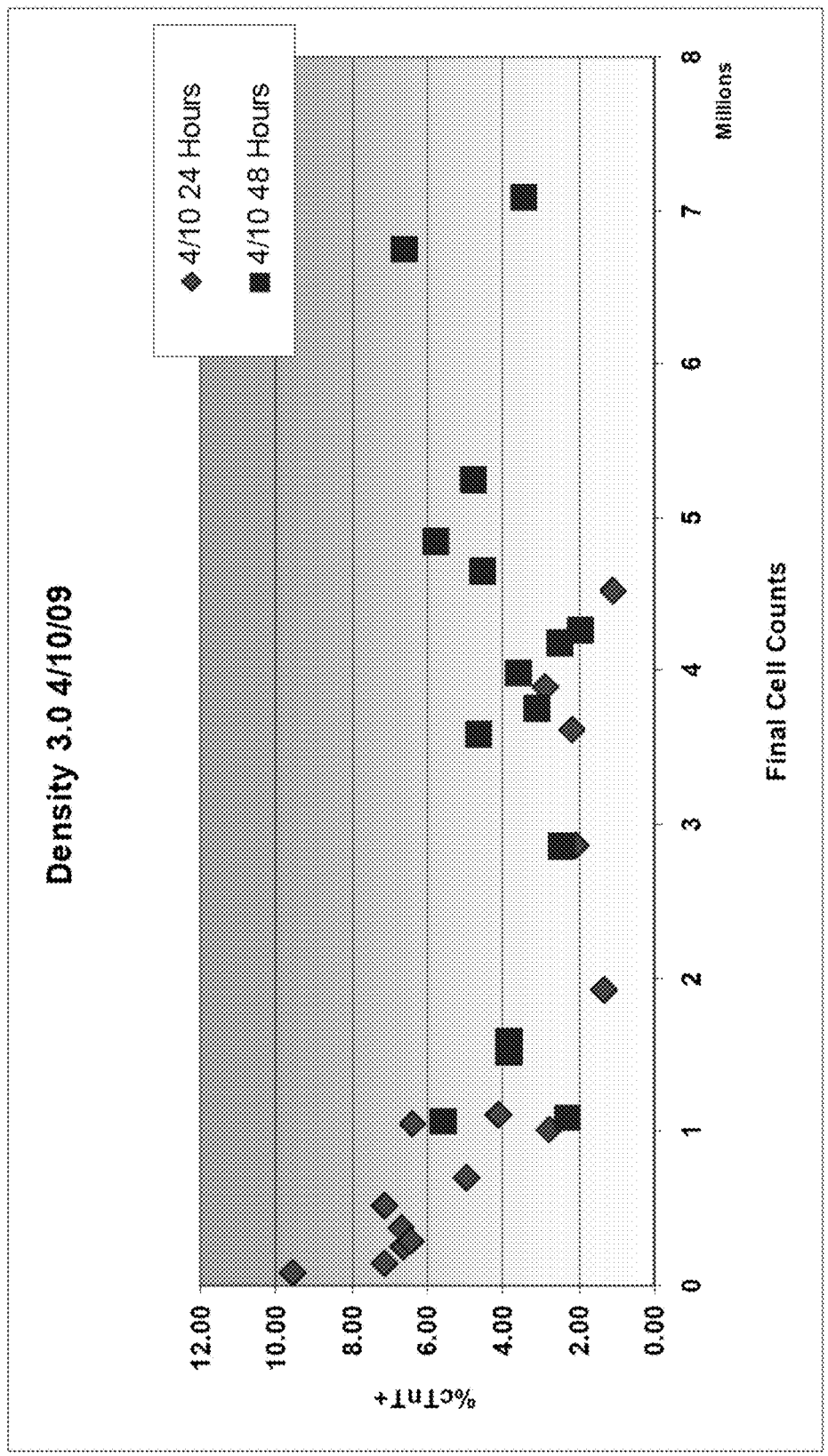
FIG. 26: Plot of final cell counts and purity from Experiment 1 suggesting that prolonged $H_{1152}$ exposure impacts purity via cell density, not through an independent mechanism.
Figure 27:
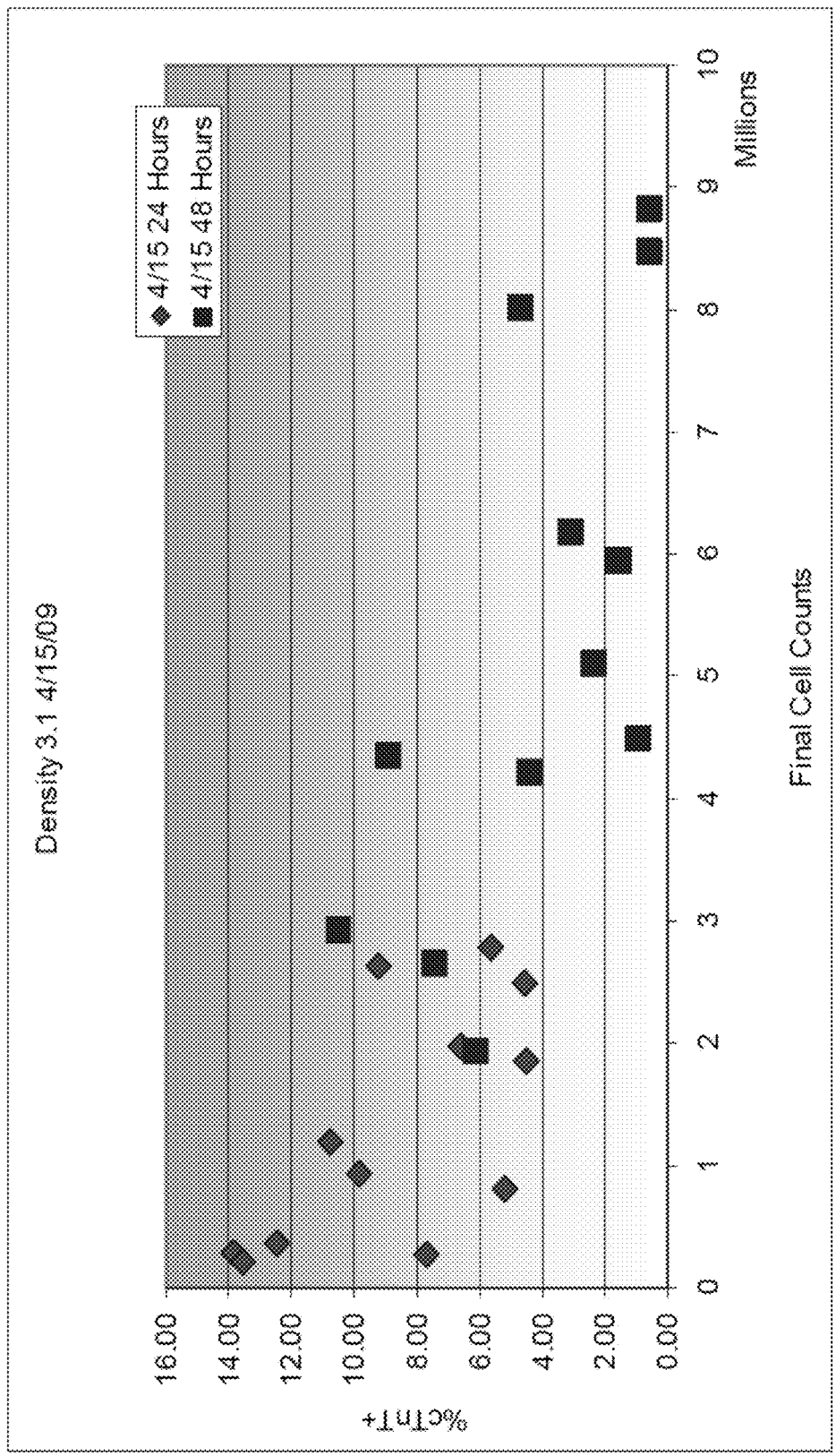
FIG. 27: Plot of final cell counts and purity from Experiment 2 suggesting that prolonged $H_{1152}$ exposure impacts purity via cell density, not through an independent mechanism.

The compound $H_{1152}$ has been shown to allow individualized pluripotent cells to self aggregate. The purpose of this Example was to see the effect of 1 day or 2 day treatment with the compound on Cardiomyocyte development. Initial testing with $H_{1152}$ included the compound in the media: 1 µM on day one with the TeSR media and 0.5 µM on day 2 with the compound in the aggregate transition media. After adopting a new method which included the $H_{1152}$ compound for 1 day at 1 µM only, there appeared to be a loss of efficiency with the initial cell survival, resulting in this study to determine if extended $H_{1152}$ would increase cell survival without a negative impact on carcinogenesis. Two experiments were designed as shown in FIGS. 22-23. Cardiomyocyte differentiation conditions and experimental parameters were summarized in Tables 11-12 and 13-14 for Experiments 1 and 2, respectively. Critical reagents and materials were obtained as described in the previous example.

Final results from Experiment 1 (Table 15) after 14 days in cardiomyocyte differentiation. Increasing $H_{1152}$ exposure duration to 48 hours increased cTnT yield in each cell density condition. Final results from Experiment 2 (Table 16) after 14 days in cardiomyocyte differentiation. Increasing $H_{1152}$ exposure duration to 48 hours increased cTnT yield in the cultures initially seeded with 3e5 and 5e5 cells/mL. Results of aggregate formation and cardiac differentiation for the experiments were presented in FIGS. 24A-J and FIGS. 25-27.

Two day treatment of H1152 at 1 µM had a significant increase in the cell survival in each of the experiments. There was a difference in the purity of cTnT positive cells between one and two day treatments which correlates with the cell survival and thus the cell density. The inventors contemplated that the decrease in purity with extended H1152 treatment is due to increased overall cell density, though the possibility of a direct effect of H1152 on cardiogenesis remains. The increase in cell survival due to the two day treatment of the compound is more significant than the decrease in cTnT purity resulting in larger yields of cTnT positive cells.

Figure 28:
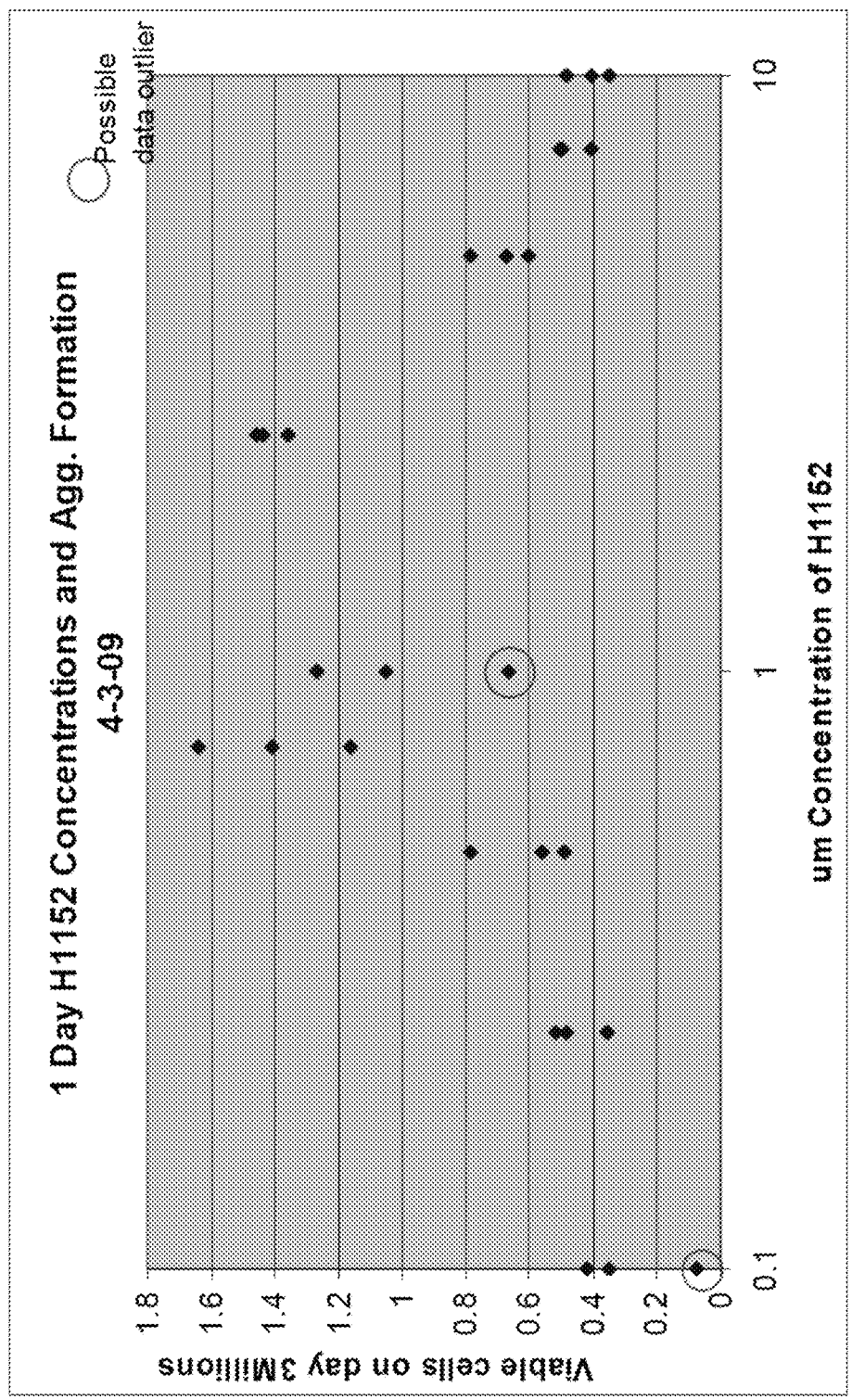
FIG. 28: Effect of different concentrations of $H_{1152}$ on cell survival with one day dose of $H_{1152}$ on IPS 6.1 cells.

Effect of different concentrations of H1152 was also tested on cell survival with one day dose of H1152 on IPS 6.1 cells (FIG. 28). This data suggested that 1 µM concentration was the optimal concentration for aggregate formation.

TABLE 11

Summary of Cardiomyocyte differentiation conditions in Experiment 1

| Conditions | Dissociation Reagent | Cell Number per Vessel | Vessel | Notes |
|---|---|---|---|---|
| 3e5 cells/ml | TrypLE trypsin | 1.5e6 | T25 | $H_{1152}$ in Cardiac formation media only, 24 hour exposure @ 1 µM |
| 5e5 cells/ml | TrypLE trypsin | 2.5e6 | T25 | $H_{1152}$ in Cardiac formation media only, 24 hour exposure @ 1 µM |
| 7e5 cells/ml | TrypLE trypsin | 3.75e6 | T25 | $H_{1152}$ in Cardiac formation media only, 24 hour exposure @ 1 µM |
| 10e5 cells/ml | TrypLE trypsin | 5e6 | T25 | $H_{1152}$ in Cardiac formation media only, 24 hour exposure @ 1 µM |
| 15e5 cells/ml | TrypLE trypsin | 7.5e6 | T25 | $H_{1152}$ in Cardiac formation media only, 24 hour exposure @ 1 µM |
| 3e5 cells/ml | TrypLE trypsin | 1.5e6 | T25 | $H_{1152}$ in Cardiac formation media and transition media, 48 hour exposure @ 1 µM |
| 5e5 cells/ml | TrypLE trypsin | 2.5e6 | T25 | $H_{1152}$ in Cardiac formation media and transition media, 48 hour exposure @ 1 µM |
| 7e5 cells/ml | TrypLE trypsin | 3.75e6 | T25 | $H_{1152}$ in Cardiac formation media and transition media, 48 hour exposure @ 1 µM |

TABLE 11-continued

Summary of Cardiomyocyte differentiation conditions in Experiment 1

| Conditions | Dissociation Reagent | Cell Number per Vessel | Vessel | Notes |
|---|---|---|---|---|
| 10e5 cells/ml | TrypLE trypsin | 5e6 | T25 | $H_{1152}$ in Cardiac formation media and transition media, 48 hour exposure @ 1 μM |
| 15e5 cells/ml | TrypLE trypsin | 7.5e6 | T25 | $H_{1152}$ in Cardiac formation media and transition media, 48 hour exposure @ 1 μM |

TABLE 12

Experimental Parameters for Experiment 1

| Parameter | Method | Time point |
|---|---|---|
| Cell morphology | Phase contrast microscopy | Day 14 |
| Cell Counts | Cell count by Cedex | End of the cardio process |
| Cardiomyocyte differentiation | Flow cytometry | End of the cardio process |

TABLE 13

Summary of Cardiomyocyte differentiation conditions in Experiment 2

| Conditions | Dissociation Reagent | Cell Number per Vessel | Vessel | Notes |
|---|---|---|---|---|
| 3e5 cells/ml | TrypLE trypsin | 1.5e6 | T25 | $H_{1152}$ in Cardiac formation media only, 24 hour exposure @ 1 μM |
| 5e5 cells/ml | TrypLE trypsin | 2.5e6 | T25 | $H_{1152}$ in Cardiac formation media only, 24 hour exposure @ 1 μM |
| 10e5 cells/ml | TrypLE trypsin | 5e6 | T25 | $H_{1152}$ in Cardiac formation media only, 24 hour exposure @ 1 μM |
| 15e5 cells/ml | TrypLE trypsin | 7.5e6 | T25 | $H_{1152}$ in Cardiac formation media only, 24 hour exposure @ 1 μM |
| 3e5 cells/ml | TrypLE trypsin | 1.5e6 | T25 | $H_{1152}$ in Cardiac formation media and transition media, 48 hour exposure @ 1 μM |
| 5e5 cells/ml | TrypLE trypsin | 2.5e6 | T25 | $H_{1152}$ in Cardiac formation media and transition media, 48 hour exposure @ 1 μM |
| 10e5 cells/ml | TrypLE trypsin | 5e6 | T25 | $H_{1152}$ in Cardiac formation media and transition media, 48 hour exposure @ 1 μM |
| 15e5 cells/ml | TrypLE trypsin | 7.5e6 | T25 | $H_{1152}$ in Cardiac formation media and transition media, 48 hour exposure @ 1 μM |

TABLE 14

Experimental Parameters for Experiment 2

| Parameter | Method | Time point |
|---|---|---|
| Cell Counts | Cell count by Cedex | End of the cardio process |
| Cardiomyocyte differentiation | Flow cytometry | End of the cardio process |

TABLE 15

Summary of Results for Experiment 1

| Density 3.0 | Average Cell Count per flask (in millions) | Average % Troponin T+ | Average Cardiomyocyte Yield | Average ratio iPS to CM | Average # cTnT Cells/Liter (in millions) |
|---|---|---|---|---|---|
| 3e5_24 Hours | 0.25 ± 0.11 | 6.83 ± 0.26 | 17445 ± 7677 | 99 ± 45 | 2.91 ± 1.27 |
| 3e5_48 Hours | 1.39 ± 0.28 | 4.40 ± 1.00 | 59575 ± 1514 | 25 ± 1 | 9.92 ± 0.25 |
| 5e5_24 Hours | 0.46 ± 0.48 | 6.26 ± 3.40 | 18123 ± 10004 | 180 ± 119 | 3.02 ± 1.66 |
| 5e5_48 Hours | 3.41 ± 0.47 | 3.37 ± 1.12 | 117137 ± 48094 | 24 ± 11 | 19.52 ± 8.01 |
| 7e5_24 Hours | 0.77 ± 0.29 | 5.41 ± 1.58 | 39272 ± 5494 | 90 ± 12 | 6.54 ± 0.91 |
| 7e5_48 Hours | 3.19 ± 1.81 | 2.23 ± 0.28 | 70299 ± 40479 | 72 ± 58 | 11.71 ± 6.74 |
| 10e5_24 Hours | 1.95 ± 0.91 | 3.29 ± 2.73 | 51174 ± 22025 | 116 ± 66 | 8.53 ± 3.67 |
| 10e5_48 Hours | 4.69 ± 0.64 | 4.70 ± 1.08 | 224015 ± 71410 | 24 ± 9 | 37.33 ± 11.90 |
| 15e5_24 Hours | 4.01 ± 0.46 | 2.05 ± 0.89 | 80131 ± 31034 | 105 ± 43 | 13.35 ± 5.17 |
| 15e5_48 Hours | 6.16 ± 1.31 | 4.84 ± 1.61 | 299246 ± 127411 | 28 ± 10 | 49.87 ± 21.23 |

TABLE 16

Summary of Results for Experiment 1

| Density 3.1 | Average Cell Count per flask (in millions) | Average % Troponin T+ | Average Cardiomyocyte Yield | Average ratio iPS to CM | Average # cTnT Cells/Liter (in millions) |
|---|---|---|---|---|---|
| 3e5_24 Hours | 0.57 ± 0.54 | 12.71 ± 1.72 | 66383 ± 54471 | 33 ± 20 | 11.06 ± 9.07 |
| 3e5_48 Hours | 2.52 ± 0.51 | 7.99 ± 2.24 | 208066 ± 94874 | 8 ± 4 | 34.67 ± 15.81 |
| 5e5_24 Hours | 0.52 ± 0.35 | 9.98 ± 2.40 | 53055 ± 36109 | 67 ± 49 | 8.84 ± 6.01 |
| 5e5_48 Hours | 4.56 ± 0.48 | 5.20 ± 3.33 | 230454 ± 138874 | 14 ± 7 | 38.40 ± 23.14 |
| 10e5_24 Hours | 1.54 ± 063 | 5.42 ± 1.08 | 85129 ± 44092 | 72 ± 42 | 14.18 ± 7.34 |
| 10e5_48 Hours | 7.84 ± 1.14 | 1.40 ± 1.45 | 96206 ± 81824 | 77 ± 44 | 16.03 ± 13.63 |
| 15e5_24 Hours | 2.63 ± 0.14 | 6.48 ± 2.42 | 171264 ± 65034 | 48 ± 17 | 28.54 ± 10.83 |
| 15e5_48 Hours | 6.16 ± 1.31 | 2.36 ± 2.03 | 168815 ± 181030 | 97 ± 85 | 28.13 ± 30.17 |

Example 7

Testing the Effect of HGF Addition in Cardiomyocyte Production Process

Originally HGF was included in the media as an "induction factor" prior to the transfer of the original plated-method from Research to Development and was kept in as the protocol evolved from plated to suspension aggregates. In the plated-method, previous studies had shown it was beneficial. Motivated by cost-reduction and process simplification, the inventors revisited the need for HGF in the current suspension aggregate method. This Example summarizes a series of experiments that culminated in the optional role of HGF in the induction media. This includes both the growth factor titration experiments that led to the conclusion that HGF could be withdrawn without measurable impact, which was confirmed by the qualification runs on a larger-scale.

Aggregate formation and cardiac induction procedures of those iPS cells at different initial densities were performed essentially the same as described in Examples 4 except different concentrations of human HGF (hHGF) and FGF were applied to Aggregate Formation Medium, Aggregate Transition Medium and Cardiac Induction Medium. Experimental Design was summarized in Tables 17-18.

TABLE 17

Summary of HGF experiments

| Experiment | Experimental Design |
|---|---|
| iPS6.1 Growth Factor Titration #1 | Full matrix: hbFGF {0, 25 ng/mL} × HGF {0, 5, 20, 50, 150 ng/mL} |
| iPS6.1 Growth Factor Titration #2 | Full matrix: hbFGF {3, 6.25, 12.5, 25, 50, 100 ng/mL} × HGF {0, 20, 50 ng/mL} |
| iPS6.1 "Four Corners" | Full matrix: hbFGF {0, 25 ng/mL} × HGF {0, 50 ng/mL} |
| H9-TGZ Growth Factor Titration #2 | Full matrix: hbFGF {25, 50, 100, 150 ng/mL} × HGF {0, 20, 50} Note: Due to poor aggregate formation, triplicate flasks were consolidated on day 2 and carried out in singlicate. |
| H9-TGZ Growth Factor Titration #2 (repeat) | Full matrix: hbFGF {25, 50, 100, 150 ng/mL} × HGF {0, 20, 50} |
| iPS-MRB 1 L spinner qualification #1 | Parallel 1 L spinner flasks with and without HGF |
| iPS-MRB 1 L spinner qualification #2 | Parallel 1 L spinner flasks with and without HGF |
| iPS-MRB 1 L spinner qualification #3 | Parallel 1 L spinner flasks with and without HGF |

TABLE 18

Summary of experimental parameters of HGF experiments

| Parameter | Method | Time point |
|---|---|---|
| Cardiomyocyte purity | Flow cytometry of cTNT, GFP, or RFP | Day 14 |
| Cell yield | CEDEX | Day 14 |

This experiment clearly showed that FGF is required for the CM differentiation process to be successful. Conditions without FGF had virtually no surviving aggregates and no measurable cardiomyocytes (FIGS. 29A-B). On the other hand, all conditions with FGF yielded cardiomyocytes independent of HGF concentration (FIGS. 29A-B). There was no consistent trend in cardiomyocyte yield or iPS:CM ratio across the range of HGF concentrations tested.

Figures 30A, 30B:
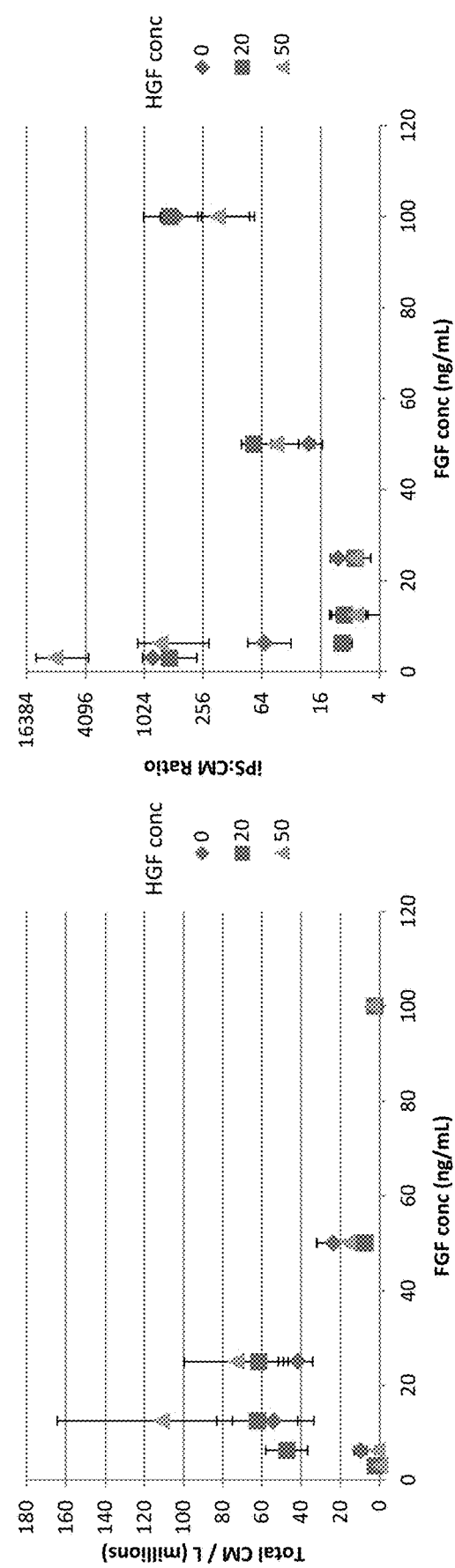
FIGS. 30A-B: Cardiac induction of iPS cells in the presence of various concentration of HGF and FGF. Error bars represent SEM for n=3 T25 flask s in one experiment.

Based on the results of the first experiment (see FIGS. 29A-B), the second iPS6.1 growth factor titration focused on the lower dose range for both FGF and HGF (FIGS. 30A-B). A very clear dose response was observed for FGF where too little FGF led to poor aggregate survival and high doses had survival but lacked cardiogenesis. Unlike the first experiment, a subtle trend was observed here in HGF concentration, particularly in the best performing FGF concentration conditions, where productivity increased with higher HGF concentrations. However, it is important to note that in no case did the omission of HGF lead to the failure of a condition which was otherwise successful in the presence of HGF.

Concurrent with the second iPS growth factor titration, a simple experiment (Table 19) was set up with iPS6.1 cells to test the 2×2 matrix of 0 and 25 ng/mL FGF and 0 and 50 ng/mL HGF. The positive concentrations of FGF and HGF were chosen based on the current best practices for iPS6.1 cells at the time and were identical to the conditions used for cardiac induction of H1 cells in both the plated and suspension processes. This experiment confirmed previous work showing the necessity of FGF for the process. However, in this experiment, inclusion of HGF together with FGF reduced overall culture efficiency versus the condition with FGF alone.

Figure 31A:
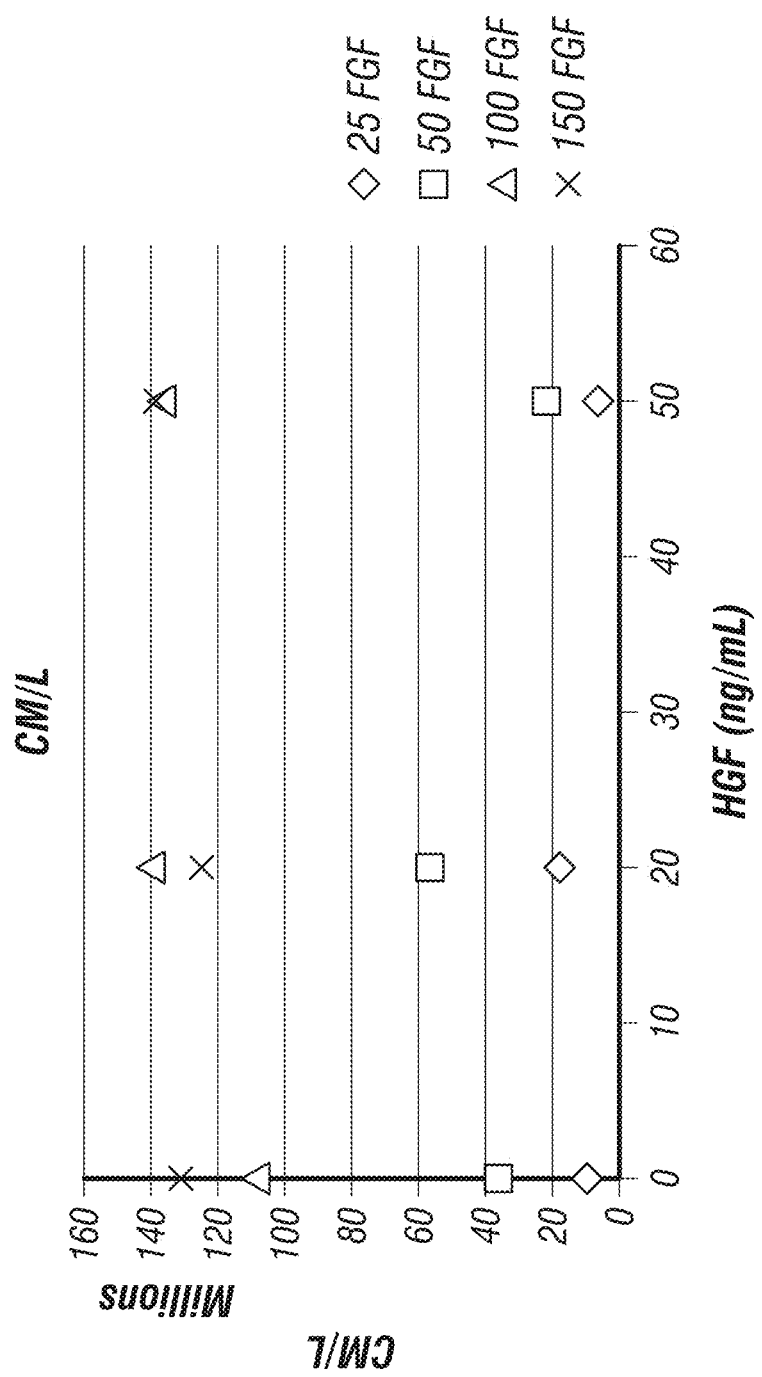
FIGS. 31A-C: Cardiomyocyte yield (FIG. 31A), H9-TGZ cell conversion efficiency ratio (FIG. 31B), and CM purity (FIG. 31C) as a function of HGF concentration. Each point represents a single T25 flask consolidated from multiple T25 flasks on day 2 due to low aggregate formation efficiency.
Figure 31B:
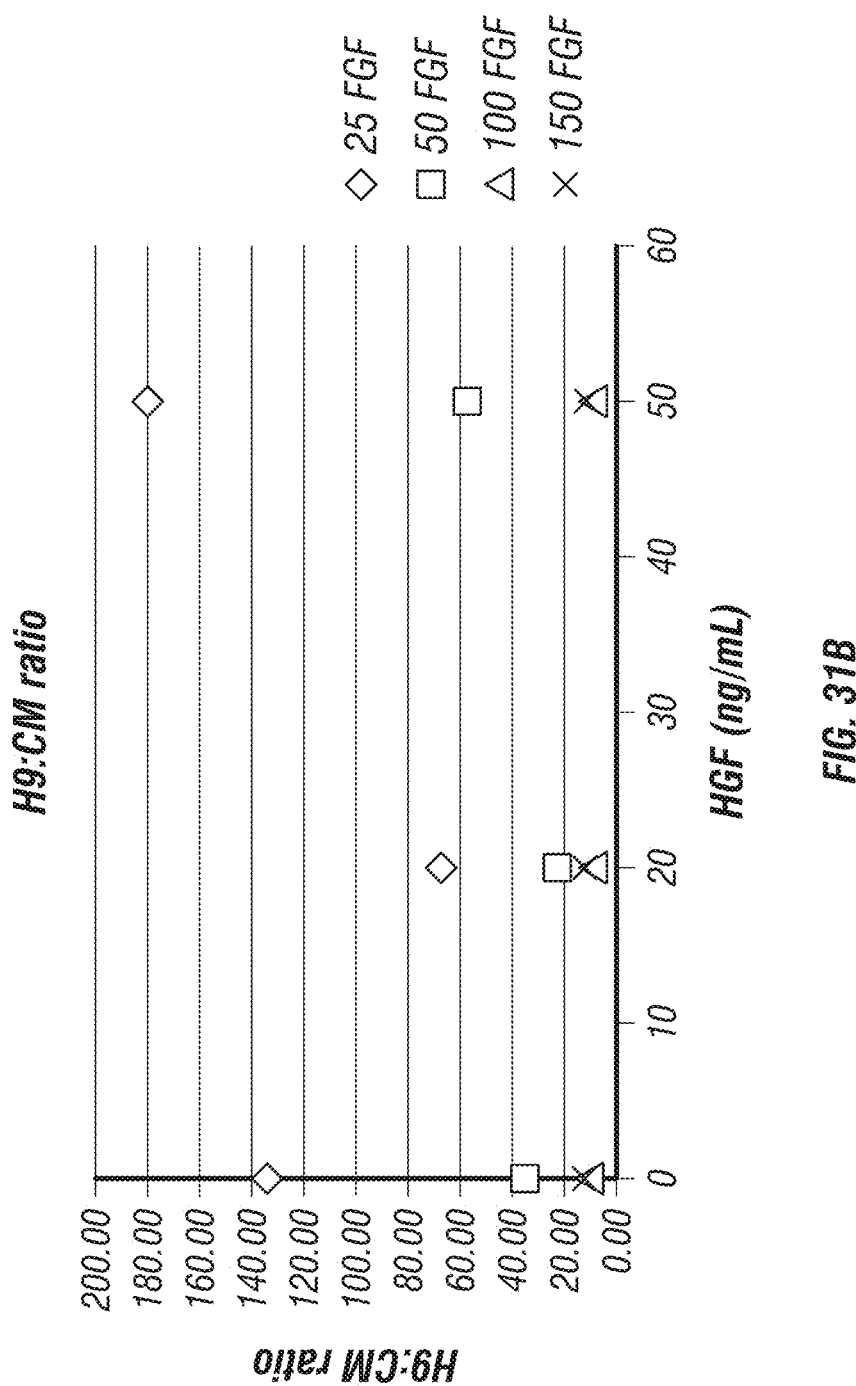
Figure 31C:
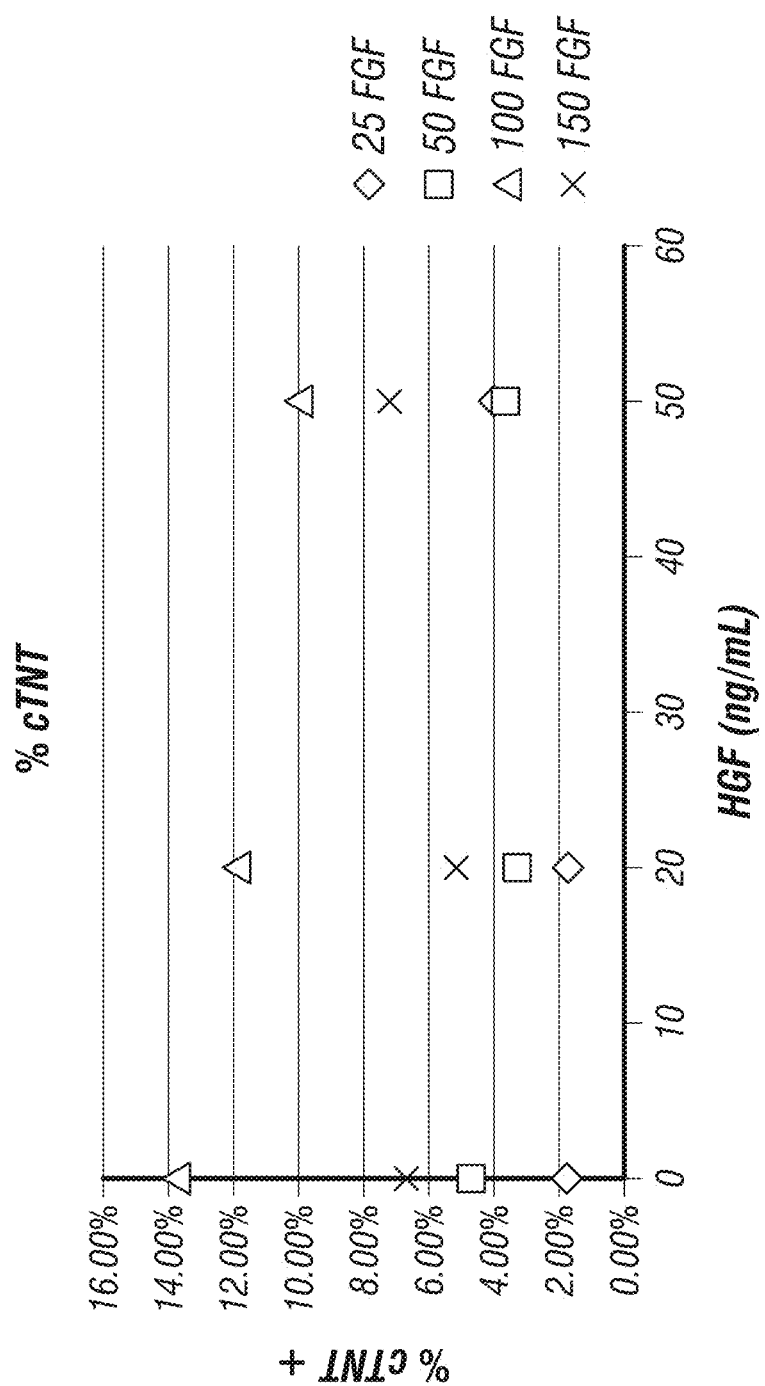

While the iPS6.1 optimization was underway, a separate series of experiments was conducted to optimize the growth factor concentrations for the H9-TGZ cells. Initial experiments had indicated that higher levels of FGF were required for efficient cardiac induction of H9-TGZ cells. Therefore, the FGF range tested was higher than that in the recent iPS6.1 experiments. This experiment confirmed that optimum cardiomyocyte production requires 100-150 ng/mL FGF with the H9-TGZ cells (FIGS. 31A-C). No trend was observed in process efficiency across different HGF concentrations.

Figure 32A:
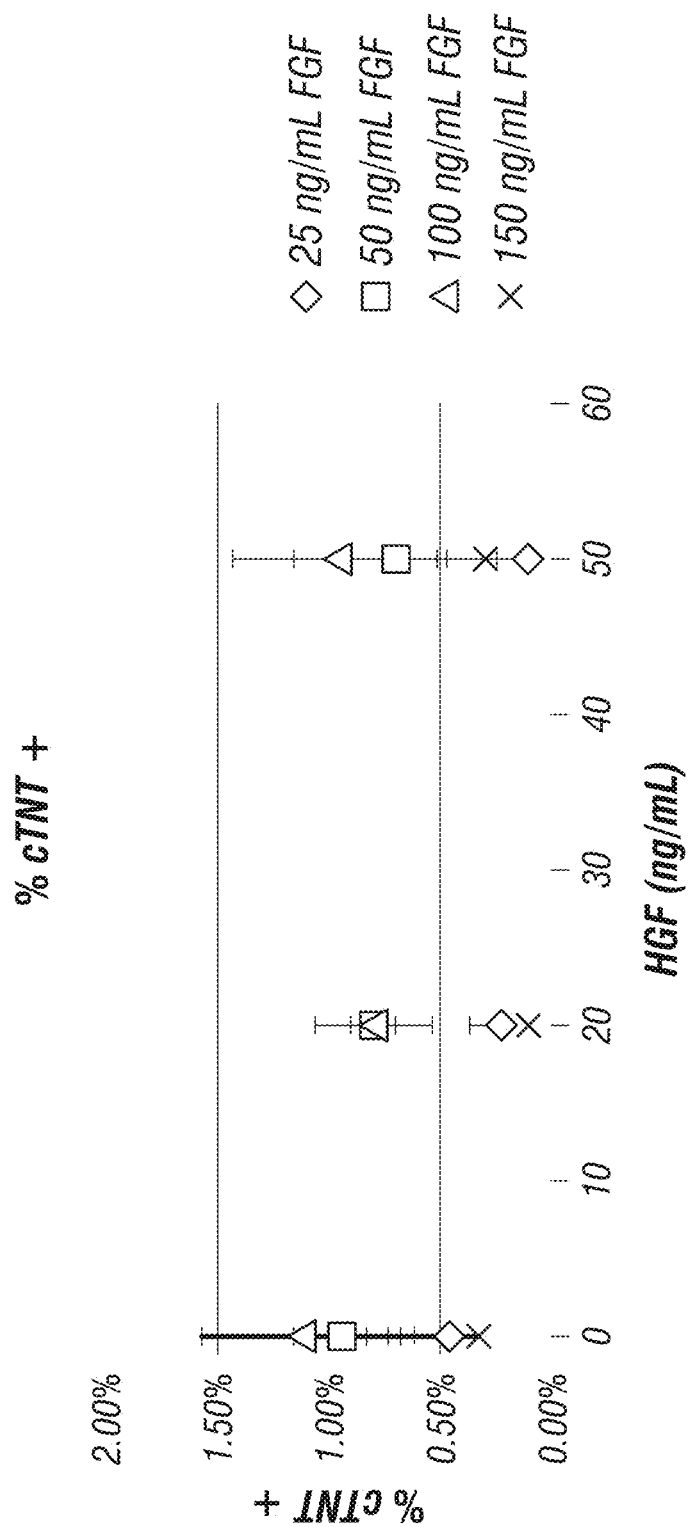
FIGS. 32A-C: Cardiomyocyte yield (FIG. 32A), H9-TGZ cell conversion efficiency ratio (FIG. 32B), and CM purity (FIG. 32C) as a function of HGF concentration. Error bars represent SEM for n=3 T25 flasks in one experiment.
Figure 32B:
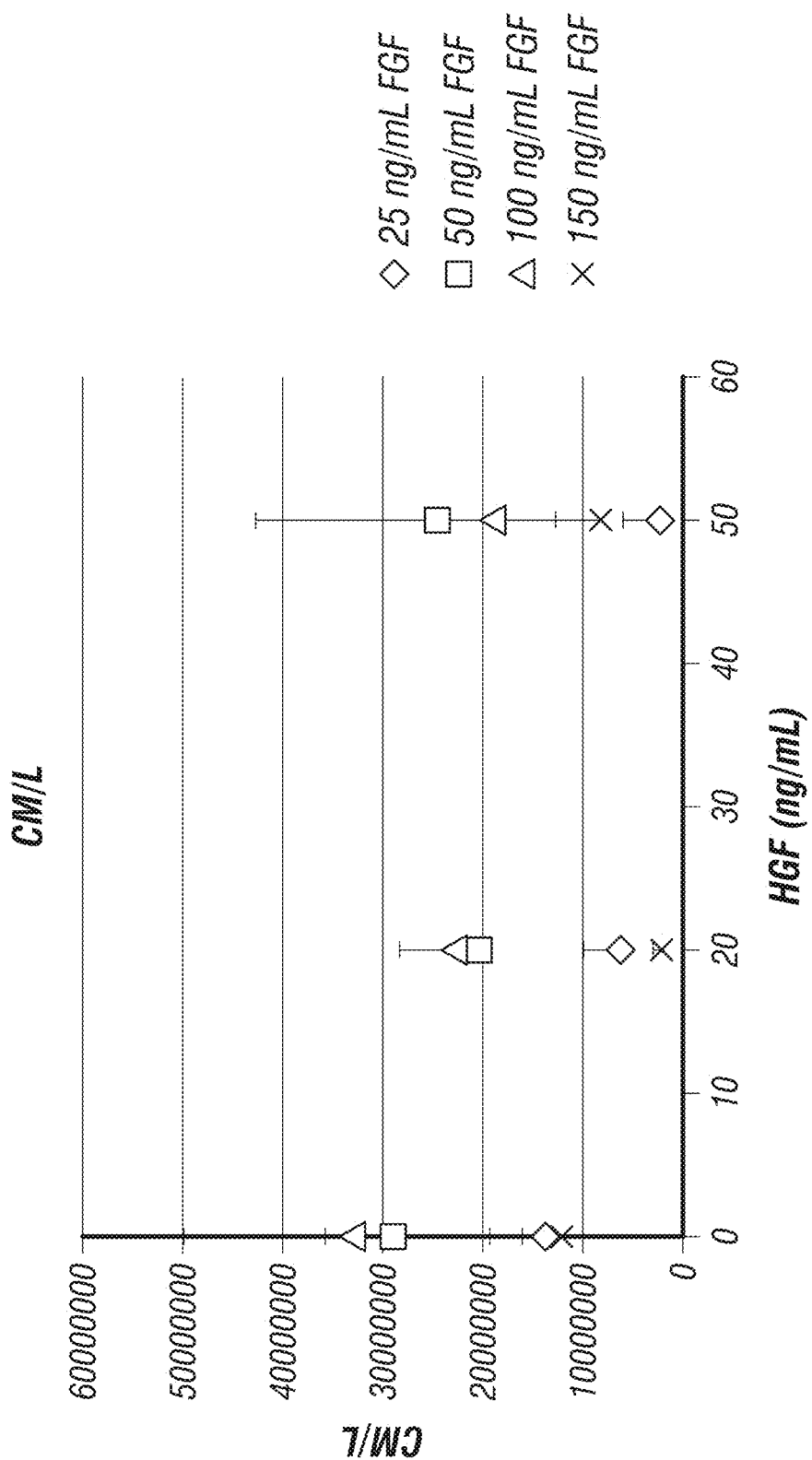
Figure 32C:
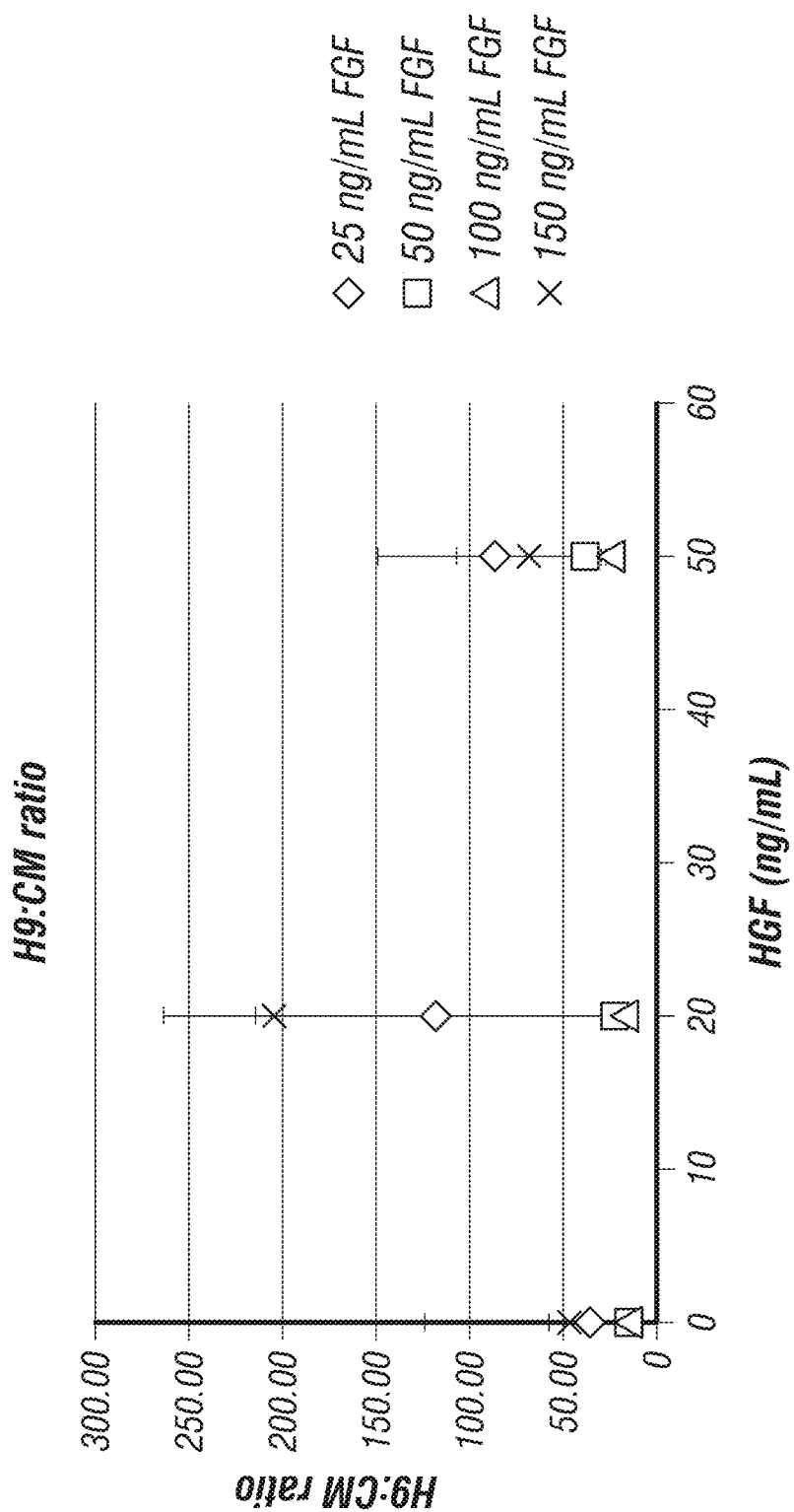

Due to the issues with aggregate formation noted above, the H9-TGZ growth factor titration experiment was repeated. In this repeat, exceptional cell survival and expansion led to overly dense cultures and likely reduced final CM purity. However, it is important to note that despite the overall poor performance of the cultures, the usual and expected decrease in performance at low FGF level was still discernable (FIGS. 32A-C). There was no observable trend of culture performance across the range of HGF concentrations tested and again, none of the "No HGF" conditions with sufficient FGF failed to produce cardiomyocytes.

A meta-analysis across these experiments was performed to assess whether the inventors could detect any measurable benefit of including HGF in the induction medium. This analysis reviewed all the available experiments for paired conditions with and without 50 ng/mL HGF. Conditions in which the control leg (with HGF) failed to produce greater than 1% cardiomyocytes were excluded. This left 14 paired conditions (11 performed in triplicate within an experiment). To aid in this analysis, a process raw material cost model was employed to estimate the cost per million cardiomyocytes under each condition. This model used the most up-to-date raw material cost and process information available at the time (~Jun. 1, 2009). This analysis is summarized in Tables 20 and 21. The data suggest that on average, there is no measurable positive or negative effect (i.e. effect greater than the experimental noise) of HGF in the inventors' cardiomyocyte production process.

TABLE 19

Summary of "Four-corners" experiment. Each entry represents a single T25 flask.

| | Label | Input count | Harvest Count | % cTNT+ | # of CMs | input iPS:CM | Million CMs/L |
|---|---|---|---|---|---|---|---|
| HGF + FGF | iPS +/+ 5c | 2420930 | 7.10E+04 | 6.3 | 4473 | 541 | 0.89 |
| | iPS +/+ 5b | 2420930 | 1.97E+05 | 11.7 | 23049 | 105 | 4.6 |
| | iPS +/+ 5a | 2420930 | 3.93E+05 | 12.5 | 49125 | 49 | 9.6 |
| HGF only | iPS +/− 6a | 2420930 | 2.40E+04 | 1.5 | 360 | 6725 | 0.072 |
| | iPS +/− 6b | 2420930 | 0.00E+00 | 7 | 0 | N/A | 0 |
| | iPS +/− 6c | 2420930 | 6.00E+03 | 0 | 0 | N/A | 0 |
| FGF only | iPS −/+ 7c | 2420930 | 1.67E+06 | 11.2 | 187488 | 13 | 37 |
| | iPS −/+ 7b | 2420930 | 1.71E+06 | 11.9 | 203371 | 12 | 41 |
| | iPS −/+ 7a | 2420930 | 1.73E+05 | 13.1 | 22663 | 107 | 4.5 |
| No GF | iPS −/− 8a | 2420930 | 1.80E+04 | 6.8 | 1224 | 1978 | 0.24 |
| | iPS −/− 8b | 2420930 | 0.00E+00 | 2.1 | 0 | N/A | 0 |
| | iPS −/− 8c | 2420930 | 0.00E+00 | 0 | 0 | N/A | 0 |

TABLE 20

Summary of HGF vs no HGF comparisons.

| Experiment | Total Head-to-Head pairings with purity >1% | Fraction with better CM/L @ 50 ng/mL HGF than 0 | Fraction with better iPS:CM ratio @ 50 ng/mL HGF than 0 | Fraction with better $/CM @ 50 ng/mL HGF than 0 |
|---|---|---|---|---|
| First iPS GF matrix | 4 | 3/4 | 3/4 | 3/4 |
| Second iPS GF matrix | 4 | 2/4 | 2/4 | 0/4 |
| First iPS 4-corners | 1 | 0/1 | 0/1 | 0/1 |
| H9-TGZ Matrix #2 | 4 | 2/4 | 2/4 | 1/4 |
| H9-TGZ Matrix #2 repeat | 1 | 0/1 | 0/1 | 0/1 |
| Total | 14 | 7/14 | 7/14 | 4/14 |

TABLE 21

Statistical analysis of HGF vs no HGF pairwise comparisons. Paired t-test values are shown for each performance metric (CM/L, iPS:CM, $/CM). In addition the best and worst case scenarios and the average and standard deviations are shown.

| | CM/L | | iPS:CM | | $/CM | |
|---|---|---|---|---|---|---|
| | | | HGF Conc (ng/mL) | | | |
| | 0 | 50 | 0 | 50 | 0 | 50 |
| | | | p-value for paired t-test | | | |
| | | 0.28 | | 0.28 | | 0.20 |
| Best | 130 | 140 | 9 | 7 | 77 | 90 |
| Worst | 8 | 1.5 | 135 | 712 | 918 | 9000 |
| Average | 41 | 49 | 45 | 100 | 340 | 1186 |
| StDev | 37 | 50 | 43 | 189 | 292 | 2406 |

Three qualification runs were performed to confirm at large scale and with iPS6.1-MRB cells that removal of HGF has no measurable effect. The results from these runs are summarized in Table 22. Of these runs, only Run #1 would be regarded as a normal run—the overall cell and cardiomyocyte yields were atypically low in Runs 2 and 3. In run 1, the yields were effectively the same independent of HGF condition. In runs 2 and 3, higher, albeit still low, yields were obtained in the cultures with HGF compared to those without. From this, the inventors concluded that in a "normal" run, HGF addition has no effect but that in suboptimal cultures, HGF may improve culture outcomes.

TABLE 22

Qualification runs of HGF withdrawal

| | Purity (% RFP+) | | CM/L (millions) | | iPS:CM ratio | |
|---|---|---|---|---|---|---|
| Run | +HGF | −HGF | +HGF | −HGF | +HGF | −HGF |
| #1 (Jun. 6, 2009) | 6.6 | 7.3 | 48.9 | 51.5 | 10:1 | 10:1 |
| #2 (Jun. 10, 2009) | 3.7 | 1.3 | 17.5 | 3.6 | 29:1 | 140:1 |
| #3 (Jun. 14, 2009) | 2.6 | 2.2 | 10.0 | 5.1 | 50:1 | 98:1 |

In summary, using iPS6.1 and H9-TGZ cells in extensive matrix experiments, the inventors were unable to measure an effect of HGF on cardiomyocyte culture productivity. In qualification runs with iPS6.1-MRB cells at larger scale, the inventors saw some evidence that HGF may partially rescue poor performing cultures but it didn't impact yield, purity, or efficiency in a normal, higher yielding culture. Based on these results, HGF may be dispensable from the formulation for the cardiac induction medium.

Example 8

Procedure for Optimizing Cardiomyocyte Differentiation from Different Lines of Pluripotent Stem Cells and After Culture in Different Stem Cell Maintenance Media A high degree of variability has been documented when differentiating different pluripotent stem cell lines. This has been accepted in the field as a "propensity" of PSC to form various tissues (such as cardiomyocytes, blood, hepatocytes or neurons). However, this propensity between lines is documented using the same differentiation procedure for each cell line. The differentiation of PSCs to different lineages requires in vitro conditions that direct cells through developmental stages and ultimately to a desired phenotype. A typical differentiation procedure usually contains culture conditions that attempt to mimic the in vivo environment driving the development of a particular lineage, such as by the addition of specific growth factors. When differentiated in vitro, a number of sources contribute to the growth factor environment, including: 1) endogenous expression from the cells themselves, 2) the serum or media that the pluripotent stem cells are cultured and/or subsequently differentiated in, and 3) the addition of exogenous growth factors. In regard to the endogenous expression of growth factors, this can arise from clone-to-clone variability and from differences in the primary culture of the cells. All the sources contributing to the growth factor environment in a given differentiation culture must be accounted for and balanced in order to achieve an optimal differentiation. This may require: 1) the addition of antagonists to reduce the total signal in certain pathways, 2) the addition of agonists to increase the total signal of certain pathways or 3) combinations of agonists and or antagonists to optimize the signal.

This Example describes a procedure to maximize the differentiation potential of multiple PSC lines or clones, grown in variable primary culture conditions, to the cardiomyocyte lineage by manipulating salient signaling pathways, including BMP and Activin/Nodal. This procedure includes: 1) screening the cardiogenic potential of each cell line in a number of conditions, followed by 2) customizing the differentiation protocol for an individual PSC line.

The Manufacturing Procedure as described in the previous Examples is followed and modified as detailed below.

At any point during aggregate formation but preferably at day 3 of differentiation, to the typical differentiation culture media (outlined in the previous Manufacturing Procedure), various combinations of growth factor agonists and antagonists were added. Including: a) No additional growth factors; b) Variable concentrations of BMP4 alone. For example, 1 ng/ml, 5 ng/ml, 10 ng/ml, 20 ng/ml; c) Variable concentrations of Activin alone. For example, 1 ng/ml, 3 ng/ml, 6 ng/ml, 12 ng/ml; d) Variable concentrations of Dorsomorphin; e) Variable concentrations of SB-431542; f) Variable combinations of BMP4 and Activin.

Media were changed daily using the various conditions outlined in the previous paragraph up to day 7 of differentiation.

After day 7 of differentiation, the standard Manufacturing Procedure as described in the previous Examples was followed.

At days 6, 7 and 8 of differentiation, a small sample was harvested from each condition to monitor for expression of markers consistent with cardiac mesoderm by flow cytometry (Table 23). This information was used to predict optimal culture conditions to differentiate cells into the cardiac lineages. Typically, a 30% KDR+/PDGFR-a+ population is consistent with the successful induction of cardiac mesoderm.

At the endpoint of the assay, typically day 14 of differentiation, the cultures were harvested and analyzed for percent cardiomyocytes based on expression of proteins consistent with cardiomyocyte development (Table 23). In addition, a total cell count was determined.

For example, FIGS. 33A-D details the results of a growth factor/inhibitor screen utilizing varying concentrations of BMP (1 ng/mL, 10 ng/mL), dorsomorphin (2 uM, 0.2 uM), Activin A (1 ng/mL, 10 ng/mL), SB-431542 (10 uM, 0.1 uM) and a combination of Activin A (6 ng/mL) and BMP4 (10 ng/mL) (variable concentrations of compounds were added at days 3 through 7 of differentiation). Analysis of the cells at day 14 post aggregate formation (FIGS. 33C and 33D) shows a higher concentration of Troponin T (CTNT) positive cells in the treatment comprising a combination of Activin A and BMP4. The presence of CTNT was determined by flow cytometry using an anti-CTNT Antibody. As such, the results of this experiment reveal that the optimized culture conditions for the stem cell clone iPS 6.1 MRB for differentiation into cardiomyocytes is a combination of Activin A (6 ng/mL) and BMP4 (10 ng/mL).

Based on marker analysis (for example, using flow cytometry) from days 6, 7, 8, 9, 10 and/or at earlier or later time points in differentiation and optionally the total yield of cardiomyocytes, the cultures that had the highest yield and/or purity (or another measure of optimal cell culture growth and/or differentiation for the desired differentiated cell type, such as function of a cell-specific enzyme or receptor or electrophysiological function specific for the desired cell type) were identified and, therefore, the corresponding culture conditions are known that resulted in optimal differentiation of the pluripotent stem cell clone utilized. These culture conditions can then be routinely utilized during the Manufacturing Procedure, thereby coupling the pluripotent stem cells from the same cell line or clone with the same culture medium composition, or further manipulations can be investigated to increase the yield.

TABLE 23

Non-limiting Examples of Growth Factors and Markers associated with developmental stages of Cardiac Mesoderm and Cardiomyocytes

| Examples of Growth Factors that induce Cardiac Mesoderm | Examples of Cardiac Mesoderm Markers | Examples of Growth Factors specifying cardiomyocytes | Examples of Cardiomyocyte Markers |
|---|---|---|---|
| Wnt | KDR | BMP2 | NKX2.5 |
| ActivinA/Nodal | PDGFR-a | BMP4 | TBX5 |
| BMP2 | CXCR4 | BMP10 | GATA4 |
| BMP4 | CKITneg | ActivinA/Nodal | Baf60c |
| BMP10 | N-Cadherin | bFGF | alpha-MHC |
| bFGF | MESP1 | EGF | CTNT |
| IGF | | IGF | MLC2A |
| | | (Wnt inhibitors) | MLC2V |
| | | | MLC1V |
| | | | Sarcomeric |
| | | | alpha-actinin |
| | | | NPPA |

Abbreviations and definition
PSC = Pluripotent Stem Cells - Embryonic and Induced Pluripotent Stem Cells.
BMP4 = Bone Morphogenic Protein-4; Developmental morphogen
Activin = ActivinA (Activin and Nodal signaling can be used interchangeably in this context). Developmental morphogen
SB-431542 = Small molecule inhibitor of the TGFβ/Activin/Nodal signaling pathway
Dor = Dorsomorphin. Small molecule inhibitor of the BMP pathway. Also known as Compound C
KDR = Kinase Insert Domain Receptor, also known as VEGFR-2
PDGFR-a = Platelet Derived Growth Factor Receptor-alpha All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Appln. 61/058,858
U.S. Appln. 61/172,079
U.S. Appln. 61/184,546
U.S. Pat. No. 5,030,015
U.S. Pat. No. 5,478,838
U.S. Pat. No. 5,843,780
U.S. Pat. No. 6,099,832
U.S. Pat. No. 6,200,806
U.S. Pat. No. 6,280,718
U.S. Pat. No. 6,602,711
U.S. Pat. No. 6,833,269
U.S. Pat. No. 6,833,269
U.S. Pat. No. 7,029,913
U.S. Patent Publn. 2002/0086005
U.S. Patent Publn. 2002/0168766
U.S. Patent Publn. 2003/0022367
U.S. Patent Publn. 2003/0087919
U.S. Patent Publn. 2003/0125344
U.S. Patent Publn. 2003/0211603
U.S. Patent Publn. 2004/0002507
U.S. Patent Publn. 2004/0002508
U.S. Patent Publn. 2004/0014755
U.S. Patent Publn. 2005/0192304
U.S. Patent Publn. 2005/0209261
U.S. Patent Publn. 2007/0116680
U.S. Patent Publn. 2007/0238170

U.S. Patent Publn. 2008/0038820
U.S. Patent Publn. 2008/0171385.
U.S. Patent Publn. 2008/0226558
U.S. Patent Publn. 2008/0254003
U.S. Patent Publn. 2009/0047739
Amit et al., *Dev. Bio.*, 227:271-278, 2000.
Andrews et al., In: *Teratocarcinomas and Embryonic Stem Cells*, Robertson (Ed.), IRL Press, 207-246, 1987.
*Animal Cell Culture*, Freshney (Ed.), 1987.
Byrne et al., *Nature*, 450(7169):497-502, 2007.
Cell Therapy: Stem Cell Transplantation, Gene Therapy, and Cellular Immunotherapy, Morstyn and Sheridan (Eds.), Cambridge University Press, 1996.
Chiu et al., *Ann. Thorac. Surg.*, 60:12, 1995.
Current Protocols in Molecular Biology and Short Protocols in Molecular Biology, 1987 and 1995.
Doe et al., *J. Pharmacol. Exp. Ther.*, 32:89-98, 2007.
Doevendans et al., *J. Mol. Cell Cardiol.*, 32:839, 2000.
Dunn et al., *Drugs*, 61:1957, 2001.
Embryonic Stem Cell Differentiation in vitro, 1993.
Evans et. al., *Nature*, 292:154, 1981.
Fernandes, et al., *J. Biotechnology*, 132(2):227-236, 2007.
Gene Targeting, A Practical Approach, IRL Press at Oxford University Press, 1993.
Gene Transfer Vectors for Mammalian Cells, 1987.
Guide to Techniques in Mouse Development, 1993.
Harb et al., *PLoS One*, 20; 3(8):e3001, 2008.
Hematopoetic Stem Cell Therapy, Ball et al. (Eds.), Churchill Livingstone, 2000.
Igelmund et al., *Pflugers Arch.*, 437:669, 1999.
In vitro Methods in Pharmaceutical Research, Academic Press, 1997.
Ishizaki, et al., *Mol. Pharmacol.*, 57:976-983, 2000.
Itskovitz-Eldor et al., *Mol Med.*, 6(2):88-95, 2000.
Jainchill et al., *J. Virol.*, 4:549, 1969.
Keller et al., *Curr. Opin. Cell Biol.*, 7:862-869, 1995.
Klimanskaya et al., *Lancet.*, 365:P1636-1641, 2005.
Kodama et al., *J. Cell. Physiol.*, 112:89, 1982.
Li et al., *J. Clin. Invest.*, 100:1991, 1997.
Ludwig et al., *Nat. Biotechnol.*, 24(2):185-187, 2006b.
Ludwig et al., *Nat. Methods*, 3(8):637-46, 2006a.
Manipulating the Mouse Embryo A Laboratory Manual, Second Edition, Cold Spring Harbor Laboratory Press, 1994.
Martin, *Proc. Natl. Acad. Sci. USA*, 78:7634B7638; 1982.
Martin, *Proc. Natl. Acad. Sci. USA*, 78:7634, 1981.
Marvin et al., *Genes Dev.*, 15:316, 2001.
Murry et al., *J. Clin. Invest.*, 98:2209, 1996.
Nakajima et al., *Cancer Chemother. Pharmacol.*, 52:319-324, 2003.
Nakano et al., *Science*, 272, 722, 1996.
Narazaki et al., Circulation, 118(5): 498-506, 2008.
PCT Appln. PCT/US04/42917
PCT Appln. WO 2001/088100
PCT Appln. WO 2001/51616
PCT Appln. WO 2003/004626
PCT Appln. WO 2002/076976
PCT Appln. WO 2003/059913
PCT Appln. WO 2003/062225
PCT Appln. WO 2003/062227
PCT Appln. WO 2004/039796
PCT Appln. WO 2005/080554
PCT Appln. WO 2005/123902
PCT Appln. WO 1998/30679
PCT Appln. WO 2002/44343
PCT Appln. WO 2003/050251
Properties and uses of Embryonic Stem Cells: Prospects for Application to Human Biology and Gene Therapy, 1998.
Reinecke et al., *Circ Res.*, 94:e56-e60, 2004.
Reinecke et al., *Circulation*, 100:193, 1999.
Reubinoff et al., *Nat. Biotechnol.*, 18:399-404, 2000.
Roach et al., *Eur. Urol.*, 23(1):82-87, 1993.
Sasaki et al., *Pharmacol. Ther.*, 93:225-232, 2002.
Scalia et al., *J. Cell. Biochem.*, 82:610, 2001.
Schneider et al., *Genes Dev.*, 15:304, 2001.
Smith, In: *Origins and Properties of Mouse Embryonic Stem Cells*, Annu. Rev. Cell. Dev. Biol., 2000.
Takahashi and Yamanaka, *Cell.*, 126(4):663-676, 2006.
Takahashi et al., *Cell*, 126(4):663-76, 2007.
Takahashi et al., *Cell*, 131:861-872, 2007.
Teratocarcinomas and embryonic stem cells: A practical approach. 1987.
Thomson and Marshall, *Curr. Top. Dev. Biol.*, 38:133-165, 1998.
Thomson and Odorico, *Trends Biotechnol.*, 18(2):53-57, 2000.
Thomson et al. *Proc. Natl. Acad. Scie. USA*, 92:7844-7848, 1995.
Thomson et al., *Science*, 282:114, 1998.
Vickers, In: *In vitro Methods in Pharmaceutical Research*, Academic Press, 375-410, 1997
Watanabe et al., *Nature Neurosci.*, 8:288-296, 2005.
Wobus et al., *Ann. N.Y. Acad. Sci.*, 27:752, 1995,
Xu et al., *Nat. Biotechnol.*, 19:971-974, 2001.
Ying et al., *Cell*, 115:281-292, 2003.
Yu and Thompson, *Genes Dev.* 22(15):1987-97, 2008.
Yu et al., *Science*, 318:1917-1920, 2007.
Yu et al., *Science*, 324(5928):797-801, 2009.
Zhang, et al., *Zhongguo Xiu Fu Chong Jian Wai Ke Za Zhi.*, 23(1):82-86, 2009.

What is claimed is:

1. A method for producing human cardiomyocytes, the method comprising the steps of:
   a) incubating human pluripotent stem cells from a selected cell clone in suspension culture under conditions to form aggregates, wherein the conditions to form aggregates comprises externally added Rho-associated kinase (ROCK) inhibitor, myosin II inhibitor, fibroblast growth factor (FGF) or hepatic growth factor (HGF);
   b) subjecting the aggregates to a mesoderm-forming culture medium under conditions to form mesoderm, said conditions including externally added molecules, said molecules comprising bFGF and a second Wnt signaling activator in the culture medium; and
   c) differentiating the mesoderm into human cardiomyocytes in a cardiac differentiation medium;
wherein the selected cell clone is an induced pluripotent stem (iPS) cell clone.

2. The method of claim 1, wherein the selected cell clone is a progeny of a single human pluripotent stem cell in an adherent culture.

3. The method of claim 1, wherein from about $10^6$ to about $10^{10}$ of the human pluripotent stem cells are first incubated in the suspension culture in step a).

4. The method of claim 1, wherein the myosin II inhibitor is blebbistatin.

5. The method of claim 1, wherein the human pluripotent stem cells and/or cardiomyocytes differentiated therefrom contain one or more transgenes.

6. The method of claim 5, wherein the one or more transgenes encode a selectable and/or screenable marker under the control of a cardiomyocyte-specific promoter.

7. The method of claim 1, further comprising enriching or purifying the differentiated human cardiomyocytes.

8. The method of claim 1, wherein the cardiac differentiation medium comprises externally added fibroblast growth factor (FGF) in an amount of from 5 to 200 ng/ml.

9. The method of claim 1, wherein the suspension culture is rotated or shaken at a speed of about 15 rpm to 100 rpm.

10. The method of claim 1, wherein the cardiac differentiation medium is prepared from a selected batch of media by adjusting the level of one or more differentiation factors in said media at amounts appropriate for cardiac differentiation of the selected cell clone and media batch employed.

11. The method of claim 10, wherein the differentiation factors whose level are adjusted in the media comprise one or more of modulators of signaling pathways of bone morphogenetic protein, ActivinA/Nodal, vascular endothelial growth factor (VEGF), dickkopf homolog 1 (DKK1), basic fibroblast growth factor (bFGF), insulin growth factor (IGF), or epidermal growth factor (EGF).

12. The method of claim 11, wherein the differentiation factors comprise BMP2, BMP4, BMP10, Activin A, bFGF, IGF, EGF, BMP signaling inhibitor, or a combination thereof.

13. The method of claim 1, wherein the mesoderm-forming culture medium is free of serum.

14. The method of claim 1, wherein the culture medium further comprises human serum.

* * * * *